(12) United States Patent
Matsunobu et al.

(10) Patent No.: US 10,812,800 B2
(45) Date of Patent: *Oct. 20, 2020

(54) ARITHMETIC CODING FOR INFORMATION RELATED TO SAMPLE ADAPTIVE OFFSET PROCESSING

(71) Applicant: Sun Patent Trust, New York, NY (US)

(72) Inventors: Toru Matsunobu, Osaka (JP); Takahiro Nishi, Nara (JP); Youji Shibahara, Tokyo (JP); Hisao Sasai, Osaka (JP); Kyoko Tanikawa, Osaka (JP); Toshiyasu Sugio, Osaka (JP); Kengo Terada, Osaka (JP)

(73) Assignee: SUN PATENT TRUST, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/239,927

(22) Filed: Jan. 4, 2019

(65) Prior Publication Data

US 2019/0141330 A1    May 9, 2019

Related U.S. Application Data

(63) Continuation of application No. 15/014,374, filed on Feb. 3, 2016, now Pat. No. 10,212,425, which is a
(Continued)

(51) Int. Cl.
*H04N 19/13* (2014.01)
*G06T 9/00* (2006.01)
(Continued)

(52) U.S. Cl.
CPC .............. *H04N 19/13* (2014.11); *G06T 9/00* (2013.01); *H04N 19/117* (2014.11);
(Continued)

(58) Field of Classification Search
CPC ...... H04N 19/13; H04N 19/157; H04N 19/86; H04N 19/70; H04N 19/82; H04N 19/196;
(Continued)

(56) References Cited

U.S. PATENT DOCUMENTS 5,150,203 A * 9/1992 Fairhurst ................ H04N 9/646
348/630
8,138,956 B2    3/2012 Hsu et al.
(Continued)

FOREIGN PATENT DOCUMENTS

CN         1949873      4/2007
CN        101771879     7/2010
(Continued)

OTHER PUBLICATIONS

J. Xu, et al., "AHG6: on SAO signalling", JCT-VC of ITU-T and ISO/EEC, JCTVC-J0268, Ver. 1, Jul. 3, 2012, pp. 1-9.
(Continued)

*Primary Examiner* — Joseph Suh
(74) *Attorney, Agent, or Firm* — Wenderoth, Lind & Ponack, L.L.P.

(57) ABSTRACT

An image coding method includes: performing context arithmetic coding to consecutively code (i) first information indicating whether or not to perform sample adaptive offset (SAO) processing for a first region of an image and (ii) second information indicating whether or not to use, in the SAO processing for the first region, information on SAO processing for a region other than the first region, the context arithmetic coding being arithmetic coding using a variable probability, the SAO processing being offset processing on a pixel value; and performing bypass arithmetic coding to code other information which is information on the SAO processing for the first region and different from the first information or the second information, after the first infor-
(Continued)

mation and the second information are coded, the bypass arithmetic coding being arithmetic coding using a fixed probability.

3 Claims, 57 Drawing Sheets

Related U.S. Application Data continuation of application No. 13/908,278, filed on Jun. 3, 2013, now Pat. No. 9,305,367.

(60) Provisional application No. 61/657,183, filed on Jun. 8, 2012.

(51) Int. Cl.
| | |
|---|---|
| *H04N 19/70* | (2014.01) |
| *H04N 19/196* | (2014.01) |
| *H04N 19/61* | (2014.01) |
| *H04N 19/117* | (2014.01) |
| *H04N 19/157* | (2014.01) |
| *H04N 19/82* | (2014.01) |
| *H04N 19/86* | (2014.01) |
| *H04N 19/169* | (2014.01) |

(52) U.S. Cl.
CPC ....... *H04N 19/157* (2014.11); *H04N 19/1887* (2014.11); *H04N 19/196* (2014.11); *H04N 19/61* (2014.11); *H04N 19/70* (2014.11); *H04N 19/82* (2014.11); *H04N 19/86* (2014.11)

(58) Field of Classification Search
CPC .. H04N 19/117; H04N 19/1887; H04N 19/61; G06T 9/00
See application file for complete search history.

(56) References Cited

U.S. PATENT DOCUMENTS

| | | | |
|---|---|---|---|
| 8,437,394 B2 | 5/2013 | Fu et al. | |
| 8,548,041 B2 | 10/2013 | Fu et al. | |
| 8,660,174 B2 | 2/2014 | Fu et al. | |
| 8,861,617 B2 | 10/2014 | Chen et al. | |
| 9,055,305 B2 | 6/2015 | Fu et al. | |
| 9,094,658 B2 | 7/2015 | Fu et al. | |
| 9,154,778 B2 | 10/2015 | Fu et al. | |
| 9,161,041 B2 | 10/2015 | Fu et al. | |
| 2001/0002203 A1* | 5/2001 | Cahn | G01C 21/26 375/142 |
| 2003/0081850 A1 | 5/2003 | Karczewicz et al. | |
| 2004/0056858 A1* | 3/2004 | Ohba | G06T 15/02 345/419 |
| 2007/0071090 A1 | 3/2007 | Peng et al. | |
| 2007/0139519 A1 | 6/2007 | DeCusatis et al. | |
| 2007/0285286 A1 | 12/2007 | Hussain et al. | |
| 2008/0123947 A1 | 5/2008 | Moriya et al. | |
| 2008/0123977 A1 | 5/2008 | Moriya et al. | |
| 2008/0130747 A1 | 6/2008 | Moriya et al. | |
| 2008/0130988 A1 | 6/2008 | Moriya et al. | |
| 2008/0130989 A1 | 6/2008 | Moriya et al. | |
| 2008/0130990 A1 | 6/2008 | Moriya et al. | |
| 2008/0137744 A1 | 6/2008 | Moriya et al. | |
| 2008/0159641 A1 | 7/2008 | Moriya et al. | |
| 2008/0165849 A1 | 7/2008 | Moriya et al. | |
| 2009/0034856 A1 | 2/2009 | Moriya et al. | |
| 2009/0034857 A1 | 2/2009 | Moriya et al. | |
| 2009/0079602 A1 | 3/2009 | Sze et al. | |
| 2009/0123066 A1 | 5/2009 | Moriya et al. | |
| 2009/0154567 A1 | 6/2009 | Lei et al. | |
| 2009/0168873 A1 | 7/2009 | Jeon et al. | |
| 2009/0257670 A1 | 10/2009 | Chiu et al. | |
| 2009/0296806 A1 | 12/2009 | Hsu et al. | |
| 2010/0020876 A1 | 1/2010 | Jeon et al. | |
| 2010/0074323 A1 | 3/2010 | Fu et al. | |
| 2010/0074329 A1 | 3/2010 | Fu et al. | |
| 2010/0074330 A1 | 3/2010 | Fu et al. | |
| 2010/0183079 A1 | 7/2010 | Jeon et al. | |
| 2010/0183080 A1 | 7/2010 | Jeon et al. | |
| 2011/0013890 A1* | 1/2011 | Sasaki | G11B 27/105 386/357 |
| 2011/0019739 A1 | 1/2011 | Jeon et al. | |
| 2011/0096829 A1 | 4/2011 | Han et al. | |
| 2011/0274158 A1 | 11/2011 | Fu et al. | |
| 2011/0305274 A1 | 12/2011 | Fu et al. | |
| 2011/0305277 A1 | 12/2011 | Fu et al. | |
| 2012/0082232 A1 | 4/2012 | Sole Rojals et al. | |
| 2012/0082241 A1 | 4/2012 | Tsai et al. | |
| 2012/0082244 A1 | 4/2012 | Chen et al. | |
| 2012/0177103 A1 | 7/2012 | Fu et al. | |
| 2012/0177107 A1* | 7/2012 | Fu | H04N 19/61 375/240.03 |
| 2012/0287988 A1* | 11/2012 | Chong | H04N 19/105 375/240.02 |
| 2012/0294353 A1 | 11/2012 | Fu et al. | |
| 2013/0003829 A1* | 1/2013 | Misra | H04N 19/91 375/240.12 |
| 2013/0016774 A1 | 1/2013 | Oh | |
| 2013/0022103 A1* | 1/2013 | Budagavi | H04N 19/176 375/240.02 |
| 2013/0051454 A1* | 2/2013 | Sze | H04N 19/70 375/240.02 |
| 2013/0058399 A1 | 3/2013 | Jeon et al. | |
| 2013/0064300 A1 | 3/2013 | Jeon et al. | |
| 2013/0070850 A1 | 3/2013 | Jeon et al. | |
| 2013/0114686 A1* | 5/2013 | Misra | H04N 19/52 375/240.03 |
| 2013/0114909 A1* | 5/2013 | Kim | H04N 19/463 382/233 |
| 2013/0142259 A1 | 6/2013 | Lim et al. | |
| 2013/0177069 A1* | 7/2013 | Sze | H04N 19/91 375/240.02 |
| 2013/0215959 A1 | 8/2013 | Chen et al. | |
| 2013/0259117 A1 | 10/2013 | Fu et al. | |
| 2013/0336592 A1* | 12/2013 | Matsunobu | G06T 9/00 382/239 |
| 2014/0341277 A1 | 11/2014 | Jeon et al. | |
| 2015/0124866 A1 | 5/2015 | Fu et al. | |
| 2015/0124869 A1 | 5/2015 | Fu et al. | |
| 2015/0195536 A1 | 7/2015 | Jeon et al. | |
| 2015/0350648 A1 | 12/2015 | Fu et al. | |
| 2016/0057421 A1 | 2/2016 | Oh et al. | |
| 2016/0057422 A1 | 2/2016 | Oh et al. | |
| 2016/0057423 A1 | 2/2016 | Oh et al. | |
| 2016/0057424 A1 | 2/2016 | Oh et al. | |
| 2016/0057425 A1 | 2/2016 | Oh et al. | |
| 2016/0057426 A1 | 2/2016 | Oh et al. | |
| 2016/0057427 A1 | 2/2016 | Oh et al. | |
| 2016/0057449 A1 | 2/2016 | Oh et al. | |
| 2016/0057450 A1 | 2/2016 | Oh et al. | |
| 2017/0332078 A1 | 11/2017 | Lim et al. | |
| 2019/0238852 A1 | 8/2019 | Lim et al. | |

FOREIGN PATENT DOCUMENTS

| | | |
|---|---|---|
| CN | 102165774 | 8/2011 |
| EP | 2 007 147 | 12/2008 |
| EP | 2 874 391 | 5/2015 |
| JP | 2007-142637 | 6/2007 |
| RU | 2368095 | 9/2009 |
| RU | 2371881 | 10/2009 |
| TW | 200952351 | 12/2009 |
| TW | 201223291 | 6/2012 |
| WO | 2007/008018 | 1/2007 |
| WO | 2008/053755 | 5/2008 |
| WO | 2012/018197 | 2/2012 |
| WO | 2012/070857 | 5/2012 |
| WO | 2013/177975 | 12/2013 |

(56) References Cited

FOREIGN PATENT DOCUMENTS

| WO | 2014/000049 | 1/2014 |
|---|---|---|
| WO | 2014/008109 | 1/2014 |

OTHER PUBLICATIONS

Office Action dated Apr. 8, 2019 in European Patent Application No. 13 800 830.5.
ISO/IEC 14496-10 (MPEG-4 Part 10: Advanced Video coding), Oct. 1, 2004.
Frank Bossen, "Common test conditions and software reference configurations", JCTVC-H1100, Joint Collaborative Team on Video Coding (JCT-VC) of ITU-T SG16 WP3 and ISO/IEC JTC1/SC29/WG11 8th Meeting, San Jose, CA USA, Feb. 1-10, 2012.
Benjamin Bross et al, "High efficiency video coding (HEVC) text specification draft 7", Joint Collaborative Team on Video Coding (JCT-VC) of ITU-T SG16 WP3 and ISO/IEC JTC1/SC29/WG11, JCTVC-I1003_d2, Ver.3, 9th Meeting: Geneva, CH, Apr. 27-May 7, 2012.
E. Maani et al., "SAO Type Coding Simplification", Joint Collaborative Team on Video Coding (JCT-VC) of ITU-T SG16 WP3 and ISO/IEC JTC1/SC29/WG11 JCTVC-I0246, ITU-T, Apr. 28, 2012, pp. 1-4.
Chih-Wei Hsu et at, "Non-CE1: Decoupling SAO on/off from SAO type with neighbor-based contexts", Joint Collaborative Team on Video Coding (JCT-VC) of ITU-T SG16 WP3 and ISO/IEC JTC1/SC29/WG11 JCTVC-I0199, ITU-T, Apr. 27, 2012, pp. 1-5.
Benjamin Bross et al, "High efficiency video coding (HEVC) text specification 7", Joint Collaborative Team on Video Coding (JCT-VC) of ITU-T SG16 WP3 and ISO/IEC JTC1/SC29/WG11 JCTVCI1003_d1, ITU-T, May 16, 2012, pp. 45, 174-175.
International Search Report dated Aug. 27, 2013 in International (PCT) Application No. PCT/JP2013/003452.
International Search Report dated Sep. 10, 2013 in International (PCT) Application No. PCT/JP2013/003635.
Koohyar Minoo et al., "CE1 Test 6.2: Coding of SAO Type", Joint Collaborative Team on Video Coding (JCT-VC) of ITU-T SG16 WP3 and ISO/IEC JTC1/SC29/WG11 JCTVC-I0379, ITU-T, Apr. 17, 2012, p. 1-4.
Benjamin Bross et al., "High efficiency video coding (HEVC) text specification draft 7", Joint Collaborative Team on Video Coding (JCT-VC) of ITU-T SG16 WP3 and ISO/IEC JTC1/SC29/WG11, JCTVC-I1003_d4, Ver. 5, 9th Meeting: Geneva, CH, Apr. 27-May 7, 2012.
Extended European Search Report dated Mar. 18, 2016 in European Application No. 13802843.6.
Extended European Search Report dated Apr. 13, 2016 in European Application No. 13800830.5.
Benjamin Bross et al., "High efficiency video coding (HEVC) text specification draft 7", Joint Collaborative Team on Video Coding (JCT-VC) of ITU-T SG16 WP3 and ISO/IEC JTC1/SC29/WG11, JCTVC-I1003_d0, 9th Meeting: Geneva, CH, Apr. 27-May 7, 2012, XP030112373.
Detlev Marpe et al., "Context-Based Adaptive Binary Arithmetic Coding in the H.264/AVC Video Compression Standard", IEEE Transactions on Circuits and Systems for Video Technology, vol. 13, No. 7, Jul. 1, 2003, pp. 620-636, XP 055120073.
Gary Sullivan et al., "Meeting report of the ninth meeting of the Joint Collaborative Team on Video Coding (JCT-VC), Geneva, CH, Apr. 27-May 7, 2012", Joint Collaborative Team on Video Coding (JCT-VC) of ITU-T SG16 WP3 and ISO/IEC JTC1/SC29/WG11, JCTVC-I_Notes_dD, 9th Meeting: Geneva, CH, Apr. 27-May 7, 2012, XP02711599, pp. 1-189.
In Suk Chong et al., "AHG6/AHG5: Fix and simplification for SAO type index", Joint Collaborative Team on Video Coding (JCT-VC) of ITU-T SG16 WP3 and ISO/IEC JTC1/SC29/WG11, JCTVC-J0104, 10th Meeting: Stockholm, SE, Jul. 11-20, 2012, XP030112466.
Joel Sole et al., "AhG6: Bypass bins grouping in SAO", Joint Collaborative Team on Video Coding (JCT-VC) of ITU-T SG16 WP3 and ISO/IEC JTC1/SC29/WG11, JCTVC-J0054, 10th Meeting: Stockholm, SE, Jul. 11-20, 2012, XP030112416.
Toru Matsunobu et al., "AHG5/AHG6: Bypass coding for SAO syntax elements", Joint Collaborative Team on Video Coding (JCT-VC) of ITU-T SG16 WP3 and ISO/IEC JTC1/SC29/WG11, JCTVC-J0148, 10th Meeting: Stockholm, Sweden, Jul. 11-20, 2012, XP030112510.
Chih-Ming Fu et al., "Non-CE1: Bug-fix of offset coding in SAO interleaving mode", Joint Collaborative Team on Video Coding (JCT-VC) of ITU-T SG16 WP3 and ISO/IEC JTC1/SC29/WG11, JCTVC-I0168, 9th Meeting: Geneva, CH, Apr. 27-May 7, 2012, XP030111931.
Office Action dated Jun. 21, 2016 in Taiwanese Patent Application No. 102119581, with English translation of Search Report.
Chih-Wei Hsu et al., "Non-CE1: Decoupling SAO on/off from SAO type with neighbor-based contexts", Joint Collaborative Team on Video Coding (JCT-VC) of ITU-T SG16 WP3 and ISO/IEC JTC1/SC29/WG11, JCTVC-I0199, ITU-T, Apr. 27, 2012, p. 1-6.
Patent Examination Report No. 1 dated Nov. 3, 2016 for the Australian Patent Application No. 2013272989.
Patent Examination Report No. 1 dated Nov. 7, 2016 for the Australian Patent Application No. 2013273686.
Office Action dated Feb. 10, 2017 in Australian Patent Application No. 2013272989.
Office Action dated Mar. 29, 2017 in Chinese Patent Application No. 201380002016.X, with English-language translation of Search Report.
Akira Minezawa et al., "Non-CE1: Improved edge offset coding for SA0", Joint Collaborative Team on Video Coding (JCT-VC) of ITU-T SG16 WP3 and ISO/IEC JTC1/SC29/WG11, JCTVC-I0066_r2, 9th Meeting: Geneva, CH, Apr. 27-May 7, 2012.
Office Action dated Apr. 20, 2017 in U.S. Appl. No. 15/008,738.
Office Action dated Oct. 10, 2017 in Philippine Patent Application No. 1-2013-502698.
E. Alshina et al., "AhG5: On bypass coding for SAO syntax elements", Joint Collaborative Team on Video Coding (JCT-VC) of ITU-T SG 16 WP 3 and ISO/IEC JTC 1/SC 29/WG 11, 10th Meeting: Stockholm, Sweden, Jul. 11-20, 2012, Jun. 26, 2012, JCTVC-J0043.doc, URL:http://phenix.it-sudparis.eu/jct/doc_end_user/documents/10_Stockholm/wg11/JCTVC-J0043-vl.zip.
Jun Xu et al., "AHG6: on SAO signalling", Joint Collaborative Team on Video Coding (JCT-VC) of ITU-T SG 16 WP 3 and ISO/IEC JTC 1/SC 29/WG 11, 10th Meeting: Stockholm, SE, Jul. 11-20, 2012, Jul. 14, 2012, JCTVC-J0268_r2.doc, URL:http://phenix.it-sudparis.eu/jct/doc_end_user/documents/10_Stockholm/wg11/JCTVC-J0268-v4.zip.
C. Rosewarne et al., "AHG5: On SAO syntax elements coding", Joint Collaborative Team on Video Coding (JCT-VC) of ITU-T SG 16 WP 3 and ISO/IEC JTC 1/SC 29/WG 11, 10th Meeting: Stockholm, SE, Jul. 11-20, 2012, Jul. 13, 2012, JCTVC-J0178.doc, URL:http://phenix.it-sudparis.eu/jct/doc_end_user/documents/10_Stockholm/wg11/JCTVC-J0178-v3.zip.
Toru Matsunobu et al., "AHG5/AHG6: Bypass coding for SAO syntax elements", Joint Collaborative Team on Video Coding (JCT-VC) of ITU-T SG 16 WP 3 and ISO/IEC JTC 1/SC 29/WG 11, 10th Meeting: Stockholm, Sweden, Jul. 11-20, 2012, Jul. 11, 2012, JCTVC-J0148r1.doc, URL:http://phenix.it-sudparis.eu/jct/doc_end_user/documents/10_Stockholm/wg11/JCTVC-J0148-v3.zip.
In Suk Chong et al., "AHG6/AHG5: Simplified SAO coding", Joint Collaborative Team on Video Coding (JCT-VC) of ITU-T SG 16 WP 3 and ISO/IEC JTC 1/SC 29/WG 11, 10th Meeting: Stockholm, SE, Jul. 11-20, 2012, Jul. 9, 2012, JCTVC-J0347-v3.doc, URL:http://phenix.it-sudparis.eu/jct/doc_end_user/documents/10_Stockholm/wg11/JCTVC-J0347-v4.zip.
B. Bross, et al., "High Efficiency Video Coding (HEVC) text specification draft 10 (for FDIS & Last Call)", JCT-VC of ITU-T and ISO/IEC, JCTVC-L1003 Ver. 34. Mar. 19, 2013, pp. 1-298.
Office Action dated Dec. 13, 2018 in Indian Patent Application No. 10262/CHENP/2013.
Wei-Jung Chien et al., "Intra mode coding for INTRA_NxN", Joint Collaborative Team on Video Coding (JCT-VC) of ITU-T SG16 WP3 and ISO/IEC JTC1/SC29/WG11, 9th Meeting, Geneva, CH, Apr. 27-May 7, 2012, pp. 1-6.

(56) References Cited

OTHER PUBLICATIONS

Office Action dated Aug. 30, 2019 in Indian Patent Application No. 10226/CHENP/2013.
Office Action dated Dec. 12, 2019 in European Patent Application No. 13 802 843.6.

* cited by examiner

| Class | Condition | Edge shape |
|---|---|---|
| 1 | c < c1 && c < c2 | |
| 2 | (c < c1 && c == c2) \|\| (c == c1 && c < c2) | |
| 3 | (c > c1 && c == c2) \|\| (c == c1 && c > c2) | |
| 4 | c > c1 && c > c2 | |
| 0 | None of the above | |

| Class | Conditions | Class | Conditions |
|---|---|---|---|
| 1 | $R0 \leq c < R1$ | 9 | $R8 \leq c < R9$ |
| 2 | $R1 \leq c < R2$ | 10 | $R9 \leq c < R10$ |
| 3 | $R2 \leq c < R3$ | 11 | $R10 \leq c < R11$ |
| 4 | $R3 \leq c < R4$ | 12 | $R11 \leq c < R12$ |
| 5 | $R4 \leq c < R5$ | 13 | $R12 \leq c < R13$ |
| 6 | $R5 \leq c < R6$ | 14 | $R13 \leq c < R14$ |
| 7 | $R6 \leq c < R7$ | 15 | $R14 \leq c < R15$ |
| 8 | $R7 \leq c < R8$ | 16 | $R15 \leq c \leq R16$ |

Code this category index number

| Index | Bit allocation | Pixel classifying method |
|---|---|---|
| 0 | 0 | Do not perform offset processing |
| 1 | 10 | Edge offset (0) |
| 2 | 110 | Edge offset (1) |
| 3 | 1110 | Edge offset (2) |
| 4 | 11110 | Edge offset (3) |
| 5 | 11111 | Band offset |

FIG. 16A

| aps_sao_param(){ | Descriptor |
|---|---|
|   sao_cb_enable_flag | u(1) |
|   sao_cr_enable_flag | u(1) |
|   sao_num_lcu_in_width_minus1 | ue(v) |
|   sao_num_lcu_in_height_minus1 | ue(v) |
|   sao_one_luma_unit_flag | u(1) |
|   if(sao_one_luma_unit_flag) | |
|     sao_offset_vlc(0, 0, 0) | |
|   if(sao_cb_enable_flag){ | |
|     sao_one_cb_unit_flag | u(1) |
|     if(sao_one_cb_unit_flag) | |
|       sao_offset_vlc(0, 0, 1) | |
|   } | |
|   if(sao_cr_enable_flag){ | |
|     sao_one_cr_unit_flag | u(1) |
|     if(sao_one_cr_unit_flag) | |
|       sao_offset_vlc(0, 0, 2) | |
|   } | |
|   for(ry = 0; ry <= sao_num_lcu_in_height_minus1; ry++){ | |
|     for(rx = 0; rx <= sao_num_lcu_in_width_minus1; rx++){ | |
|       if(aps_sample_adaptive_offset_flag && !sao_one_luma_unit_flag){ | |
|         if(ry > 0 && rx == 0) | |
|           sao_repeat_row_flag[0] | u(1) |
|         sao_unit_vlc(rx, ry, 0) | |
|       } | |
|       if(sao_cb_enable_flag && !sao_one_cb_unit_flag){ | |
|         if(ry > 0 && rx == 0) | |
|           sao_repeat_row_flag[1] | u(1) |
|         sao_unit_vlc(rx, ry, 1) | |
|       } | |
|       if(sao_cr_enable_flag && !sao_one_cr_unit_flag){ | |
|         if(ry > 0 && rx == 0) | |
|           sao_repeat_row_flag[2] | u(1) |
|         sao_unit_vlc(rx, ry, 2) | |
|       } | |
|     } | |

FIG. 16B

| | Descriptor |
|---|---|
| sao_unit_vlc(rx, ry, cIdx){ | |
|   if(!sao_repeat_row_flag[ cIdx ]){ | |
|     if(rx == 0 \|\| run[ cIdx ][ rx ][ ry ] < 0) | |
|       if(ry == 0){ | |
|         sao_run_diff | u(v) |
|         saoRun[ cIdx ][ rx ][ ry ] = sao_run_diff | |
|       } else { | |
|         sao_run_diff | se(v) |
|         saoRun[ cIdx ][ rx ][ ry ] = sao_run_diff + saoRun[ cIdx ][ rx ][ ry - 1 ] | |
|       } | |
|     saoRun[ cIdx ][ rx + 1 ][ ry ] = saoRun[ cIdx ][ rx ][ ry ] - 1 | |
|     if(rx == 0 \|\| saoRun[ cIdx ][ rx ][ ry ] < 0) | |
|       if( ry > 0) | |
|         sao_merge_up_flag | u(1) |
|       if(!sao_merge_up_flag) | |
|         sao_offset_vlc(rx, ry, cIdx) | |
|   } else | |
|     saoRun[ cIdx ][ rx ][ ry ] = saoRun[ cIdx ][ rx ][ ry - 1 ] | |
| } | |

FIG. 16C

| | Descriptor |
|---|---|
| sao_offset_vlc(rx, ry, cIdx){ | |
|   sao_type_idx[ cIdx ][ rx ][ ry ] | ue(v) |
|   if(sao_type_idx[ cIdx ][ rx ][ ry ] == 5){ | |
|     sao_band_position[ cIdx ][ rx ][ ry ] | u(5) |
|     for(i = 0; i < 4; i++) | |
|       sao_offset[ cIdx ][ rx ][ ry ][ i ] | se(v) |
|   } else if(sao_type_idx[ cIdx ][ rx ][ ry ] != 0) | |
|     for(i = 0; i < 4; i++) | |
|       sao_offset[ cIdx ][ rx ][ ry ][ i ] | ue(v) |
| } | |

FIG. 17A

| slice_data(){ | Descriptor |
|---|---|
|   CtbAddrRS = SliceCtbAddrRS | |
|   CtbAddrTs = CtbAddrRStoTS[ CtbAddrRs ] | |
|   moreDataFlag = 1 | |
|   if( adaptive_loop_filter_flag && alf_cu_control_flag ) | |
|     AlfCuFlagIdx = -1 | |
|   do { | |
|     xCtb = InverseRasterScan( CtbAddrRS, CtbSize, CtbSize,<br>      pic_width_in_luma_samples, 0 ) | |
|     yCtb = InverseRasterScan( CtbAddrRS, CtbSize, CtbSize,<br>      pic_width_in_luma_samples, 1 ) | |
|     NumPCMBlock = 0 | |
|     CtbAddrInSlice = CtbAddrRS - ( slice_address >> SliceGranularity ) | |
|     AddrUp = CtbAddrRS - PicWidthInCtbs | |
|     if( slice_sao_interleaving_flag ){ | |
|       if(slice_sample_adaptive_offset_flag) | |
|         sao_unit_cabac( xCtb, yCtb, 0 ) | |
|       if(sao_cb_enable_flag) | |
|         sao_unit_cabac( xCtb, yCtb, 1 ) | |
|       if(sao_cr_enable_flag) | |
|         sao_unit_cabac( xCtb, yCtb, 2 ) | |
|     } | |
|     moreDataFlag = coding_tree( xCtb, yCtb, Log2CtbSize, 0 ) | |
|     CtbAddrTS++ | |
|     if( moreDataFlag && ((tiles_or_entropy_coding_sync_idc == 1 &&<br>      TileId[ CtbAddrTS ] ! = TileId[ CtbAddrTS - 1 ]) \|\|<br>      (tiles_or_entropy_coding_sync_idc == 2 &&<br>        num_substream_minus1 > 0 &&<br>        CtbAddrTs/PicWidthInCtbs <= num_substream_minus1 &&<br>        CtbAddrTS % PicWidthInCtbs == 0))){ | |
|       rbsp_trailing_bits() | |
|       if(nextbits(24) == 0x000002){ | |
|         entry_point_marker_two_3bytes | f(24) |
|         tile_idx_minus_1 | u(v) |
|       } | |
|     } | |
|   } while( moreDataFlag ) | |
| } | |

FIG. 17B

| sao_unit_cabac( rx, ry, cIdx ){ | Descriptor |
|---|---|
| if( rx > 0 ) { | |
|   if(CtbAddrInSlice!=0 && | |
|     TileId[ CtbAddrTS ] == TileId[ CtbAddrRStoTS[ CtbAddrRS - 1 ] ] ) | |
|     sao_merge_left_flag | ae(v) |
| } | |
| if( !sao_merge_left_flag ) { | |
|   if( ry > 0 ) { | |
|     if(((CtbAddrTS - CtbAddrRStoTS[CtbAddrRS-PicWidthInCtbs]) | |
|       <=CtbAddrInSlice) && | |
|       (TileId[ CtbAddrTS ]== | |
|         TileId[ CtbAddrRStoTS[ CtbAddrRS- PicWidthInCtbs ] ] ) ) | |
|     sao_merge_up_flag | ae(v) |
|   } | |
|   if( !sao_merge_up_flag ) | |
|     sao_offset_cabac( rx, ry, cIdx ) | |
| } | |
| } | |

FIG. 17C

| sao_offset_cabac( rx, ry, cIdx ) { | Descriptor |
|---|---|
|   sao_type_idx[ cIdx ][ rx ][ ry ] | ae(v) |
|   if( sao_type_idx[ cIdx ][ rx ][ ry ] == 5 ) | |
|     sao_band_position[ cIdx ][ rx ][ ry ] | ae(v) |
|   if( sao_type_idx[ cIdx ][ rx ][ ry ] != 0 ) { | |
|     for( i = 0; i < 4; i++ ) | |
|       sao_offset[ cIdx ][ rx ][ ry ][ i ] | ae(v) |
|   } | |
|   if( sao_type_idx[ cIdx ][ rx ][ ry ] == 5 ) { | |
|     for( i = 0; i < 4; i++ ) { | |
|       if( sao_offset[ cIdx ][ rx ][ ry ] != 0 ) | |
|         sao_offset_sign[ cIdx ][ rx ][ ry ][ i ] | ae(v) |
|     } | |
|   } | |
| } | |

FIG. 25

| Index | Bit allocation | Pixel classifying method |
|---|---|---|
| 0 | 0 | No offset processing |
| 1 | 10 | Band offset |
| 2 | 110 | Edge offset (0) |
| 3 | 1110 | Edge offset (1) |
| 4 | 11110 | Edge offset (2) |
| 5 | 11111 | Edge offset (3) |

FIG. 26

| Index | Bit allocation | Offset processing flag |
|---|---|---|
| 0 | 0 | Do not perform offset processing |
| 1 | 1 | Perform offset processing |

| Index | Bit allocation | Pixel classifying method |
|---|---|---|
| 0 | 0 | Band offset |
| 1 | 10 | Edge offset (0) |
| 2 | 110 | Edge offset (1) |
| 3 | 1110 | Edge offset (2) |
| 4 | 1111 | Edge offset (3) |

FIG. 27A

| sao_unit_vlc( rx, ry, cIdx ) { | Descriptor |
|---|---|
| if( !sao_repeat_row_flag[ cIdx ] ) { | |
| if( rx == 0 \|\| run[ cIdx ][ rx ][ ry ] < 0 ) | |
| if( ry == 0 ) { | |
| sao_run_diff | u(v) |
| saoRun[ cIdx ][ rx ][ ry ] = sao_run_diff | |
| } else { | |
| sao_run_diff | se(v) |
| saoRun[ cIdx ][ rx ][ ry ] = sao_run_diff + saoRun[ cIdx ][ rx ][ ry - 1 ] | |
| } | |
| saoRun[ cIdx ][ rx + 1 ][ ry ] = saoRun[ cIdx ][ rx ][ ry ] - 1 | |
| if( rx == 0 \|\| saoRun[ cIdx ][ rx ][ ry ] < 0) | |
| sao_on_flag ⎯⎯⎯ Offset processing flag | u(1) |
| if ( sao_on_flag ) { | |
| if ( ry > 0 ) | |
| sao_merge_up_flag | u(1) |
| if( !sao_merge_up_flag ) | |
| sao_offset_vlc( rx, ry, cIdx) | |
| } | |
| } else | |
| saoRun[ cIdx ][ rx ][ ry ] = saoRun[ cIdx ][ rx ][ ry - 1 ] | |
| } | |

FIG. 27B

| sao_offset_vlc( rx, ry, cIdx ) {              Pixel classifying | Descriptor |
|---|---|
| sao_type_idx [ cIdx ][ rx ][ ry ] ⎯⎯⎯ method | ue(v) |
| if( sao_type_idx[ cIdx ][ rx ][ ry ] == 5 ) {   Index number | |
| sao_band_position [ cIdx ][ rx ][ ry ] | u(5) |
| for( i = 0; i < 4; i++ ) | |
| sao_band_offset [ cIdx ][ rx ][ ry ][ i ] | se(v) |
| } else | |
| for( i = 0; i < 4; i++ ) | |
| sao_edge_offset [ cIdx ][ rx ][ ry ][ i ] | ue(v) |
| } | |

| Syntax element | ctxIdxTable, ctxIdxOffset | binIdx | | | | |
|---|---|---|---|---|---|---|
| | | 0 | 1 | 2 | 3 | >= 4 |
| sao_on_flag | Table 9-5' | 0 cIdx | na | na | na | na |
| | | 3 cIdx | na | na | na | na |
| | | 6 cIdx | na | na | na | na |

FIG. 28A

| sao_unit_cabac( rx, ry, cIdx ){ | Descriptor |
|---|---|
| sao_on_flag ———⌒——— Offset processing flag | u(1) |
| if(sao_on_flag) { | |
|   if( rx > 0 ) { | |
|     if(CtbAddrInSlice!=0 && | |
|       TileId[ CtbAddrTS ] == TileId[ CtbAddrRStoTS[ CtbAddrRS - 1 ] ] ) | |
|     sao_merge_left_flag | ae(v) |
|   } | |
|   if( !sao_merge_left_flag ) { | |
|     if( ry > 0 ) { | |
|       if(((CtbAddrTS - CtbAddrRStoTS[CtbAddrRS-PicWidthInCtbs]) | |
|         <=CtbAddrInSlice) && | |
|       (TileId[ CtbAddrTS ]== | |
|         TileId[ CtbAddrRStoTS[ CtbAddrRS- PicWidthInCtbs ] ] ) ) | |
|     sao_merge_up_flag | ae(v) |
|     } | |
|     if( !sao_merge_up_flag ) | |
|       sao_offset_cabac( rx, ry, cIdx ) | |
|     } | |
|   } | |
| } | |

FIG. 28B

| sao_offset_cabac( rx, ry, cIdx ) { | Descriptor |
|---|---|
| sao_type_idx [ cIdx ][ rx ][ ry ]  ——⌒—— Index number / Pixel classifying method | ae(v) |
| if( sao_type_idx[ cIdx ][ rx ][ ry ] != 0 ) { | |
|   for( i = 0; i < 4; i++ ) | |
|     sao_offset [ cIdx ][ rx ][ ry ][ i ] | ae(v) |
|   } | |
|   if( sao_type_idx[ cIdx ][ rx ][ ry ] == 5 ) { | |
|     for( i = 0; i < 4; i++ ) { | |
|       if( sao_offset[ cIdx ][ rx ][ ry ] ! = 0 ) | |
|         sao_offset_sign [ cIdx ][ rx ][ ry ][ i ] | ae(v) |
|     } | |
|     sao_band_position [ cIdx ][ rx ][ ry ] | ae(v) |
|   } | |
| } | |

FIG. 28C

| Syntax element | ctxIdxTable, ctxIdxOffset | binIdx | | | | | |
|---|---|---|---|---|---|---|---|
| | | | 0 | 1 | 2 | 3 | >=4 |
| sao_on_flag | Table 9-5' | 0 | cIdx | na | na | na | na |
| | | 3 | cIdx | na | na | na | na |
| | | 6 | cIdx | na | na | na | na |
| sao_merge_left_flag | Table 9-5 | 0 | cIdx | na | na | na | na |
| | | 3 | cIdx | na | na | na | na |
| | | 6 | cIdx | na | na | na | na |
| sao_merge_up_flag | Table 9-6 | 0 | 0 | na | na | na | na |
| | | 1 | 0 | na | na | na | na |
| | | 2 | 0 | na | na | na | na |
| sao_type_idx | Table 9-7 | 0 | 0 | 1 | 1 | 1 | 1 |
| | | 2 | 0 | 1 | 1 | 1 | 1 |
| | | 4 | 0 | 1 | 1 | 1 | 1 |
| sao_offset | Table 9-8 | 0 | 0 | 1 | 1 | 1 | 1 |
| | | 2 | 0 | 1 | 1 | 1 | 1 |
| | | 4 | 0 | 1 | 1 | 1 | 1 |
| sao_offset_sign | na | na | na(uses Decode Bypass) | na | na | na | na |
| | | na | na(uses Decode Bypass) | na | na | na | na |
| | | na | na(uses Decode Bypass) | na | na | na | na |
| sao_band_position | na | na | na(uses Decode Bypass) | na | na | na | na |
| | | na | na(uses Decode Bypass) | na | na | na | na |
| | | na | na(uses Decode Bypass) | na | na | na | na |

FIG. 31A

| Syntax element | ctxIdxTable, ctxIdxOffset | binIdx | | | | | |
|---|---|---|---|---|---|---|---|
| | | | 0 | 1 | 2 | 3 | >=4 |
| sao_on_flag | Table 9-X | 0 | 0 | na | na | na | na |
| | | 1 | 0 | na | na | na | na |
| | | 2 | 0 | na | na | na | na |
| sao_merge_left_flag | Table 9-XX | 0 | 0 | na | na | na | na |
| | | 1 | 0 | na | na | na | na |
| | | 2 | 0 | na | na | na | na |
| sao_merge_up_flag | Table 9-XXX | 0 | 0 | na | na | na | na |
| | | 1 | 0 | na | na | na | na |
| | | 2 | 0 | na | na | na | na |
| sao_type_idx | na | na | na(uses Decode Bypass) | na | na | na | na |
| | | na | na(uses Decode Bypass) | na | na | na | na |
| | | na | na(uses Decode Bypass) | na | na | na | na |
| sao_offset | na | na | na(uses Decode Bypass) | na | na | na | na |
| | | na | na(uses Decode Bypass) | na | na | na | na |
| | | na | na(uses Decode Bypass) | na | na | na | na |
| sao_offset_sign | na | na | na(uses Decode Bypass) | na | na | na | na |
| | | na | na(uses Decode Bypass) | na | na | na | na |
| | | na | na(uses Decode Bypass) | na | na | na | na |
| sao_band_position | na | na | na(uses Decode Bypass) | na | na | na | na |
| | | na | na(uses Decode Bypass) | na | na | na | na |
| | | na | na(uses Decode Bypass) | na | na | na | na |

FIG. 31B

| Configuration | BD-rate |
|---|---|
| All Intra Main | 0.1 % |
| Random Access Main | 0.0 % |
| Low Delay B Main | 0.0 % |
| All Intra HE10 | 0.1 % |
| Random Access HE10 | -0.1 % |
| Low delay B HE10 | 0.0 % |

FIG. 44

| |
|---|
| Video stream (PID=0x1011, Primary video) |
| Audio stream (PID=0x1100) |
| Audio stream (PID=0x1101) |
| Presentation graphics stream (PID=0x1200) |
| Presentation graphics stream (PID=0x1201) |
| Interactive graphics stream (PID=0x1400) |
| Video stream (PID=0x1B00, Secondary video) |
| Video stream (PID=0x1B01, Secondary video) |

FIG. 55

| Corresponding standard | Driving frequency |
|---|---|
| MPEG-4 AVC | 500 MHz |
| MPEG-2 | 350 MHz |
| ⋮ | ⋮ |

ARITHMETIC CODING FOR INFORMATION RELATED TO SAMPLE ADAPTIVE OFFSET PROCESSING

FIELD

The present disclosure relates to an image coding method using arithmetic coding.

BACKGROUND

There are techniques described in Non Patent Literature (NPL) 1 and NPL 2 which relate to the image coding method using arithmetic coding.

CITATION LIST

Non Patent Literature

[NPL 1]
ISO/IEC 14496-10 "MPEG-4 Part 10 Advanced Video Coding"
[NPL 2]
Frank Bossen, "Common test conditions and software reference configurations", JCTVC-H1100, Joint Collaborative Team on Video Coding (JCT-VC) of ITU-T SG16 WP3 and ISO/IEC JTC1/SC29/WG11 8th Meeting, San Jose, Calif., USA, 1-10 Feb. 2012.

SUMMARY

Technical Problem

However, when coding is performed with poor processing efficiency, it is difficult to suppress processing delay that occurs during the coding.

In view of the above, one non-limiting and exemplary embodiment provides an image coding method which allows coding with high coding efficiency.

Solution to Problem

An image coding method according to an aspect of the present disclosure includes: performing context arithmetic coding to consecutively code (i) first information indicating whether or not to perform sample adaptive offset (SAO) processing for a first region of an image and (ii) second information indicating whether or not to use, in the SAO processing for the first region, information on SAO processing for a region other than the first region, the context arithmetic coding being arithmetic coding using a variable probability, the SAO processing being offset processing on a pixel value; and performing bypass arithmetic coding to code other information which is information on the SAO processing for the first region and different from the first information or the second information, after the first information and the second information are coded, the bypass arithmetic coding being arithmetic coding using a fixed probability.

It is to be noted that general and specific aspects disclosed above may be implemented using a system, an apparatus, an integrated circuit, a computer program, or a non-transitory computer-readable recording medium such as a CD-ROM, or any combination of systems, apparatuses, methods, integrated circuits, computer programs, or recording media.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

An image coding method according to the present disclosure allows coding with high coding efficiency.

BRIEF DESCRIPTION OF DRAWINGS

These and other objects, advantages and features of the disclosure will become apparent from the following description thereof taken in conjunction with the accompanying drawings that illustrate a specific embodiment of the present disclosure.

FIG. 16A is a schematic view which illustrates an example of syntax (aps_sao_param) in APS according to Embodiment 1.

FIG. 16B is a schematic view which illustrates an example of syntax (sao_unit_vlc) in APS according to Embodiment 1.

FIG. 16C is a schematic view which illustrates an example of syntax (sao_offset_vlc) in APS according to Embodiment 1.

FIG. 17A is a schematic view which illustrates an example of syntax (slice_data) in slice data according to Embodiment 1.

FIG. 17B is a schematic view which illustrates an example of syntax (sao_unit_cabac) in slice data according to Embodiment 1.

FIG. 17C is a schematic view which illustrates an example of syntax (sao_offset_cabac) in slice data according to Embodiment 1.

FIG. 25 is a schematic view which illustrates an example of bit allocation to index numbers each indicating a pixel classifying method according to Embodiment 2.

FIG. 26 is a schematic view which illustrates another example of bit allocation to index numbers each indicating a pixel classifying method according to Embodiment 2.

FIG. 27A is a schematic view which illustrates an example of syntax (sao_unit_vlc) in APS according to Embodiment 2.

FIG. 27B is a schematic view which illustrates an example of syntax (sao_offset_vlc) in APS according to Embodiment 2.

FIG. 28A is a schematic view which illustrates an example of syntax (sao_unit_cabac) in slice data according to Embodiment 2.

FIG. 28B is a schematic view which illustrates an example of syntax (sao_offset_cabac) in slice data according to Embodiment 2.

FIG. 28C is a schematic view which illustrates an example of allocation of a context index to offset information in slice data according to Embodiment 2.

FIG. 31A is a schematic view which illustrates an example of allocation of a context index to offset information according to Embodiment 3.

FIG. 31B is a diagram which shows an objective performance of an image coding apparatus and an image decoding apparatus according to Embodiment 3.

FIG. 44 illustrates a structure of multiplexed data.

FIG. 55 shows an example of a look-up table in which video data standards are associated with driving frequencies.

Figure 1:
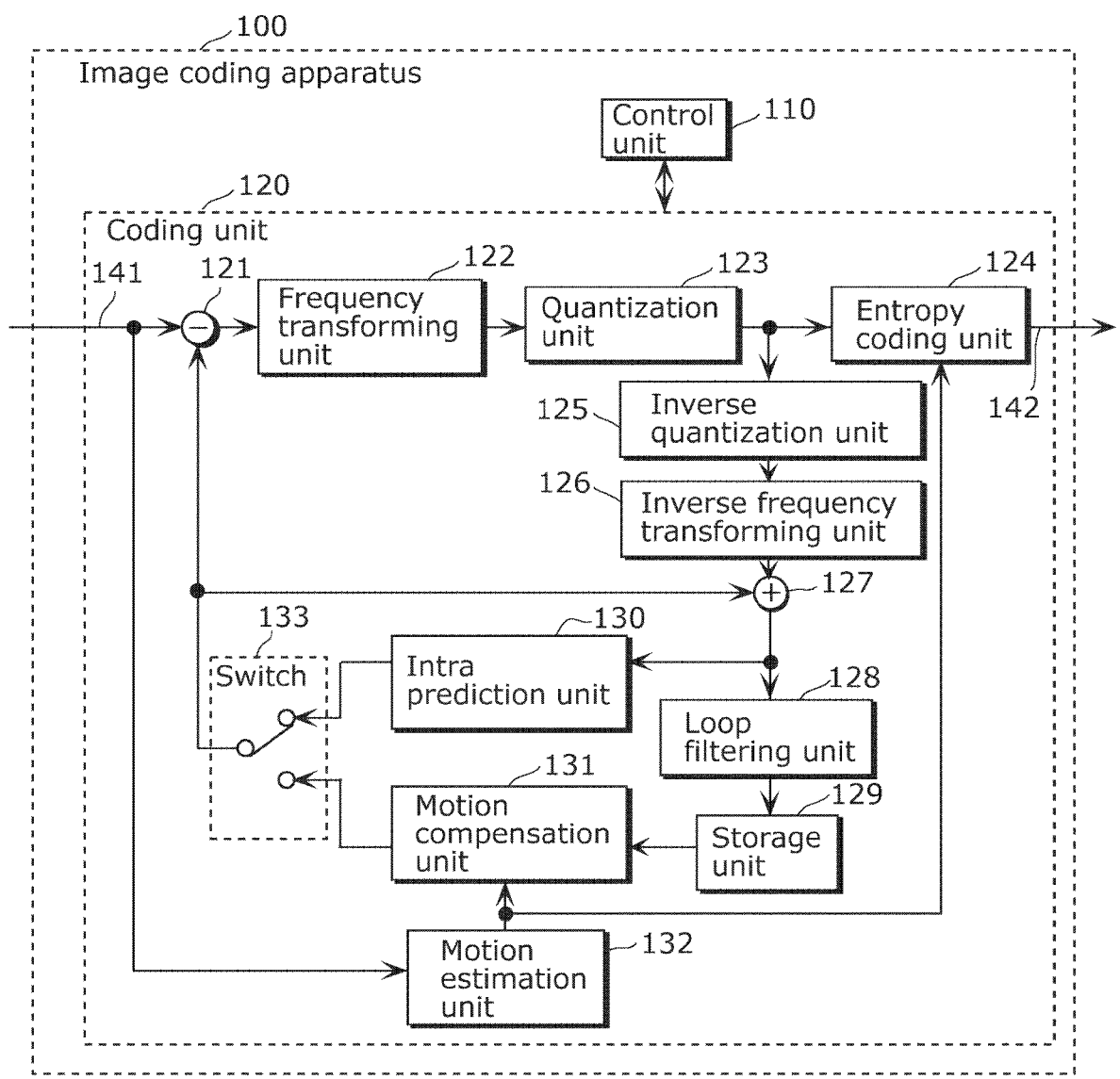
FIG. 1 is a block diagram which illustrates an example of a configuration of an image coding apparatus according to Embodiment 1.

DESCRIPTION OF EMBODIMENTS (Underlying Knowledge Forming Basis of the Present Disclosure)

The inventors have found a problem in the image coding method using arithmetic coding which is described in "Background". The following describes the details.

An image coding apparatus according to an image coding system represented by the ITU-T standard called H.26x and the ISO/IEC standard called MPEG-x divides a picture into predetermined units and performs coding by the unit. For example, an image coding apparatus according to the H.264/MPEG-4 AVC standard (see Non Patent Literature (NPL) 1), performs a process by a unit called a macroblock having 16 horizontal pixels and 16 vertical pixels.

The image coding apparatus divides the macroblock into sub blocks (each having at least 4 horizontal pixels and 4 vertical pixels), when performing motion compensation. The image coding apparatus performs motion compensation using a motion vector that is different for each of the sub blocks, performs frequency transformation on a difference signal between an original signal and a prediction signal, collects information on the difference signal in a low-frequency region, and performs quantization, thereby compressing information.

It is known that grid-like distortion called block distortion appears at a boundary of blocks according to a method for coding a picture on a block-by-block basis using orthogonal transformation such as DCT which collects information on a difference signal in a low-frequency region. The image coding apparatus is capable of reducing the block distortion by performing deblocking filtering processing.

However, with the system which processes only the block boundary as with the above-described deblocking filter, there is difficulty in reducing coding deterioration other than the block distortion.

In view of the above, an image coding method according to an aspect of the present disclosure includes: performing context arithmetic coding to consecutively code (i) first information indicating whether or not to perform sample adaptive offset (SAO) processing for a first region of an image and (ii) second information indicating whether or not to use, in the SAO processing for the first region, information on SAO processing for a region other than the first region, the context arithmetic coding being arithmetic coding using a variable probability, the SAO processing being offset processing on a pixel value; and performing bypass arithmetic coding to code other information which is information on the SAO processing for the first region and different from the first information or the second information, after the first information and the second information are coded, the bypass arithmetic coding being arithmetic coding using a fixed probability.

With this, the context arithmetic coding is consecutively performed on the information on SAO processing for improving an image quality. More specifically, frequent switching between the context arithmetic coding and the bypass arithmetic coding is suppressed and processes of the same type are consecutively performed. Thus, the processing efficiency improves.

For example, in the performing of bypass arithmetic coding, the other information may be coded which includes (i) third information indicating whether the SAO processing for the first region is edge offset processing or band offset processing and (ii) fourth information indicating an absolute value of an offset value, the edge offset processing being performed according to an edge, the band offset processing being performed according to a pixel value.

With this, a variety of information items are coded by the bypass arithmetic coding after the context arithmetic coding. In sum, processes of the same type are collectively performed. Thus, the processing efficiency improves.

In addition, for example, in the performing of bypass arithmetic coding, when the SAO processing for the first region is the band offset processing, the other information may be coded which includes (i) fifth information indicating whether the offset value is positive or negative and (ii) sixth information indicating a scope of application of the offset value.

With this, a further variety of information items are coded by the bypass arithmetic coding according to the state, after the context arithmetic coding. Thus, the processing efficiency improves.

In addition, for example, in the performing of context arithmetic coding, the second information may be coded which includes at least one of (i) information indicating whether or not information on SAO processing for a left region is used in the SAO processing for the first region and (ii) information indicating whether or not information on SAO processing for an upper region is used in the SAO processing for the first region, the left region being adjacent to the first region and being to the left of the first region, the upper region being adjacent to the first region and being on top of the first region.

With this, in the context arithmetic coding that is consecutively performed, information indicating the reuse from above or left is properly coded.

In addition, an image decoding method according to an aspect of the present disclosure may be an image decoding method which includes: performing context arithmetic decoding to consecutively decode (i) first information indicating whether or not to perform sample adaptive offset (SAO) processing for a first region of an image and (ii) second information indicating whether or not to use, in the SAO processing for the first region, information on SAO processing for a region other than the first region, the context arithmetic decoding being arithmetic decoding using a variable probability, the SAO processing being offset processing on a pixel value; and performing bypass arithmetic decoding to decode other information which is information on the SAO processing for the first region and different from the first information or the second information, after the first information and the second information are decoded, the bypass arithmetic decoding being arithmetic decoding using a fixed probability.

With this, the context arithmetic decoding is consecutively performed on the information on SAO processing for improving an image quality. More specifically, frequent switching between the context arithmetic decoding and the bypass arithmetic decoding is suppressed and processes of the same type are consecutively performed. Thus, the processing efficiency improves.

For example, in the performing of bypass arithmetic decoding, the other information may be decoded which includes (i) third information indicating whether the SAO processing for the first region is edge offset processing or band offset processing and (ii) fourth information indicating an absolute value of an offset value, the edge offset processing being performed according to an edge, the band offset processing being performed according to a pixel value.

With this, a variety of information items are decoded by the bypass arithmetic decoding after the context arithmetic decoding. In sum, processes of the same type are collectively performed. Thus, the processing efficiency improves.

In addition, for example, in the performing of bypass arithmetic decoding, when the SAO processing for the first region is the band offset processing, the other information may be decoded which includes (i) fifth information indicating whether the offset value is positive or negative and (ii) sixth information indicating a scope of application of the offset value.

With this, a further variety of information items are decoded by the bypass arithmetic decoding according to the state after the context arithmetic decoding. Thus, the processing efficiency improves.

In addition, for example, in the performing of context arithmetic decoding, the second information may be decoded which includes at least one of (i) information indicating whether or not information on SAO processing for a left region is used in the SAO processing for the first region and (ii) information indicating whether or not information on SAO processing for an upper region is used in the SAO processing for the first region, the left region being adjacent to the first region and being to the left of the first region, the upper region being adjacent to the first region and being on top of the first region.

With this, in the context arithmetic decoding that is consecutively performed, information indicating the reuse from above or left in the context arithmetic decoding is properly decoded.

It is to be noted that general and specific aspects disclosed above may be implemented using a system, an apparatus, an integrated circuit, a computer program, or a non-transitory computer-readable recording medium such as a CD-ROM, or any combination of systems, apparatuses, methods integrated circuits, computer programs, or recording media.

The following describes embodiments in detail with reference to the drawings. It is to be noted that each of the embodiments described below shows a general or specific example. The numerical values, shapes, materials, structural elements, the arrangement and connection of the structural elements, steps, the processing order of the steps etc. shown in the following embodiments are mere examples, and therefore do not limit the scope of the Claims. Therefore, among the structural elements in the following embodiments, structural elements not recited in any one of the independent claims are described as arbitrary structural elements.

In addition, the term "coding" in the following description may be used to mean "encoding".

Embodiment 1

FIG. 1 illustrates a configuration of an image coding apparatus according to Embodiment 1. An image coding apparatus 100 illustrated in FIG. 1 includes a control unit 110 and a coding unit 120. The coding unit 120 includes: a subtractor 121; a frequency transforming unit 122; a quantization unit 123; an entropy coding unit 124; an inverse quantization unit 125; an inverse frequency transforming unit 126; an adder 127; a loop filtering unit 128; a storage unit 129; an intra prediction unit 130; a motion compensation unit 131; a motion estimation unit 132; and a switch 133.

The coding unit 120 codes an image 141 on a block-by-block basis to generate a coded stream 142. At this time, the subtractor 121 in the coding unit 120 subtracts a pixel block having plural pixel values of a prediction image, from a pixel block having plural pixel values of the image 141. The frequency transforming unit 122 transforms a pixel block resulting from the subtraction into a coefficient block having plural frequency coefficients. The quantization unit 123 quantizes the coefficient block obtained from the frequency transforming unit 122.

Meanwhile, the motion estimation unit 132 detects a motion vector using the pixel block of the image 141. The motion compensation unit 131 performs inter picture prediction (inter prediction) using a reference image in the storage unit 129 and the motion vector detected by the motion estimation unit 132. The intra prediction unit 130 performs intra picture prediction (intra prediction) using the pixel block obtained from the adder 127, according to an intra prediction mode. The switch 133 inputs the pixel block of the prediction image resulting from the intra picture prediction or the inter picture prediction, to the subtractor 121 and the adder 127.

The entropy coding unit 124 performs entropy coding on partition information of a block, a type of prediction, a motion vector, a prediction mode (intra picture prediction mode), a quantization parameter, the quantized coefficient block, and so on, to generate the coded stream 142.

In addition, the inverse quantization unit 125 performs inverse quantization on the quantized coefficient block. In addition, the inverse frequency transforming unit 126 transforms the coefficient block on which inverse quantization is performed, into a pixel block. The adder 127 adds the pixel block of the prediction image to the pixel block obtained from the inverse frequency transforming unit 126. The loop filtering unit 128 suppresses distortion in the pixel block obtained in the adder 127, and stores the pixel block as a reference image in the storage unit 129.

Furthermore, the control unit 110 controls the coding unit 120. The image coding apparatus 100 codes the image 141 through the operation described above. In addition, the image coding apparatus 100 reduces a data amount of the coded stream 142 through a variety of processes such as frequency transformation, quantization, intra picture prediction, inter picture prediction, entropy coding, loop filtering, and so on.

Figure 2:
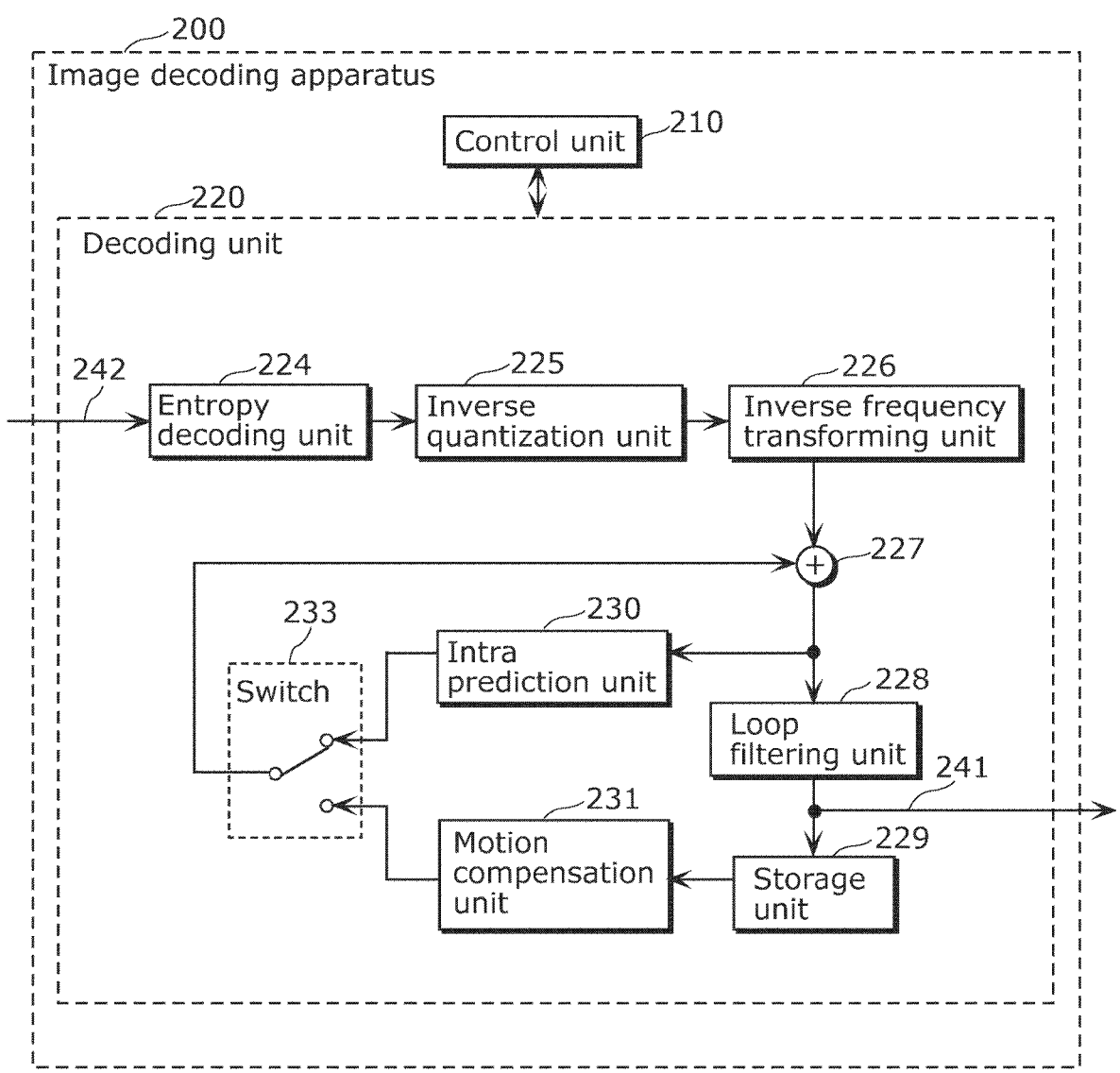
FIG. 2 is a block diagram which illustrates an example of a configuration of an image decoding apparatus according to Embodiment 1.

FIG. 2 illustrates a configuration of an image decoding apparatus 200 corresponding to the image coding apparatus 100 illustrated in FIG. 1. The image decoding apparatus 200 illustrated in FIG. 2 includes a control unit 210 and a decoding unit 220. The decoding unit 220 includes: an entropy decoding unit 224; an inverse quantization unit 225; an inverse frequency transforming unit 226; an adder 227; a loop filtering unit 228; a storage unit 229; an intra picture prediction unit 230; a motion compensation unit 231; and a switch 233.

The decoding unit 220 decodes, on a block-by-block basis, an image 241 included in a coded stream 242. At this time, the entropy decoding unit 224 in the decoding unit 220 performs entropy decoding on the coded stream 242, thereby obtaining partition information of a block, a type of prediction, a motion vector, an intra picture prediction mode, a quantization parameter, a quantized coefficient block, and so on.

Then, the control unit 210 controls operation performed by the decoding unit 220.

The inverse quantization unit 225 in the decoding unit 220 performs inverse quantization on the quantized coefficient block. The inverse frequency transforming unit 226 transforms the coefficient block on which inverse quantization is performed, into a pixel block.

The adder 227 adds the pixel block of the prediction image to the pixel block obtained from the inverse frequency transforming unit 226. The loop filtering unit 228 suppresses distortion in the pixel block obtained from the adder 227. Then, the loop filtering unit 228 stores a reference image including pixel blocks in the storage unit 229. Furthermore, the loop filtering unit 228 outputs an image 241 including pixel blocks.

When the type of prediction is intra picture prediction, the intra prediction unit 230 performs intra picture prediction using the pixel block obtained from the adder 227, according to an intra prediction mode. When the type of prediction is inter picture prediction, the motion compensation unit 231 performs inter picture prediction using the motion vector and the reference image in the storage unit 229. The switch 233 inputs the pixel block of the prediction image resulting from the intra picture prediction or the inter picture prediction, to the adder 227.

The image decoding unit 200 decodes, on a block-by-block basis, the image 241 included in a coded stream 242 through the operation corresponding to the operation performed by the image coding apparatus 100.

The following describes loop filtering in more detail. The loop filtering is processing for reducing coding deterioration in a reconstructed signal, and according to H.264/MPEG-4 AVC standard (see Non Patent Literature (NPL) 1), a deblocking filtering for reducing block distortion which occurs at a macroblock boundary is performed.

However, deblocking filtering does not solve coding deterioration occurring in a macroblock. In view of this, offset processing is carried out for reducing coding deterioration according to this embodiment. The offset processing adds an offset value to a pixel included in a current block to be processed in a reconstructed signal, thereby reducing distortion from an original signal.

Furthermore, in the offset processing, pixels in the current block are classified into a plurality of categories and an offset value that is common for each category is used. Methods of classifying pixels include (i) an edge offset pixel classifying method which is performed by comparing a target pixel for classification with an adjacent pixel thereof and (ii) a band offset pixel classifying method which is performed according to a pixel value of the target pixel for classification. The edge offset is an offset performed according to an edge, and the band offset is an offset performed according to a pixel value.

In the following description, using the pixel classifying method of the edge offset is described as that the pixel classifying method is the edge offset, or as using the edge offset for the pixel classifying method, in some cases. Likewise, using the pixel classifying method of the band offset is described as that the pixel classifying method is the band offset, or as using the band offset for the pixel classifying method, in some cases.

Figures 3, 4:
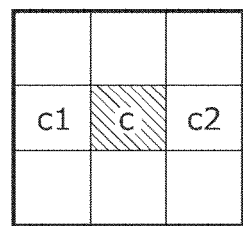
FIG. 3 is a schematic view which illustrates an example of edge offset according to Embodiment 1.
FIG. 4 is a schematic view which illustrates categories of the edge offset according to Embodiment 1.

FIG. 3 is a schematic view illustrating an example of the pixel classifying method using the edge offset. In the edge offset, classification is performed using a magnitude relationship between a current pixel c to be classified and adjacent pixels c1 and c2 located at the left and the right, respectively, of the pixel c.

FIG. 4 is a schematic view illustrating an example of classifying a block to be processed into five categories by the edge offset. For example, when a pixel value of c is larger than a pixel value of c1 and equal to a pixel value of c2, the current pixel is classified into a category 3 and an offset value Offset [3] allocated to the category 3 is added.

Figure 5:
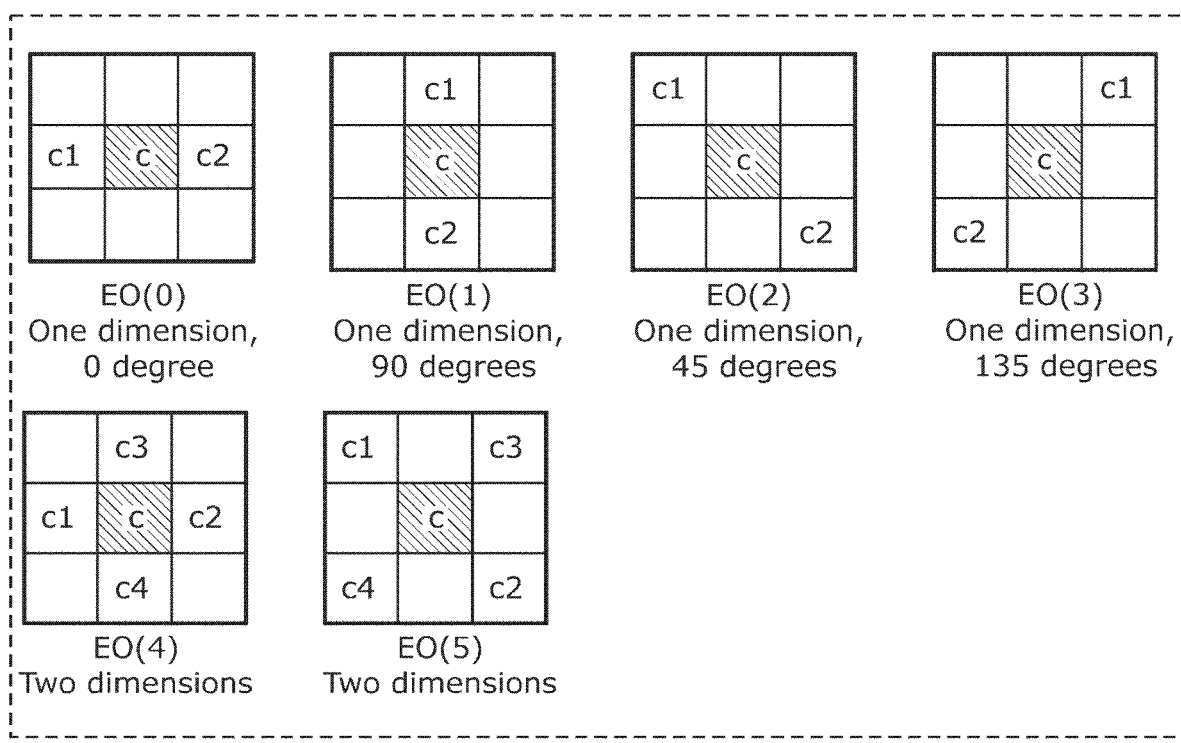
FIG. 5 is a schematic view which illustrates types of the edge offset according to Embodiment 1.

In addition, as illustrated in FIG. 5, pixels that are compared with the target pixel to be classified in the edge offset are right and left adjacent pixels (EO (0)), upper and lower adjacent pixels (EO (1)), obliquely adjacent pixels (EO (2) or EO (3)), a combination of them (EO (4) or EO (5)), and so on.

Figure 6:
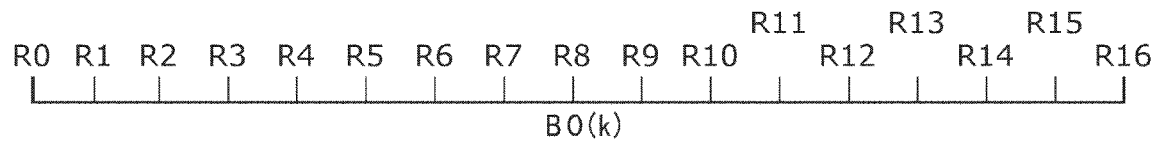
FIG. 6 is a schematic view which illustrates an example of band offset according to Embodiment 1.

FIG. 6 is a schematic view illustrating an example of the pixel classifying method using the band offset. Here, gradations which the current pixel value to be processed possibly takes are evenly divided into M. M is 32, for example. The gradation segments resulting from the division represent categories. The current pixel to be processed is classified into a category in which the pixel value is included.

Figures 7, 8:
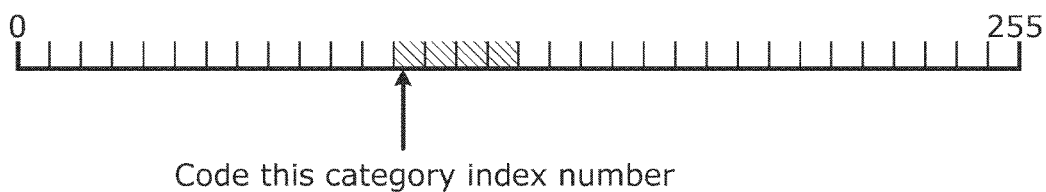
FIG. 7 is a schematic view which illustrates categories of the band offset according to Embodiment 1.
FIG. 8 is a schematic view which illustrates coding target information of the band offset according to Embodiment 1.

FIG. 7 is a schematic view illustrating an example of classifying blocks to be processed into 16 classes by the band offset. For example, when a pixel value of c is larger than or equal to R9 and smaller than R10, the current pixel to be processed is classified into a category 9 and an offset value Offset [9] allocated to the category 9 is added.

In addition, it is not necessary to allocate an offset value to all of the categories, and as illustrated in FIG. 8, the image coding apparatus 100 is capable of coding only the offset value for a category having a high offset effect. At this time, the image coding apparatus 100 codes together a category index number that indicates a category of the coded offset value.

Figure 9A:
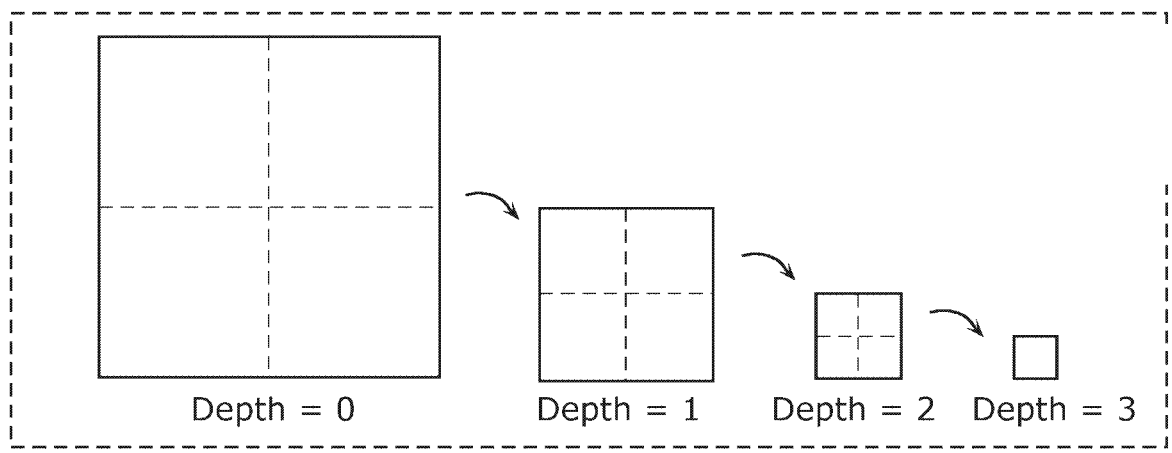
FIG. 9A is a schematic view which illustrates an example of the process of dividing a region according to Embodiment 1.
Figure 9B:
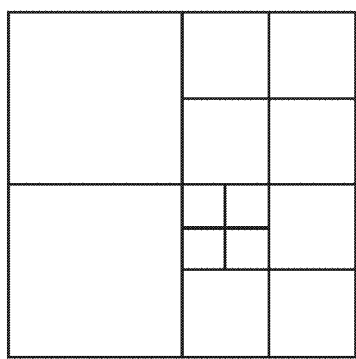
FIG. 9B is a schematic view which illustrates an example of the result of dividing a region according to Embodiment 1.

In addition, a sample adaptive offset (SAO) determines an optimal pixel classifying method and an optimal offset value to a unit of a target region to be processed that is obtained by hierarchically dividing a block, as illustrated in FIG. 9A. FIG. 9B illustrates an example of a division pattern.

Figure 10:
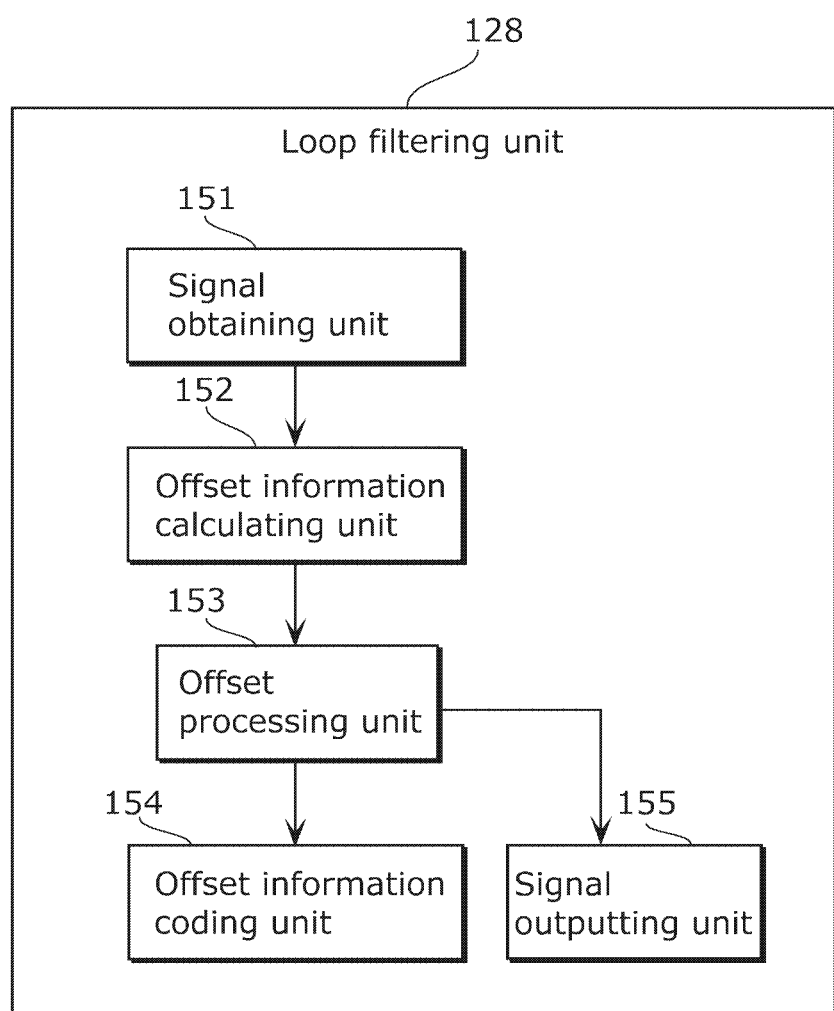
FIG. 10 is a block diagram illustrating an example of a configuration of a loop filtering unit in the image coding apparatus according to Embodiment 1.

FIG. 10 is a block diagram illustrating an example of a configuration of the loop filtering unit 128 in the image coding apparatus 100 according to this embodiment.

The loop filtering unit 128 includes: a signal obtaining unit 151; an offset information calculating unit 152; an offset processing unit 153; an offset information coding unit 154; and a signal outputting unit 155.

The signal obtaining unit 151 obtains a reconstructed pixel signal in a target region to be processed.

The offset information calculating unit 152 calculates offset information for use in offset processing, such as a division pattern, a pixel classifying method, an offset value, and so on.

The offset processing unit 153 classifies, into the categories, pixels in a target region to be processed using the offset information, and performs offset processing for each of the categories.

The offset information coding unit 154 outputs the offset information to the entropy coding unit 124 illustrated in FIG. 1. It is to be noted that the offset information coding unit 154 may code the offset information. In addition, the offset information coding unit 154 may be included in the entropy coding unit 124.

The signal outputting unit 155 outputs a pixel signal in the target region, on which the offset processing is performed.

Figure 11:
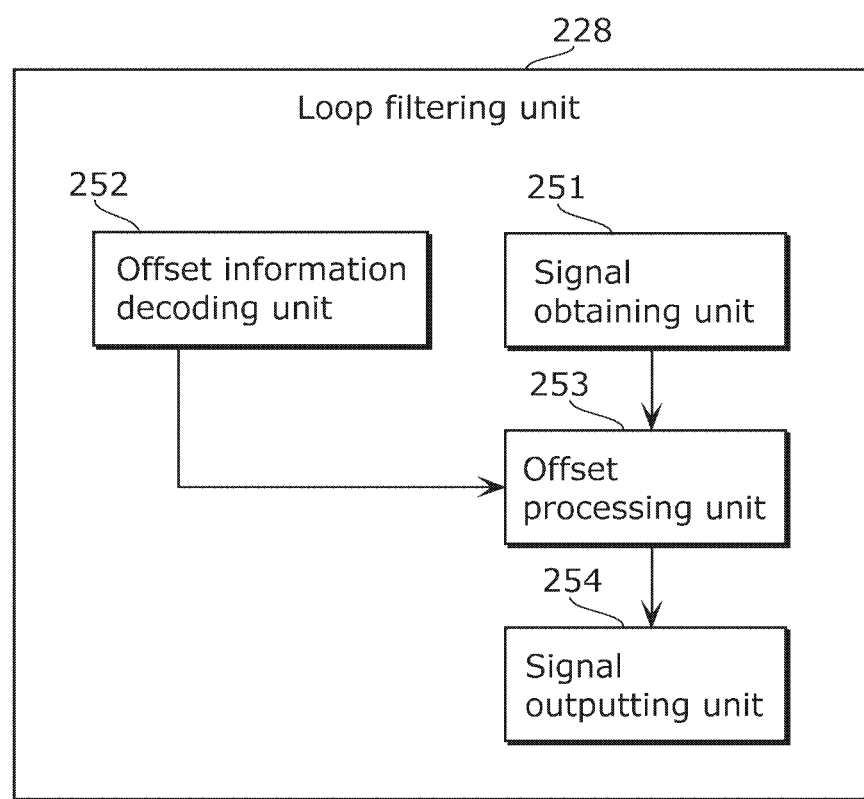
FIG. 11 is a block diagram illustrating an example of a configuration of a loop filtering unit in the image decoding apparatus according to Embodiment 1.

FIG. 11 is a block diagram illustrating an example of a configuration of the loop filtering unit 228 in the image decoding apparatus 200 according to this embodiment.

The loop filtering unit 228 includes: a signal obtaining unit 251; an offset information decoding unit 252; an offset processing unit 253; and a signal outputting unit 254.

The signal obtaining unit 251 obtains a reconstructed pixel signal in a target region to be processed The offset information decoding unit 252 obtains the offset information for use in the offset processing, such as the division pattern, the pixel classifying method, the offset value, and so on. It is to be noted that the offset information decoding unit 252 may decode the offset information. In addition, the offset information decoding unit 252 may be included in the entropy decoding unit 224.

The offset processing unit 253 classifies, into categories, pixels in a target region to be processed using the offset information, and performs the offset processing for each of the categories.

The signal outputting unit 254 outputs a pixel signal in the target region, on which the offset processing is performed.

Figure 12:
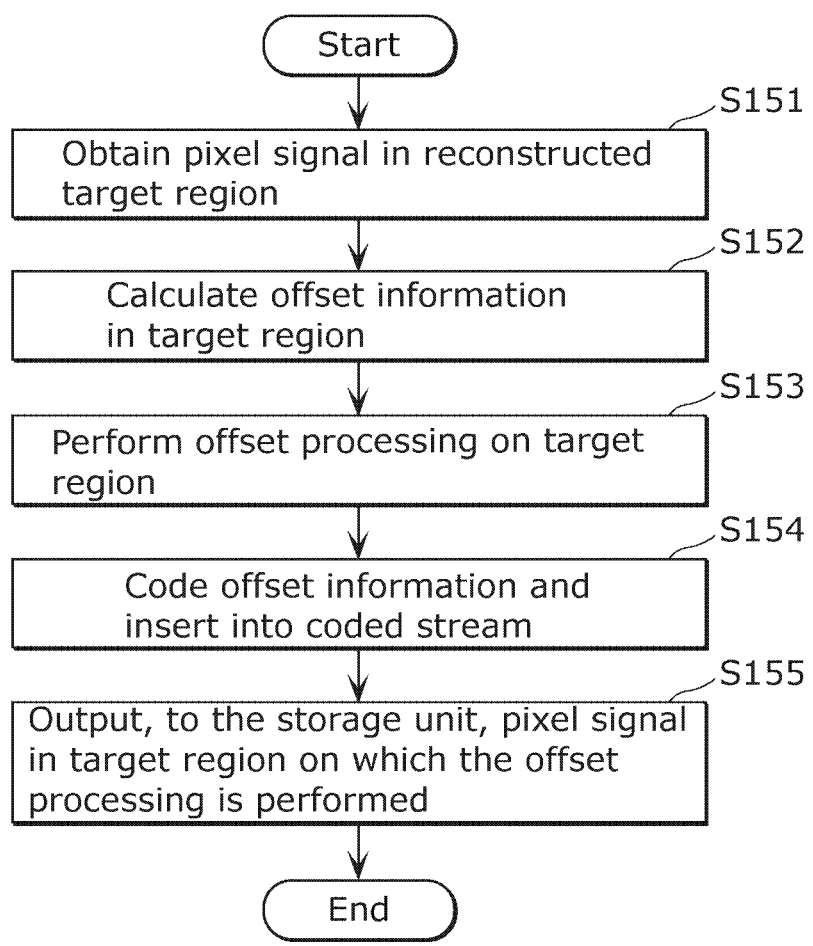
FIG. 12 is a flowchart illustrating an example of operations of the loop filtering unit in the image coding apparatus according to Embodiment 1.

FIG. 12 is a flowchart illustrating operations performed mainly by the loop filtering unit 128 illustrated in FIG. 10, of the image coding apparatus 100 illustrated in FIG. 1.

First, the signal obtaining unit 151 obtains, from the adder 127, a reconstructed pixel signal in a target region to be processed. Next, the offset information calculating unit 152 calculates the offset information for use in the offset processing, such as the division pattern, the pixel classifying method, the offset value, and so on (S152). Next, the offset processing unit 153 divides the region based on the offset information, classifies pixels in the divisional region into categories, and adds an offset value for each of the categories (S153).

Next, the offset information coding unit 154 outputs, to the entropy coding unit 124, the offset information such as the division pattern, the pixel classifying method, a category index number, the offset value, and so on. The entropy coding unit 124 codes the offset information, and inserts the coded offset information into a coded stream (S154). It is to be noted that the offset information coding unit 154 may code the offset information and insert the coded offset information into the coded stream.

Next, the signal outputting unit 155 outputs, to the storage unit 129, a pixel signal in the target region, on which the offset processing is performed (S155).

Figure 13:
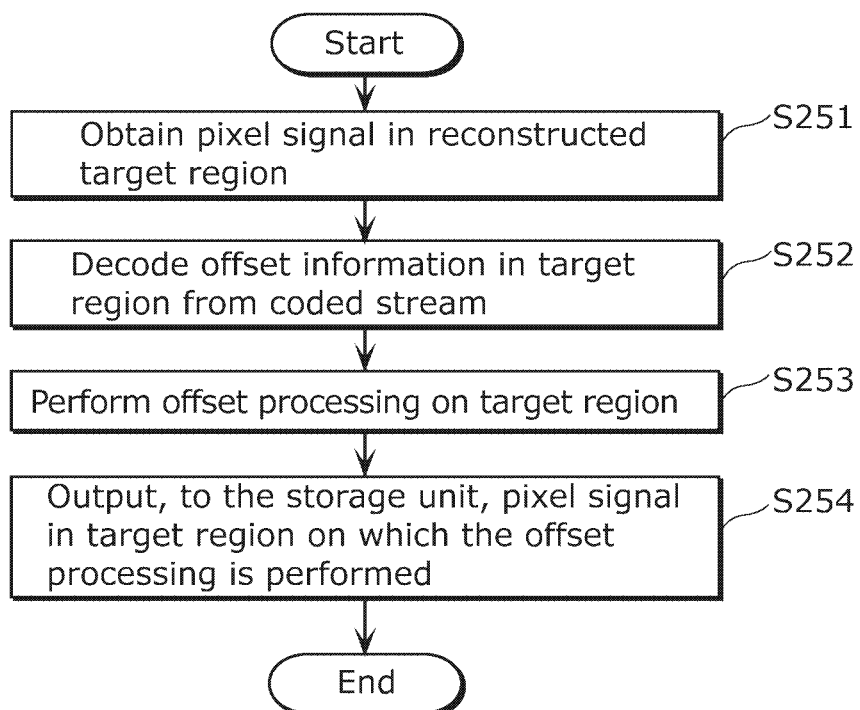
FIG. 13 is a flowchart illustrating an example of operations of the loop filtering unit in the image decoding apparatus according to Embodiment 1.

FIG. 13 is a flowchart illustrating operations performed by the loop filtering unit 228 illustrated in FIG. 11, of the image decoding apparatus 200 illustrated in FIG. 2.

First, the signal obtaining unit 251 obtains, from the adder 227, a reconstructed pixel signal in a target region to be processed.

Next, the entropy decoding unit 224 decodes, from the coded stream, the offset information such as the division pattern, the pixel classifying method, the category index number, the offset value, and so on, and the offset information decoding unit 252 obtains the decoded offset information (S252). It is to be noted that the offset information decoding unit 252 may decode the offset information from the coded stream.

Next, the offset processing unit 253 divides the region based on the offset information, classifies pixels in the divisional region into categories, and adds an offset value for each of the categories (S253). Next, the signal outputting unit 254 outputs, to the storage unit 229, a pixel signal in the target region, on which the offset processing is performed (S254).

Here, coding and decoding of the offset information in the offset information coding unit 154 and the offset information decoding unit 252 will be described in more detail. The pixel classifying methods in the offset processing include, for example, five types of methods of EO(0), EO(1), EO(2), and EO(3) for the edge offset, and BO(0) for the band offset.

Figures 14, 15:
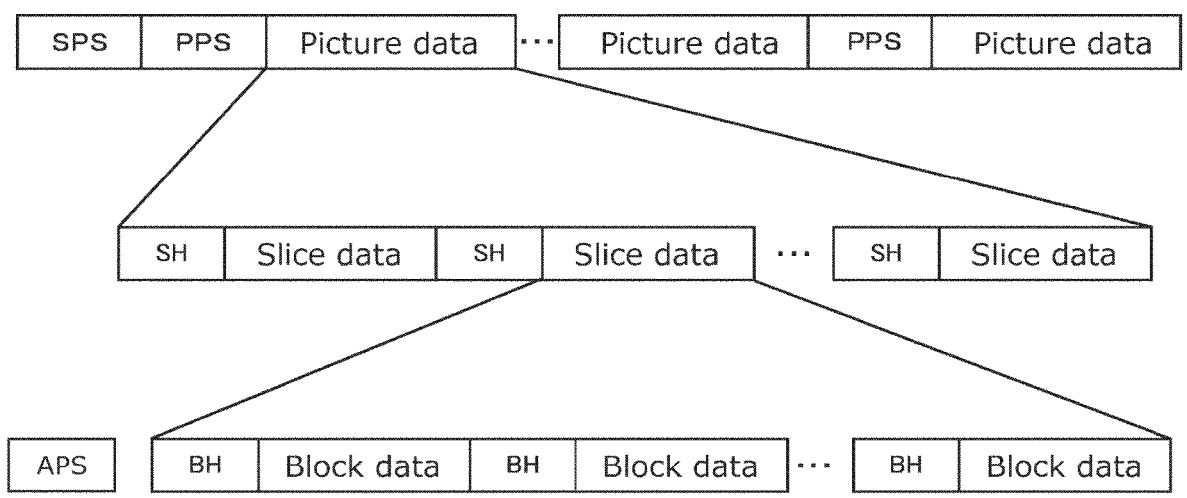
FIG. 14 is a schematic view which illustrates an example of bit allocation to index numbers each indicating a pixel classifying method according to Embodiment 1.
FIG. 15 is a schematic view which illustrates an example of a coded stream according to Embodiment 1.

FIG. 14 illustrates an example of allocating index numbers which illustrates the respective pixel classifying methods. In FIG. 14, the index numbers are each binarized such that a small value has a small bit length and a large value has a large bit length, and the maximum bit length is specified as five bits. However, the method of allocation is not limited to this. For example, the maximum bit length may not be specified, and instead, all of the index numbers may be allocated with bits such that the last bit is 0.

In addition, information indicating that the offset processing is not to be performed on a current block to be processed is allocated to the index number 0.

The image coding apparatus 100 according to Embodiment 1 generates a coded stream by coding video. As illustrated in FIG. 15, the coded stream includes a header portion such as SPS (Sequence Parameter Set), PPS (Picture Parameter Set), and so on, and picture data that is coded image data.

The picture data further includes a slice header (SH) and slice data. The slice data includes coded image data included in a slice. The slice data further includes a block header (BH) and block data. The block data includes coded image data included in a block.

Furthermore, the coded stream includes APS (Adaptation Parameter Set) in which a parameter to be used in another one or more slices is stored in addition to the above. An index number aps_idx is allocated to APS, and the image coding apparatus 100 can insert, into the slice header, the index number aps_idx for calling APS to be used.

The offset information is coded by the offset information coding unit 154 (or the entropy coding unit 124), and inserted into any one of SPS, PPS, SH, slice data, BH, block data, and APS. In addition, the offset information is obtained from any one of SPS, PPS, SH, slice data, BH, block data, and APS, and decoded by the offset information decoding unit 252 (or the entropy decoding unit 224).

Examples of inserting the offset information into APS are shown in FIG. 16A, FIG. 16B, and FIG. 16C. The image coding apparatus 100 is capable of collectively inserting the offset information of all of the blocks in a slice, and the image decoding apparatus 200 is capable of collectively obtaining the offset information from APS.

Examples of inserting the offset information into slice data are shown in FIG. 17A, FIG. 17B, and FIG. 17C. The image coding apparatus 100 is capable of inserting the offset information on a block-by-block basis in slice data, and the image decoding apparatus 200 is capable of obtaining the offset information on a block-by-block basis in slice data.

Figure 18:
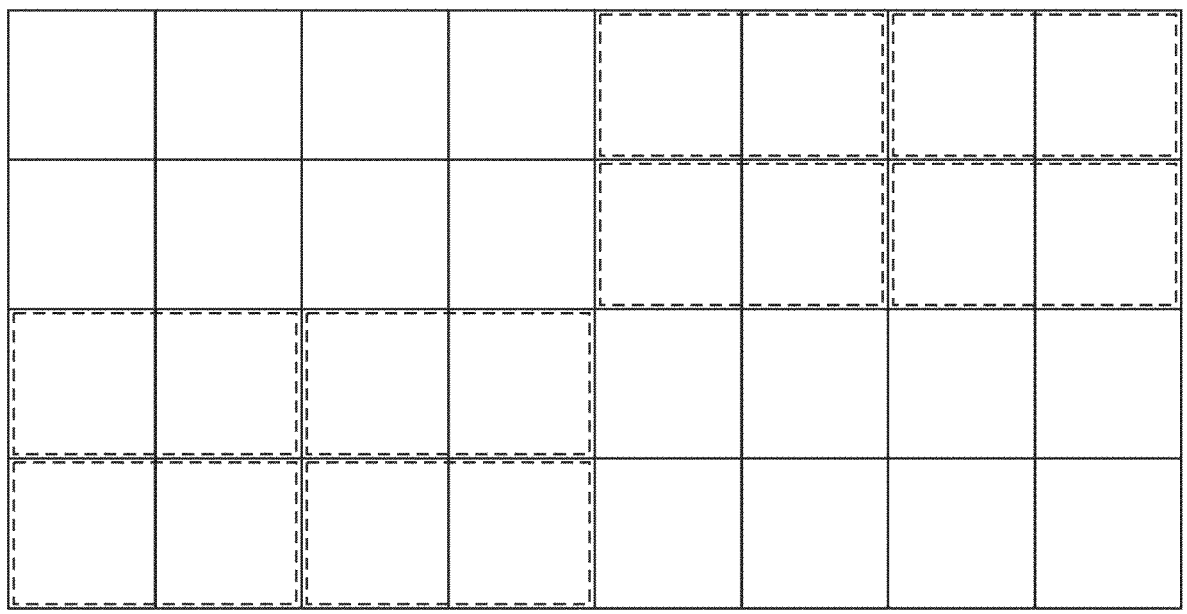
FIG. 18 is a schematic view which illustrates an example of regions between which offset information is shared according to Embodiment 1.

According to this embodiment, the offset information can be shared among a plurality of target regions to be processed in the image coding apparatus 100 (the image decoding apparatus 200) as shown in FIG. 18. The solid lines in FIG. 18 show segment boundaries of target regions for the offset processing, and the dotted lines show segment boundaries of regions between which the offset information is shared. Here, the image coding apparatus 100 inserts, into a coded stream, not offset information indicating an offset value and the like but information indicating sharing of an offset value and the like, thereby suppressing increase in a bit amount caused by offset processing.

For example, the image coding apparatus 100 may code a flag indicating that offset information is shared between all of the blocks in a slice, such as sao_one_lima_unit_flag, sao_one_cr_unit_flag, and sao_one_cb_unit_flag in FIG.

16A. In addition, the image coding apparatus 100 may code a flag indicating that offset information for a singe line is to be copied from a line immediately above, such as sao_repeat_row_flag in FIG. 16A.

Furthermore, the image coding apparatus 100 may code a parameter indicating the number of target regions to be processed between which the offset information is shared, such as saoRun and sao_run_diff in FIG. 16B. In addition, the image coding apparatus 100 may code sao_merge_left_flag or sao_merge_up_flag which indicate that offset information is to be copied from the region located on the left or the region located above, as in FIG. 16B and FIG. 17B.

Figure 19:
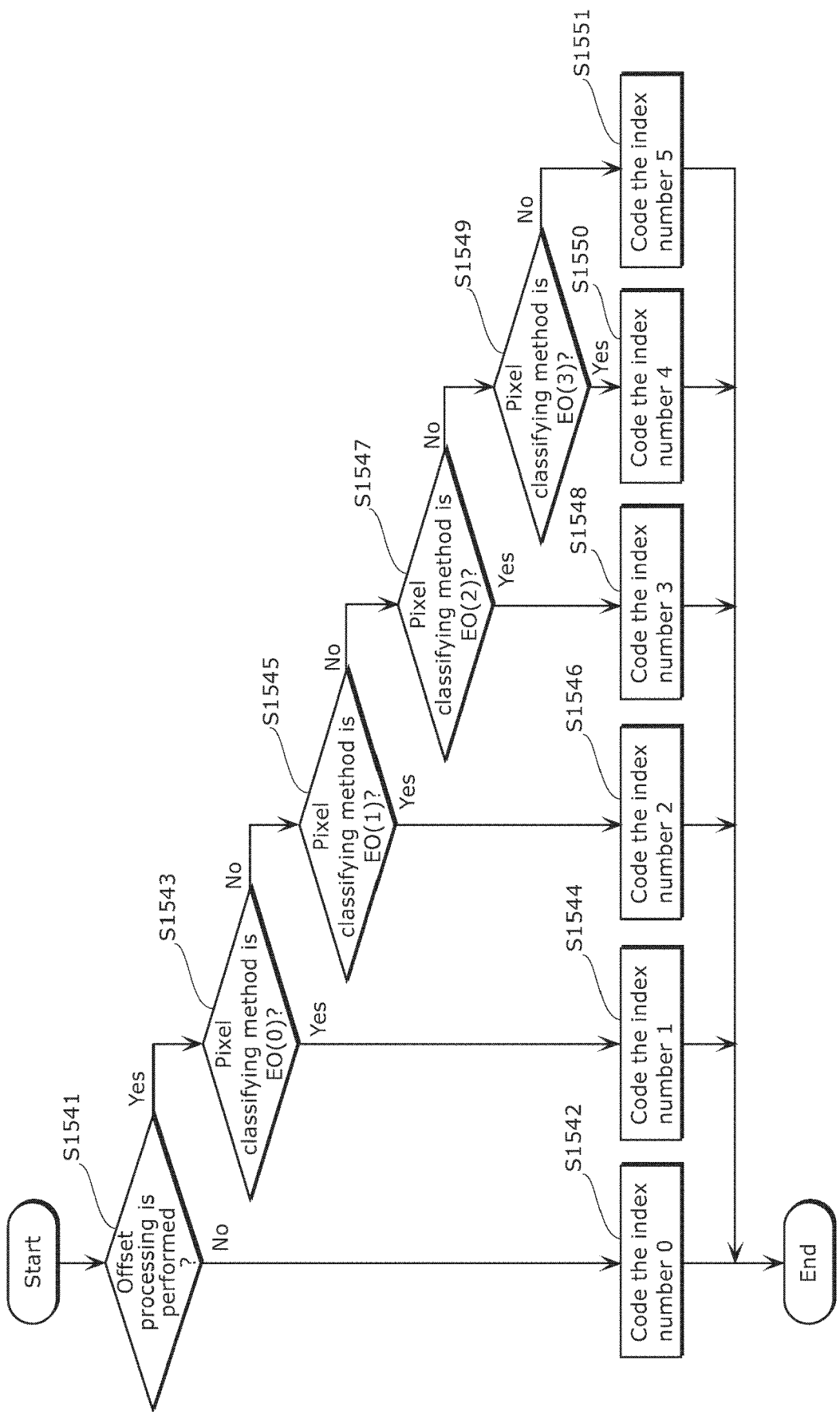
FIG. 19 is a flowchart which illustrates an example of coding an index number which indicates the pixel classifying method according to Embodiment 1.

FIG. 19 is a flowchart indicating an operation of coding, among items of the offset information, an index number that indicates a pixel classifying method, performed by the offset information coding unit 154.

First, the offset information coding unit 154 determines whether or not the offset processing is performed (S1541). The offset information calculating unit 152 calculates offset information, such as division pattern, a pixel classifying method, a category index number, an offset value, and so on. The offset information calculating unit 152 determines that offset processing is not to be performed when the bit amount required for the offset information is larger than an amount of correction of coding deterioration. In this case, the offset processing unit 153 does not perform the offset processing.

Here, the offset information coding unit 154 obtains information on whether or not the offset processing has been performed, from the offset information calculating unit 152 or the offset processing unit 153. When the offset processing has not been performed (No in S1541), the offset information coding unit 154 codes the index number 0 that indicates the pixel classifying method (S1542).

When the offset processing is performed (Yes in S1541), the offset information coding unit 154 determines whether or not the pixel classifying method is the edge offset EO(0) (S1543). When the pixel classifying method is the edge offset EO(0) (Yes in S1543), the offset information coding unit 154 codes the index number 1 that indicates the pixel classifying method (S1544).

When the pixel classifying method is not the edge offset EO(0) (No in S1543), the offset information coding unit 154 determines whether or not the pixel classifying method is the edge offset EO(1) (S1545). When the pixel classifying method is the edge offset EO(1) (Yes in S1545), the offset information coding unit 154 codes the index number 2 that indicates the pixel classifying method (S1546).

When the pixel classifying method is not the edge offset EO(1) (No in S1545), the offset information coding unit 154 determines whether or not the pixel classifying method is the edge offset EO(2) (S1547). When the pixel classifying method is the edge offset EO(2) (Yes in S1547), the offset information coding unit 154 codes the index number 3 that indicates the pixel classifying method (S1548).

When the pixel classifying method is not the edge offset EO(2) (No in S1547), the offset information coding unit 154 determines whether or not the pixel classifying method is the edge offset EO(3) (S1549). When the pixel classifying method is the edge offset EO(3) (Yes in S1549), the offset information coding unit 154 codes the index number 4 that indicates the pixel classifying method (S1550).

When the pixel classifying method is not the edge offset EO(3) (No in S1549), the offset information coding unit 154 codes the index number 5 that indicates the pixel classifying method (S1551).

Figure 20:
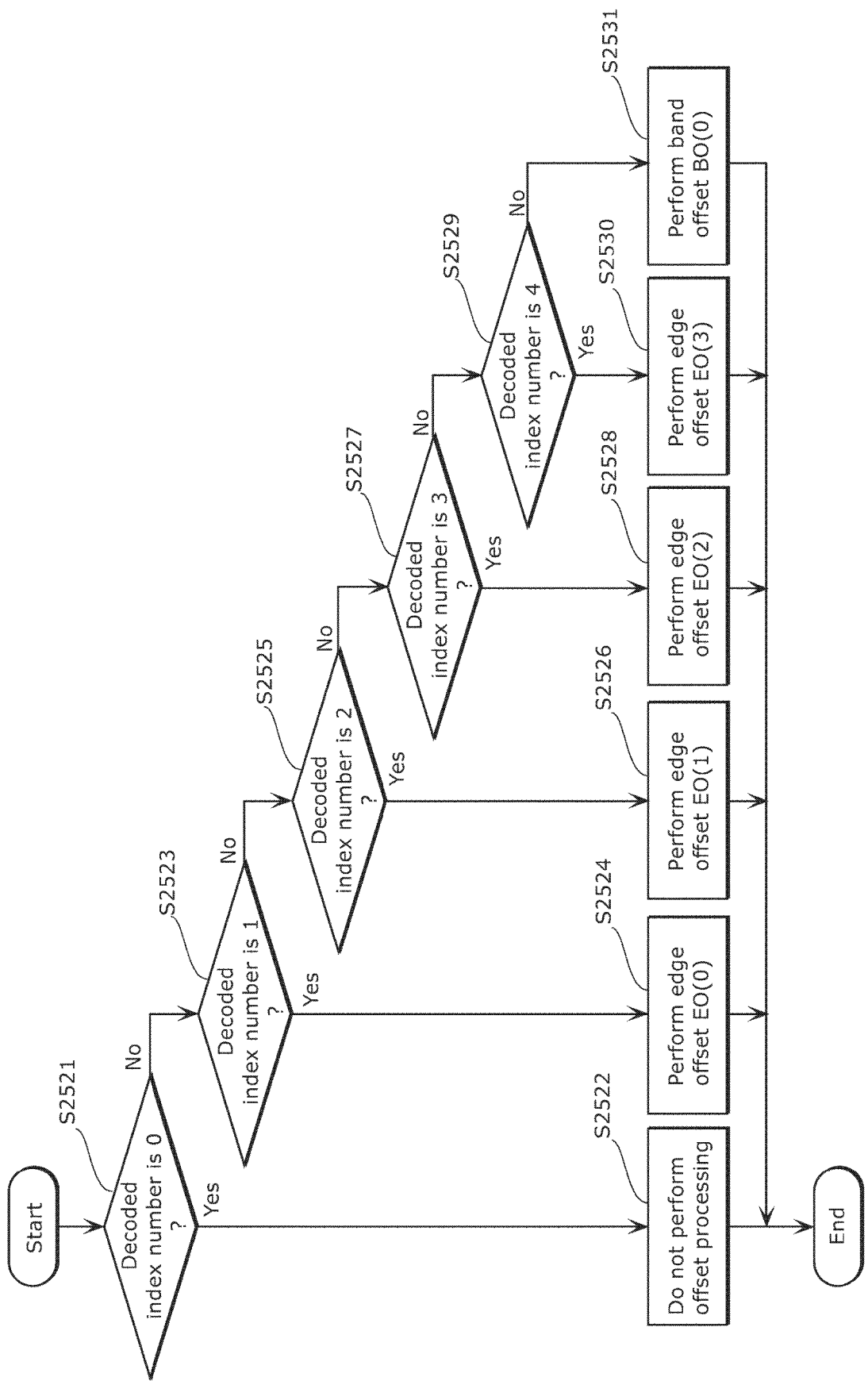
FIG. 20 is a flowchart which illustrates an example of decoding an index number which indicates the pixel classifying method according to Embodiment 1.

FIG. 20 is a flowchart indicating an operation performed by the offset information decoding unit 252 to decode, among items of the offset information, an index number that indicates the pixel classifying method, and an operation performed by the offset processing unit 253 to perform offset processing.

First, the offset processing unit 253 determines whether or not the index number decoded by the offset information decoding unit 252 is 0 (S2521). When the index number is 0 (Yes in S2521), the offset processing unit 253 does not perform the offset processing (S2522).

When the index number is not 0 (No in S2521), the offset processing unit 253 determines whether or not the index number decoded by the offset information decoding unit 252 is 1 (S2523). When the index number is 1 (Yes in S2523), the offset processing unit 253 performs the edge offset EO(0) (S2524).

When the index number is not 1 (No in S2523), the offset processing unit 253 determines whether or not the index number decoded by the offset information decoding unit 252 is 2 (S2525). When the index number is 2 (Yes in S2525), the offset processing unit 253 performs the edge offset EO(1) (S2526).

When the index number is not 2 (No in S2525), the offset processing unit 253 determines whether or not the index number decoded by the offset information decoding unit 252 is 3 (S2527). When the index number is 3 (Yes in S2527), the offset processing unit 253 performs the edge offset EO(2) (S2528).

When the index number is not 3 (No in S2527), the offset processing unit 253 determines whether or not the index number decoded by the offset information decoding unit 252 is 4 (S2529). When the index number is 4 (Yes in S2529), the offset processing unit 253 performs the edge offset EO(3) (S2530).

When the index number is not 4 (No in S2529), the offset processing unit 253 performs the band offset BO(0) (S2531).

Through the processes described above, the image coding apparatus 100 and the image decoding apparatus 200 add, to a reconstructed image signal, an offset value for making up the difference between an original signal and the reconstructed image signal. This makes it possible to generate a reconstructed signal similar to an original signal.

Embodiment 2

According to Embodiment 1, it is possible to share offset information among a plurality of regions. However, in view of reducing the processing delay or lowering the memory amount, regions to be shared are limited to adjacent ones. For example, the processing delay is reduced by limiting the regions to be shared to the adjacent regions on the left and above. Furthermore, the memory amount for storing offset information in a processed region is reduced by limiting the regions to be shared to the adjacent region on the left.

On the other hand, the limitation of the regions to be shared makes it difficult to share offset information in a large region. It is for this reason that frequency of coding the offset information grows and the bit amount increases. Here, as shown in FIG. 16C or FIG. 17C, in the band offset, a band offset coding start category sao_band_position is coded as a parameter. Thus, the bit amount is larger than that of the edge offset. Accordingly, in terms of increase in the bit amount, it is more advantageous to use the edge offset.

In view of the above, the image coding apparatus according to this embodiment reduces the bit amount required for when using the band offset, in order to correct disadvantages of the band offset compared to the edge offset. It is to be noted that the band offset coding start category sao_band- _position is an example of information that indicates a scope of application of the offset value.

The following describes an image coding apparatus according to the present embodiment and an image decoding apparatus corresponding to the image coding apparatus.

Figure 21:
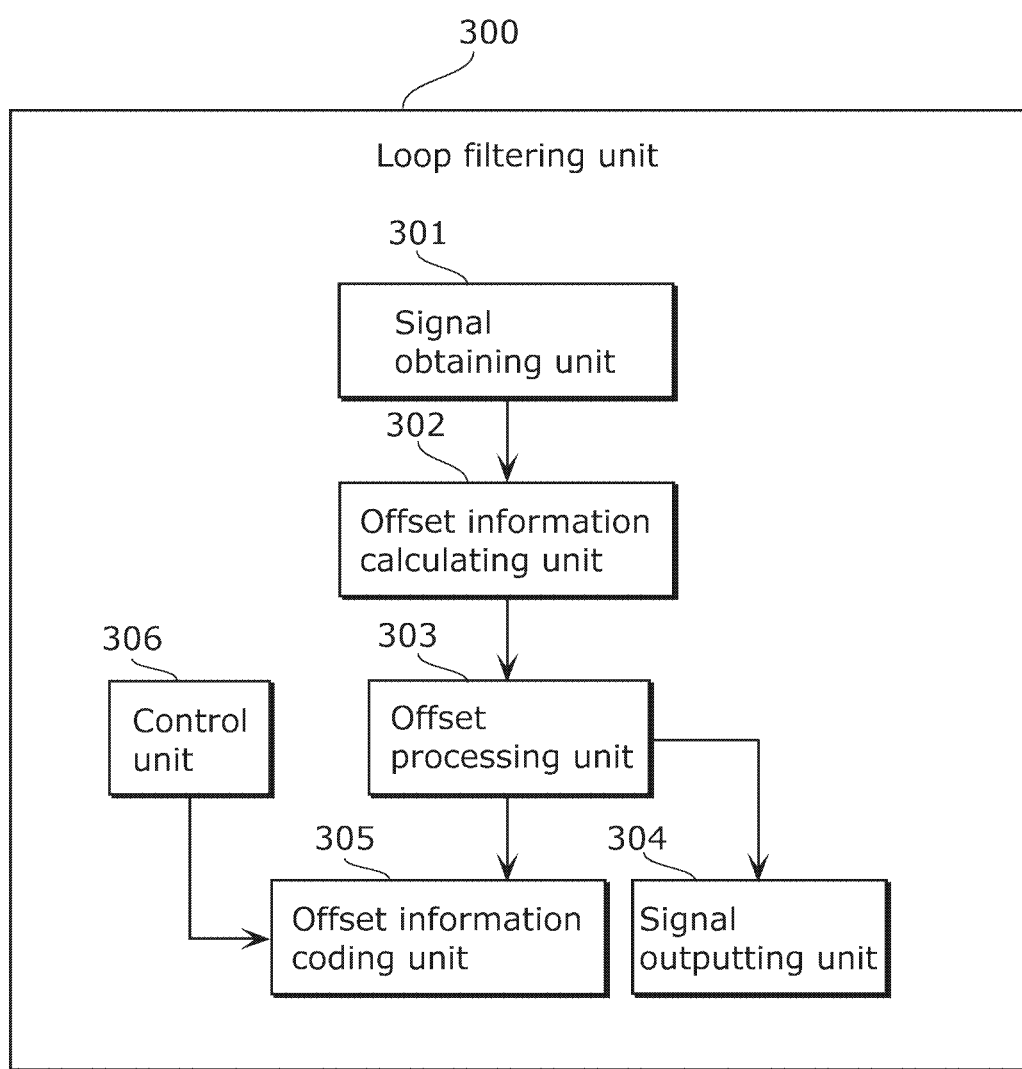
FIG. 21 is a block diagram illustrating an example of a configuration of a loop filtering unit in the image coding apparatus according to Embodiment 2.
Figure 22:
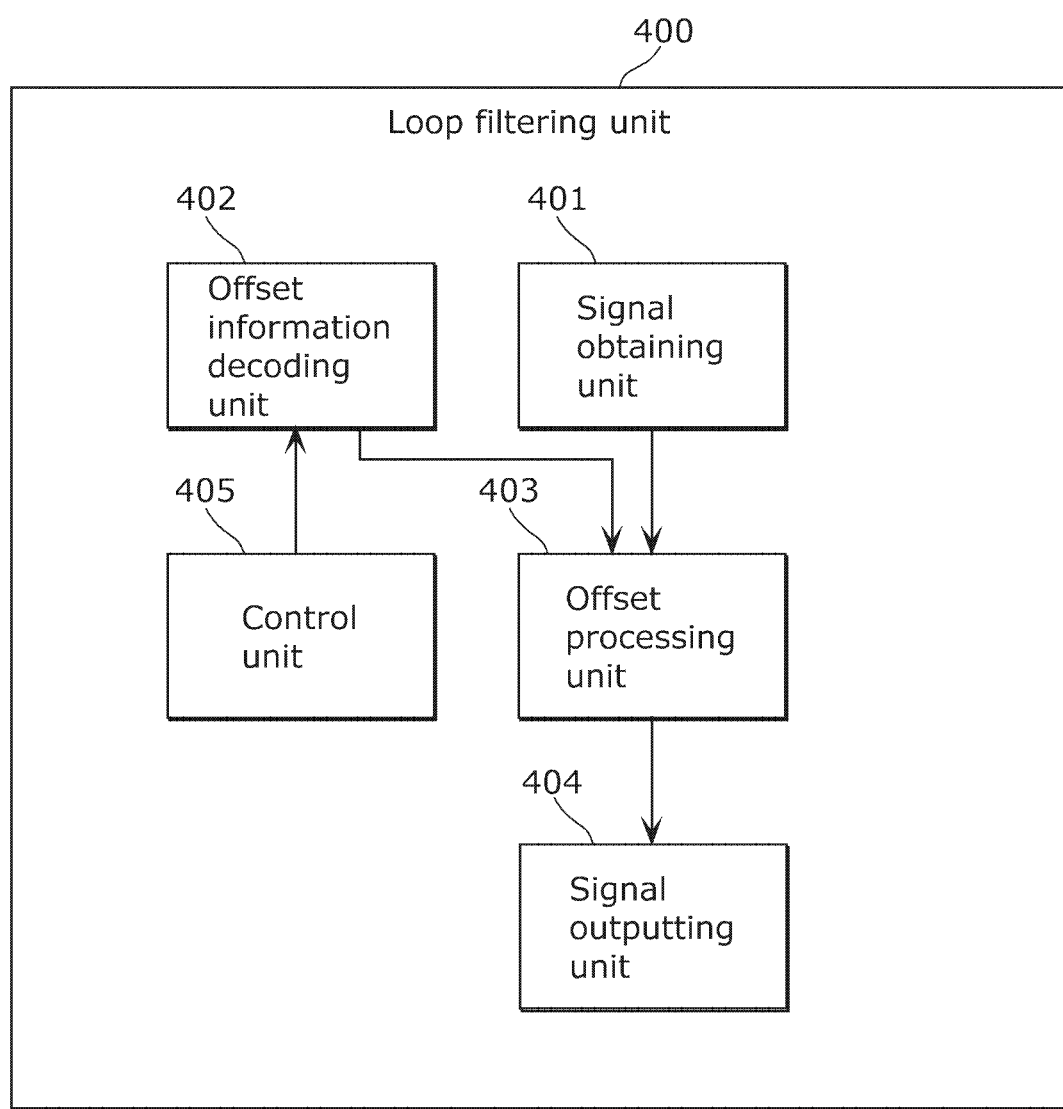
FIG. 22 is a block diagram illustrating an example of a configuration of a loop filtering unit in the image decoding apparatus according to Embodiment 2.

FIG. 21 is a block diagram illustrating a configuration of a loop filtering unit in the image coding apparatus according to this embodiment. Other configuration of the image coding apparatus according to this embodiment is substantially equivalent to the configuration of the image coding apparatus 100 illustrated in FIG. 1. FIG. 22 is a block diagram illustrating a configuration of a loop filtering unit in the image decoding apparatus according to this embodiment. Other configuration of the image decoding apparatus according to this embodiment is substantially equivalent to the configuration of the image decoding apparatus 200 illustrated in FIG. 2.

Figure 23:
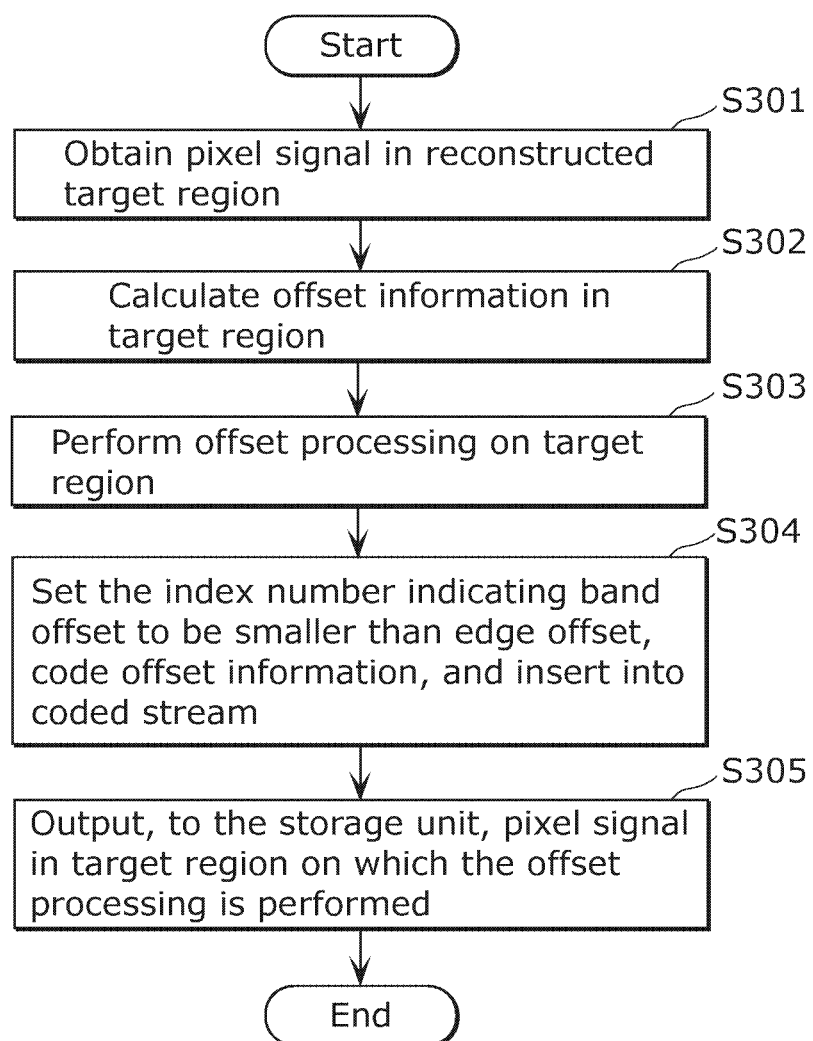
FIG. 23 is a flowchart illustrating an example of operations of the loop filtering unit in the image coding apparatus according to Embodiment 2.
Figure 24:
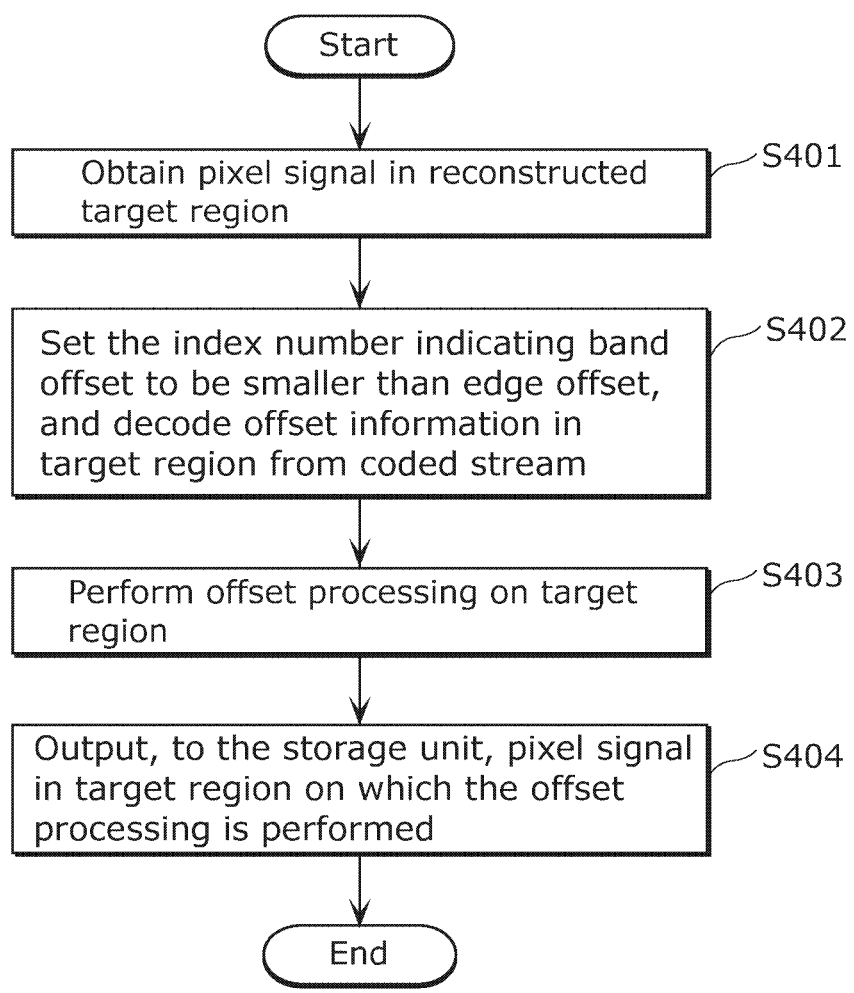
FIG. 24 is a flowchart illustrating an example of operations of the loop filtering unit in the image decoding apparatus according to Embodiment 2.

FIG. 23 is a flowchart illustrating operations performed by a loop filtering unit 300 (a loop filtering unit of the image coding apparatus) illustrated in FIG. 21. FIG. 24 is a flowchart illustrating operations performed by a loop filtering unit 400 (a loop filtering unit of the image decoding apparatus) illustrated in FIG. 22.

First, the configuration and the operation of the loop filtering unit 300 (the loop filtering unit of the image coding apparatus) illustrated in FIG. 21 will be described. The loop filtering unit 300 includes: a signal obtaining unit 301; an offset information calculating unit 302; an offset processing unit 303; a signal outputting unit 304; an offset information coding unit 305; and a control unit 306. Description for overlapping portions with Embodiment 1 will be omitted, and for the differences; that is, the control unit 306 in FIG. 21, the offset information coding unit 305 in FIG. 21, and Step S304 in FIG. 23 will be described.

The control unit 306 controls the offset information coding unit 305 to reduce the bit amount of the offset information of the band offset, when the pixel classifying method is the band offset.

The offset information coding unit 305 performs coding to reduce the numerical value of the index number indicating that the pixel classifying method is the band offset.

In Step S304 of FIG. 23, the offset information coding unit 305 allocates an index number to the pixel classifying method and codes the offset information. At this time, the offset information coding unit 305 allocates the index number such that the index number that indicates the band offset BO(0) is smaller than four edge offsets EO(0), EO(1), EO(2), and EO(3). Then, the offset information coding unit 305 inserts the coded offset information into the coded stream.

Next, the configuration and the operation of the loop filtering unit 400 (the loop filtering unit of the image decoding apparatus) illustrated in FIG. 22 will be described. The loop filtering unit 400 includes: a signal obtaining unit 401; an offset information decoding unit 402; an offset processing unit 403; a signal outputting unit 404; and a control unit 405. Description for overlapping portions with Embodiment 1 will be omitted, and for the differences; that is, the control unit 405 in FIG. 22, the offset information decoding unit 402 in FIG. 22, and Step S402 in FIG. 24 will be described.

The control unit 405 controls the offset information decoding unit 402 such that the offset information of the band offset is decoded with a small bit amount when the pixel classifying method is the band offset.

The offset information decoding unit 402 decodes the index number with a small numerical value, as an index number indicating that the pixel classifying method is the band offset.

In Step S402 of FIG. 24, the offset information decoding unit 402 allocates an index number to the pixel classifying method and decodes the offset information. At this time, the offset information decoding unit 402 allocates the index number such that the index number that indicates the band offset BO(0) is smaller than the four edge offsets EO(0), EO(1), EO(2), and EO(3).

Here, coding and decoding of the offset information performed by the offset information coding unit 305 and the offset information decoding unit 402 will be described in more detail. For the pixel classifying methods in the offset processing, the edge offsets EO(0), EO(1), EO(2), and EO(3), and the band offset BO(0) are employed as with Embodiment 1. In this case, the difference between the smallest bit amount and the largest bit amount which correspond to the index number indicating the pixel classifying method is three bits excepting the index number 0 for the case when the offset processing is not performed.

In Embodiment 1, the largest bit amount is allocated to the band offset as shown in FIG. 14. When the number of categories of the band offset is 32, a difference of at most eight bits and at least five bits including sao_band_position is generated between the band offset and the edge offset.

For that reason, according to this embodiment, a bit smaller than that in the case of the edge offset is allocated to the index number indicating the band offset as shown in FIG. 25. With this, the difference of the bit amount between the band offset and the edge offset is at most four bits and at least two bits, correcting disadvantages of the band offset compared to the edge offset.

It is to be noted that, as shown in FIG. 26, an offset processing ON/OFF flag (an offset processing flag) may be independent, as sao_on_flag, from the index number sao_type_idx that indicates the pixel classifying method.

In FIG. 26, the band offset is allocated to the index number 0. The index numbers are each binarized such that a small value has a small bit length and a large value has a large bit length, and the maximum bit length is specified as four bits. However, the method of allocation is not limited to the above. For example, the maximum bit length may not be specified, and instead, all of the index numbers may be allocated with bits such that the last bit is 0. Subsequently, the description will be given based on the bit allocation shown in FIG. 26.

Examples of inserting the offset information into APS are shown in FIG. 27A and FIG. 27B. The offset processing ON/OFF flag sao_on_flag which is independent from the index that indicates the pixel classifying method is newly provided in the sao_unit_vlc shown in FIG. 27A. In addition, the smallest bit is allocated to the band offset in sao_type_idx of sao_offset_vlc in FIG. 27B.

Figures 27C, 27D:
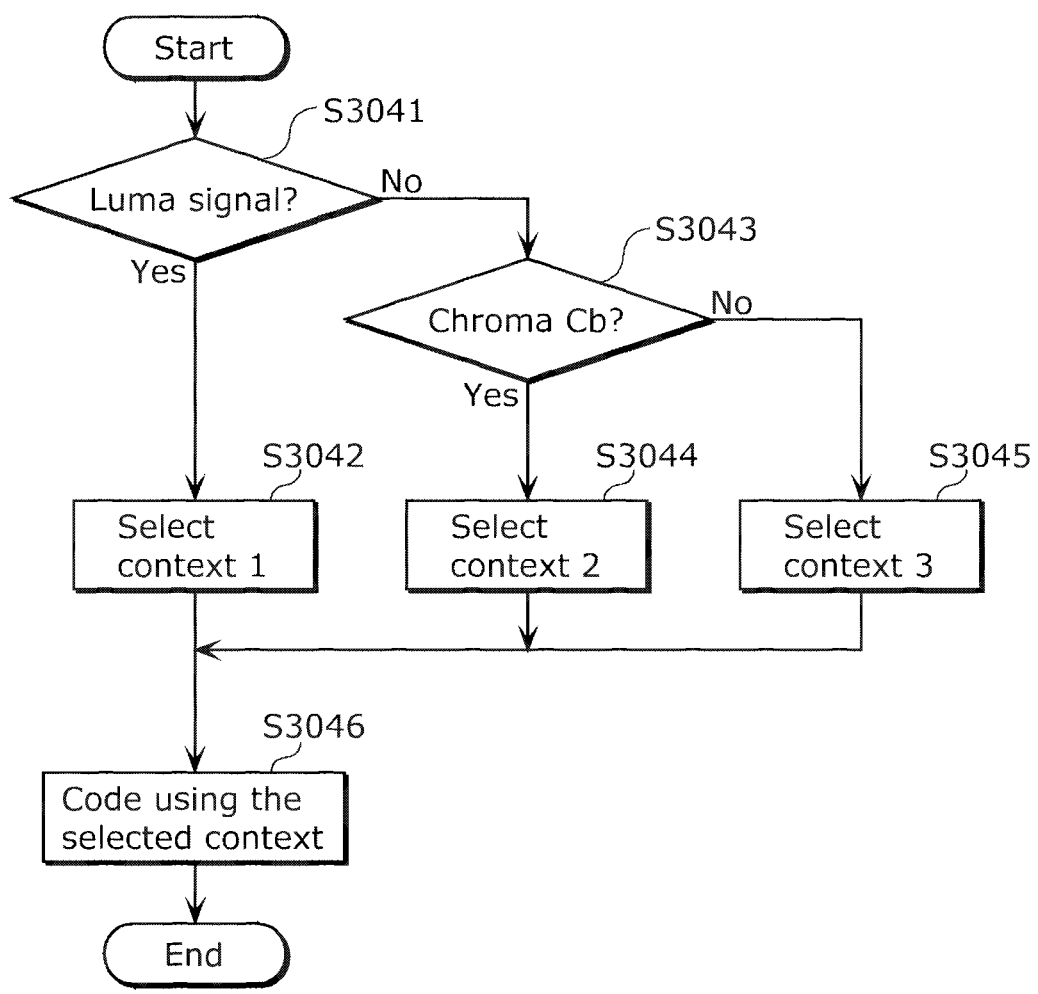
FIG. 27C is a schematic view which illustrates an example of allocation of a context index to offset information in APS according to Embodiment 2.
FIG. 27D is a flowchart which illustrates an example of coding of offset information in APS according to Embodiment 2
Figure 27E:
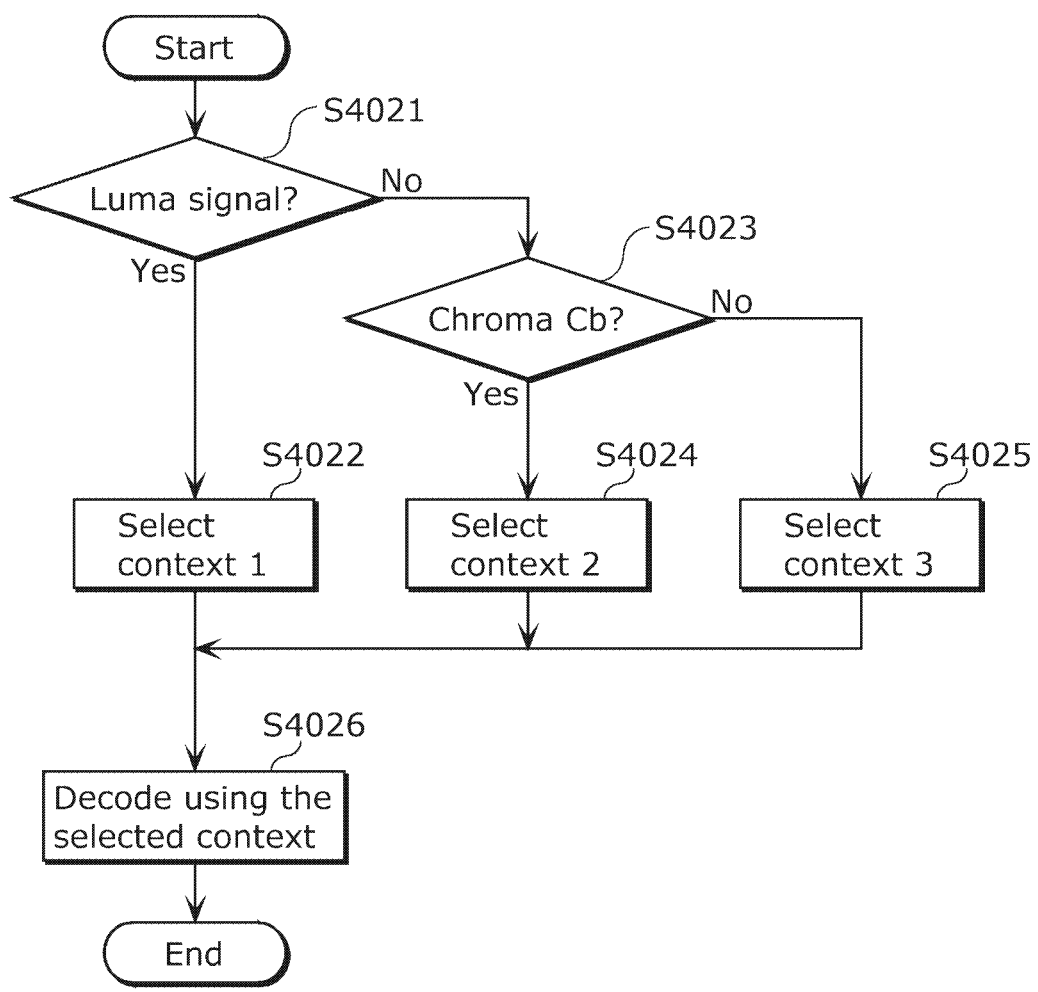
FIG. 27E is a flowchart which shows an example of decoding of offset information in APS according to Embodiment 2.

FIG. 27C is a diagram which shows an example of contexts of offset information in APS. FIG. 27D is a flowchart which shows an example of coding the offset information in APS. FIG. 27E is a flowchart which shows an example of decoding the offset information in APS.

In addition, Examples of inserting the offset information into slice data are shown in FIG. 28A and FIG. 28B. The offset processing ON/OFF flag sao_on_flag is newly provided in sao_unit_cabac shown in FIG. 28A. In addition, the smallest bit is allocated to the band offset in sao_type_idx of sao_offset_cabac shown in FIG. 28B.

Figure 28D:
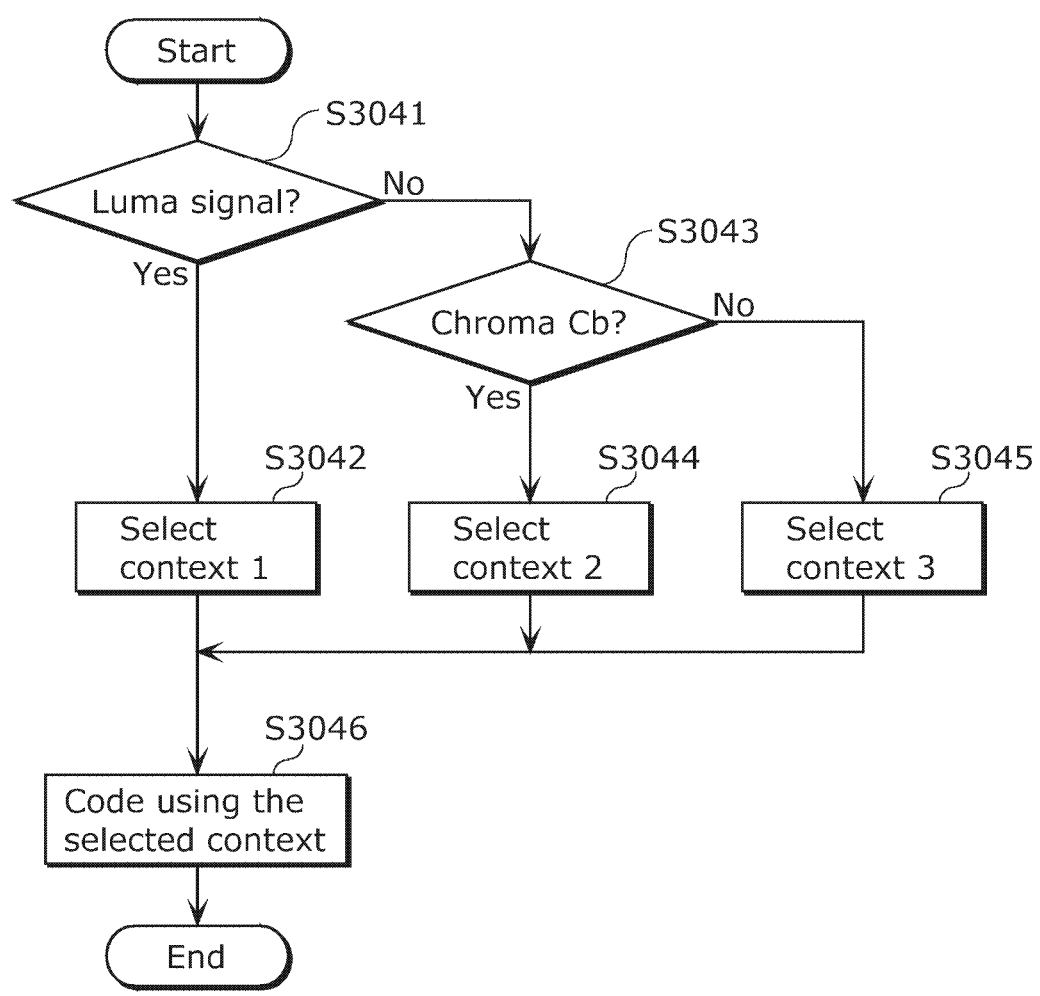
FIG. 28D is a flowchart which illustrates an example of coding of offset information in slice data according to Embodiment 2.
Figure 28E:
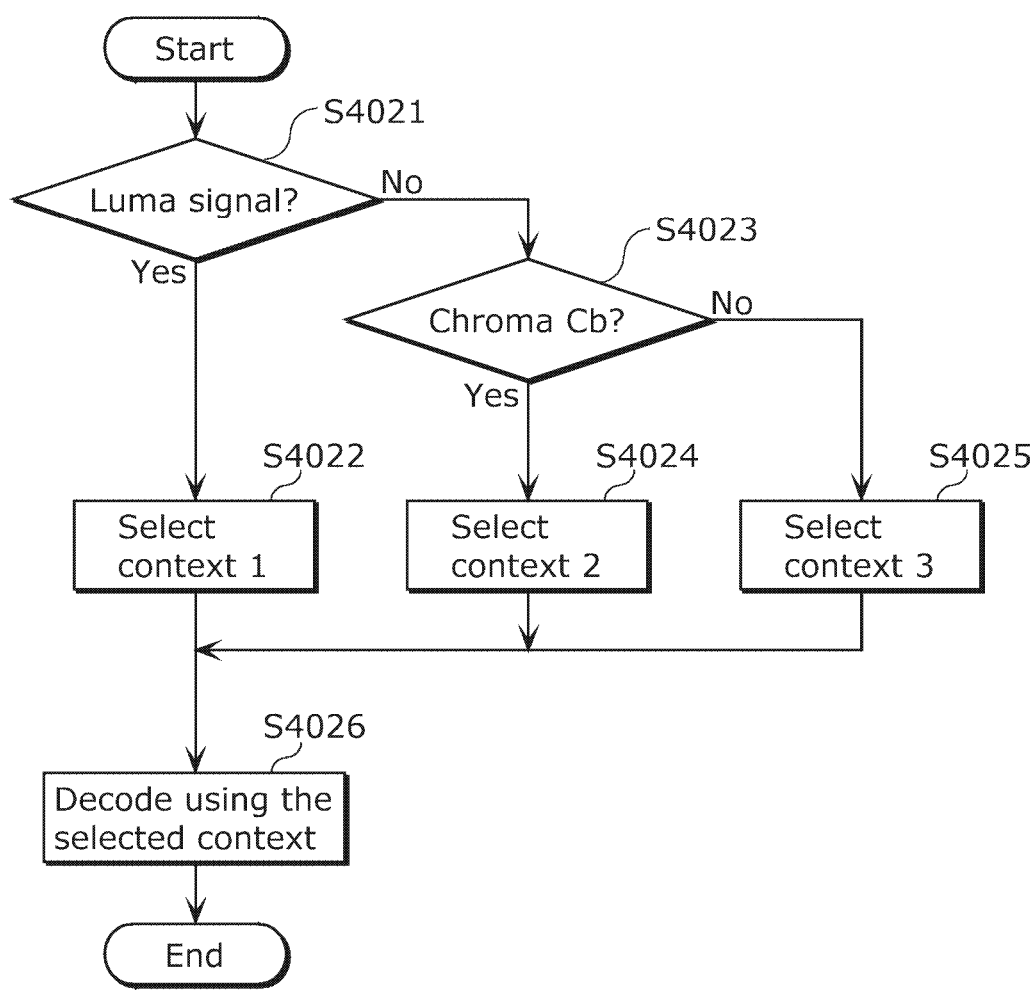
FIG. 28E is a flowchart which shows an example of decoding of offset information in slice data according to Embodiment 2.

FIG. 28C is a schematic view illustrating an example of contexts of offset information in slice data. FIG. 28D is a flowchart which shows an example of coding the offset information in slice data. FIG. 28E is a flowchart which shows an example of decoding the offset information in slice data.

Figure 29:
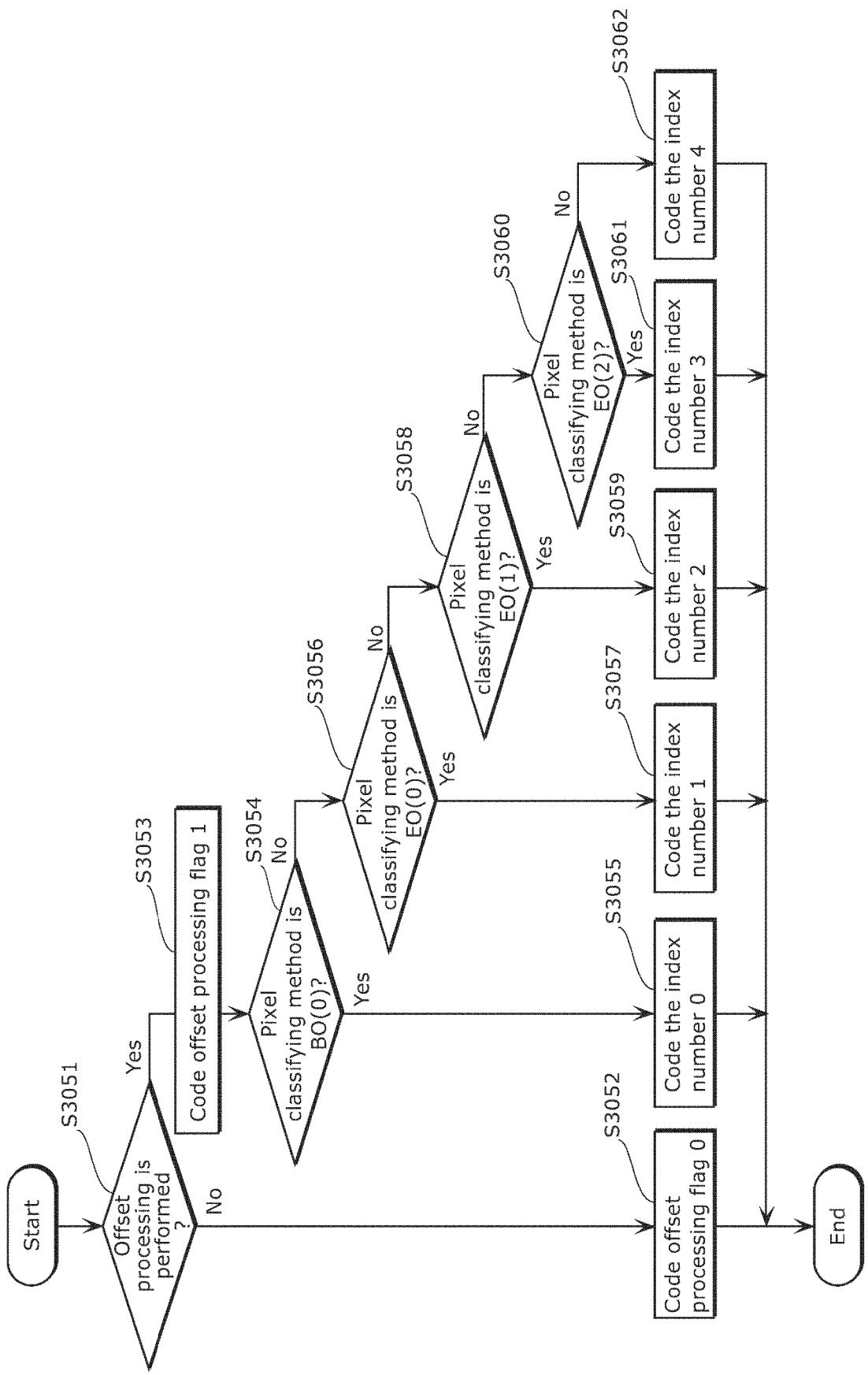
FIG. 29 is a flowchart which illustrates an example of coding of an index number which indicates a pixel classifying method according to Embodiment 2.

FIG. 29 is a flowchart indicating an operation of coding, among items of offset information, an index number that indicates a pixel classifying method, performed by the offset information coding unit 305.

First, the offset information coding unit 305 determines whether or not offset processing is performed (S3051). The offset information calculating unit 302 calculates offset information, such as the division pattern, the pixel classifying method, the category index number, the offset value, and so on. The offset information calculating unit 302 determines that offset processing is not to be performed when the bit amount required for the offset information is larger than an amount of correction of coding deterioration. In this case, the offset processing unit 303 does not perform the offset processing.

Here, the offset information coding unit 305 obtains information on whether or not the offset processing has been performed, from the offset information calculating unit 302 or the offset processing unit 303. When the offset processing has not been performed (No in S3051), the offset information coding unit 305 codes the offset processing ON/OFF flag as 0 (S3052).

When the offset processing has been performed (Yes in S3051), the offset information coding unit 305 codes the offset processing ON/OFF flag as 1 (S3053). Then, the offset information coding unit 305 determines whether or not the pixel classifying method is the band offset BO(0) (S3054).

When the pixel classifying method is the band offset BO(0) (Yes in S3054), the offset information coding unit 305 codes the index number 0 that indicates the pixel classifying method (S3055). When the pixel classifying method is not the band offset BO(0) (NO in S3054), the offset information coding unit 305 determines whether or not the pixel classifying method is the edge offset EO(0) (S3056).

When the pixel classifying method is the edge offset EO(0) (Yes in S3056), the offset information coding unit 305 codes the index number 1 that indicates the pixel classifying method (S3057). When the pixel classifying method is not the edge offset EO(0) (NO in S3056), the offset information coding unit 305 determines whether or not the pixel classifying method is the edge offset EO(1) (S3058).

When the pixel classifying method is the edge offset EO(1) (Yes in S3058), the offset information coding unit 305 codes the index number 2 that indicates the pixel classifying method (S3059). When the pixel classifying method is not the edge offset EO(1) (NO in S3058), the offset information coding unit 305 determines whether or not the pixel classifying method is the edge offset EO(2) (S3060).

When the pixel classifying method is the edge offset EO(2) (Yes in S3060), the offset information coding unit 305 codes the index number 3 that indicates the pixel classifying method (S3061). When the pixel classifying method is not the edge offset EO(2) (No in S3060), the offset information coding unit 305 codes the index number 4 that indicates the pixel classifying method (S3062).

Figure 30:
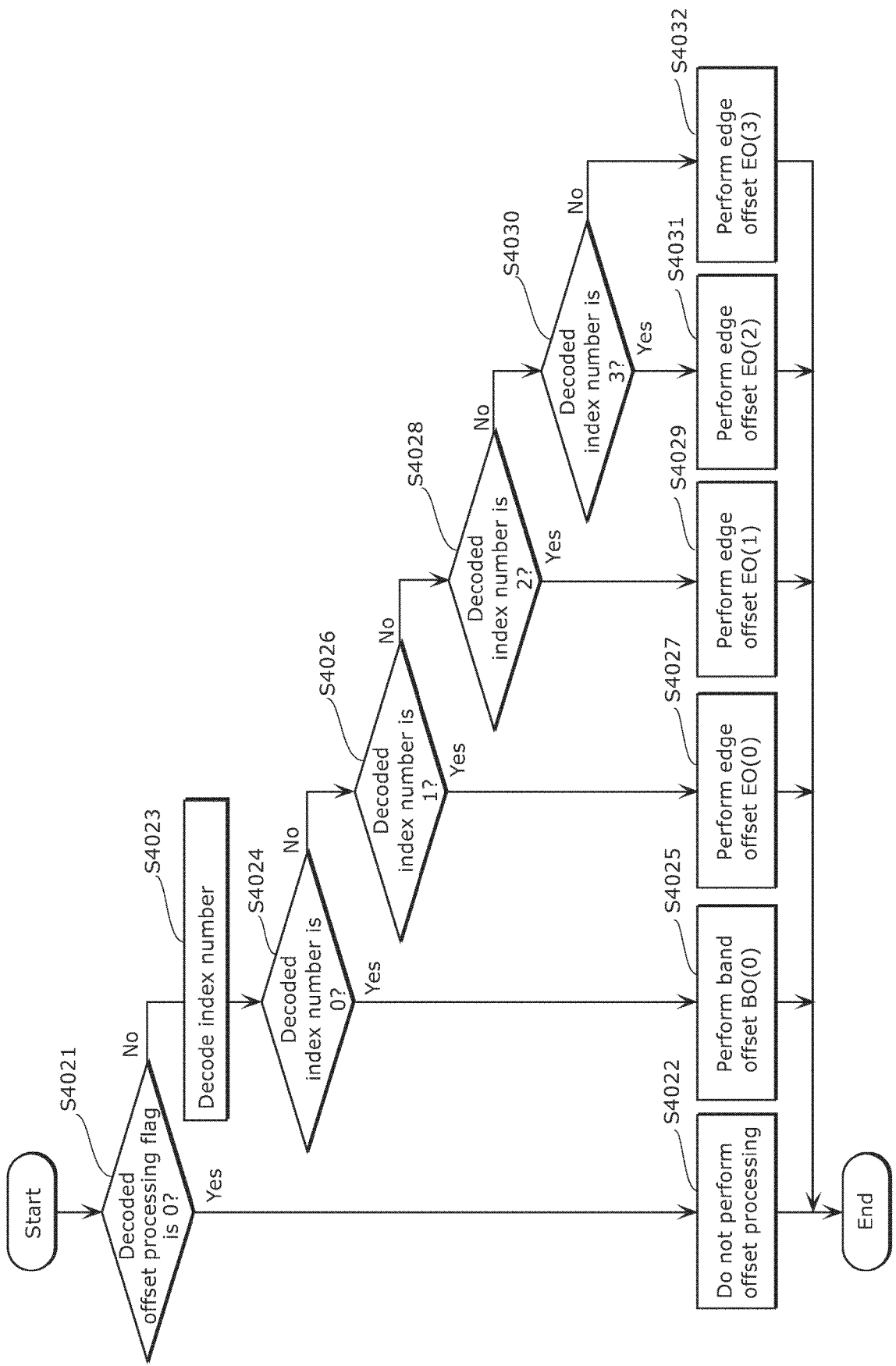
FIG. 30 is a flowchart which illustrates an example of decoding an index number which indicates the pixel classifying method according to Embodiment 2.

FIG. 30 is a flowchart indicating an operation performed by the offset information decoding unit 402 to decode, among items of the offset information, the index number that indicates the pixel classifying method, and an operation performed by the offset processing unit 403 to perform offset processing.

First, the offset processing unit 403 determines whether or not the offset processing ON/OFF flag decoded by the offset information decoding unit 402 is 0 (S4021). When the offset processing ON/OFF flag is 0 (Yes in S4021), the offset processing unit 403 does not perform the offset processing (S4022).

When the offset processing ON/OFF flag is not 0 (No in S4021), the offset information decoding unit 402 decodes the index number (S4023). Then, the offset processing unit 403 determines whether or not the index number decoded by the offset information decoding unit 402 is 0 (S4024).

When the index number is 0 (Yes in S4024), the offset processing unit 403 performs the band offset BO(0) (S4025). When the index number is not 0 (No in S4024), the offset processing unit 403 determines whether or not the index number decoded by the offset information decoding unit 402 is 1 (S4026).

When the index number is 1 (Yes in S4026), the offset processing unit 403 performs the edge offset EO(0)) (S4027). When the index number is not 1 (No in S4026), the offset processing unit 403 determines whether or not the index number decoded by the offset information decoding unit 402 is 2 (S4028).

When the index number is 2 (Yes in S4028), the offset processing unit 403 performs the edge offset EO(1) (S4029). When the index number is not 2 (No in S4028), the offset processing unit 403 determines whether or not the index number decoded by the offset information decoding unit 402 is 3 (S4030).

When the index number is 3 (Yes in S4030), the offset processing unit 403 performs the edge offset EO(2) (S4031). When the index number is not 3 (No in S4030), the offset processing unit 403 performs the edge offset EO(3) (S4032).

Through the processes described above, the image coding apparatus and the image decoding apparatus reduce the difference in the bit amount required for coding the offset information between the band offset and the edge offset. This allows the image coding apparatus and the image decoding apparatus to perform appropriate offset processing for each of the target regions to be processed. Therefore, the coding efficiency and a subjective image quality are improved.

It is to be noted that the image coding apparatus and the image decoding apparatus may allocate a small bit amount to an index number of the edge offset when the offset processing is performed to a luma signal. Also, the image coding apparatus and the image decoding apparatus may allocate a small bit amount to an index number of the band offset when the offset processing is performed to a chroma signal. This facilitates use of the pixel classifying method that is more suitable to the feature of the signal to be processed. Therefore, the coding efficiency and the subjective image quality are further improved.

In addition, the image coding apparatus and the image decoding apparatus may refer to a frequency transformation coefficient and allocate a small bit amount to an index number of the edge offset in a region to be processed which has a small low-frequency component. Also, the image coding apparatus and the image decoding apparatus may allocate a small bit amount to an index number of the band offset in a region to be processed which has a large low-frequency component. This facilitates use of the pixel classifying method that is more suitable to the feature of the signal to be processed. Therefore, the coding efficiency and the subjective image quality are further improved.

In addition, for determining whether the amount of the above-described low-frequency components is great or small, a threshold may be used, or the threshold may be coded.

Here, arithmetic coding will be descried as a method for coding and decoding offset information performed by the offset information coding unit 305 and the offset information decoding unit 402. In the arithmetic coding, the image coding apparatus first transforms (binarizes) a current signal to be coded from a multivalued signal to a binary signal (bin, a signal of 0 or 1) and performs arithmetic coding on the binary signal to generate a bitstream. One example of the arithmetic coding is context arithmetic coding (context adaptive arithmetic coding) in which arithmetic coding is performed using an adaptive symbol occurrence probability.

In the context arithmetic coding, the image coding apparatus selects a context for each of the signals to be coded, and determines a symbol occurrence probability according to the context. More specifically, in the context arithmetic coding, the image coding apparatus first loads a context and perform the arithmetic coding on a current signal to be coded based on a symbol occurrence probability for the context. Then, the image coding apparatus updates the symbol occurrence probability corresponding to the context according to a value of the current signal that is coded.

In coding of the offset processing ON/OFF flag sao_on_flag in a luma signal, a chroma signal Cb, and a chroma signal Cr, a common context may be used, or contexts may be changed for each of the signals as shown in FIG. 27C or FIG. 28C.

FIG. 28D is a flowchart which shows an example of using three contexts when the offset information coding unit 305 codes, and inserts into slice data, the offset processing ON/OFF flag sao_on_flag.

First, the offset information coding unit 305 determines whether or not a current signal to be processed is a luma signal (S3041). The offset information coding unit 305 uses cIdx illustrated in FIG. 28A for determining of the luma signal. Here, when cIdx=0, the current signal is a luma signal.

When the current signal is a luma signal (Yes in S3041), the offset information coding unit 305 selects and loads the context 1 (S3042). When the current signal is not a luma signal (No in S3041), the offset information coding unit 305 determines whether or not the current signal is a chroma signal Cb (S3043). The offset information coding unit 305 uses cIdx for determining of the chroma signal Cb in the same manner as the determining of the luma signal (S3041). Here, when cIdx=1, the current signal is a chroma signal Cb.

When the current signal is the chroma signal Cb (Yes in S3043), the offset information coding unit 305 selects and loads the context 2 (S3044). When the current signal is not the chroma signal Cb (No in S3043), the offset information coding unit 305 selects and loads the context 3 (S3045).

Then, the offset information coding unit 305 codes the offset processing ON/OFF flag sao_on_flag using the context which is selected and loaded (S3046).

It is to be noted that the flowchart illustrated in FIG. 27D which shows an example of the case where the offset processing ON/OFF flag sao_on_flag is coded and inserted into APS is the same as that illustrate in FIG. 28 described above, and thus the description will be omitted.

FIG. 28E is a flowchart which shows an example of using three contexts when the offset information decoding unit 402 decodes the offset processing ON/OFF flag sao_on_flag that is inserted in the slice data.

First, the offset information decoding unit 402 determines whether or not a current signal to be processed is a luma signal (S4021). The offset information decoding unit 402 uses cIdx illustrated in FIG. 28A for determining of the luma signal. Here, when cIdx=0, the current signal is a luma signal.

When the current signal is a luma signal (Yes in S4021), the offset information decoding unit 402 selects and loads the context 1 (S4022). When the current signal is not a luma signal (No in S4021), the offset information decoding unit 402 determines whether or not the current signal is a chroma signal Cb (S4023). The offset information decoding unit 402 uses cIdx for determining of the chroma signal Cb in the same manner as the determining of the luma signal (S4021). Here, when cIdx=1, the current signal is a chroma signal Cb.

When the current signal is the chroma signal Cb (Yes in S4023), the offset information decoding unit 402 selects and loads the context 2 (S4024). When the current signal is not the chroma signal Cb (No in S4023), the offset information decoding unit 402 selects and loads the context 3 (S4025).

Then, the offset information decoding unit 402 decodes the offset processing ON/OFF flag sao_on_flag using the context which is selected and loaded (S4026).

It is to be noted that the flowchart illustrated in FIG. 27E which shows an example of the case where the offset processing ON/OFF flag sao_on_flag that is inserted into APS is decoded is the same as that illustrate in FIG. 28E described above, and thus the description will be omitted.

Through the processes described above, the image coding apparatus and the image decoding apparatus use a different context for each of the luma signal, the chroma signal Cb, and the chroma signal Cr, thereby allocating the symbol occurrence probability according to the feature of each of the signals. Thus, the image coding apparatus and the image decoding apparatus are capable of suppressing the code amount of the offset processing ON/OFF flag sao_on_flag.

It is to be noted that the image coding apparatus and the image decoding apparatus may reduce the number of the contexts to be used for the coding and the decoding to two (a luma signal and a chroma signal) by sharing a context between the chroma signals Cb and Cr.

Embodiment 3

According to Embodiment 2, the image coding apparatus codes information indicating whether or not to perform offset processing for each of the regions to be processed, as the offset processing ON/OFF flag sao_on_flag, at a top of the offset information independently of the pixel classifying method sao_type_idx. When the offset processing is not to be performed, the image coding apparatus does not perform coding on the sao_merge_left_flag or the sao_merge_up_flag which indicates whether or not to copy offset information from a region on the left or above, respectively.

With this, it is possible to suppress the bit amount. An image coding apparatus according to this embodiment, it is further possible to improve throughput by integrating or simplifying arithmetic coding on each item of the offset information.

Examples of the arithmetic coding include bypass arithmetic coding in addition to the context arithmetic coding described in Embodiment 2. The context arithmetic coding uses the adaptive symbol occurrence probability. On the other hand, in the bypass arithmetic coding, the arithmetic coding is performed using the symbol occurrence probability which is 50%. With this, the image coding apparatus does not have to load and update a context in the bypass arithmetic coding, and thus it is possible to speed up the processes.

FIG. 31A illustrates an example of a combination of types of arithmetic coding for use in each syntax element of offset information.

Here, the syntaxes for coding and decoding offset information are the same as the syntaxes in Embodiment 2 illustrated in FIG. 28A and FIG. 28B. In addition, allocation of bits to the offset processing ON/OFF flag sao_on_flag and the pixel classifying method sao_type_idx is equivalent to the allocation according to Embodiment 2 illustrated in FIG. 26. However, allocation of syntax or a bit is not limited to this.

For example, in FIG. 28B, the offset value±sign sao_offset_sign and the band offset coding start category sao_band_position are consecutively coded (decoded) in order to suppress the number of conditional branches corresponding to if statements. However, the order of coding (decoding) is not limited to this. In addition, in the allocation of a bit to the pixel classifying method sao_type_idx illustrated in FIG. 26, a largest bit amount may be allocated to the band offset.

There is strong tendency in the symbol occurrence probability of the offset processing ON/OFF flag sao_on_flag, the left offset information copy flag sao_merge_left_flag, and the upper offset information copy flag sao_merge_up_flag. For that reason, the context arithmetic coding is used.

On the other hand, there is little tendency in the symbol occurrence probability of the pixel classifying method sao_type_idx, the offset absolute value sao_offset, the offset value±sign sao_offset_sign, and the band offset coding start category sao_band_position. For that reason, the bypass arithmetic coding is used.

It is to be noted that the image coding apparatus according to Embodiment 2 uses a different context for each of luma signal, the chroma signal Cb, and the chroma signal Cr in the offset processing ON/OFF flag sao_on_flag and the left offset information copy flag sao_merge_left_flag. With this, the image coding apparatus improves the coding efficiency.

On the other hand, as to the above-described offset information, the image coding apparatus according to this embodiment may share a context among the luma signal, the chroma signal Cb, and the chroma signal Cr in the same manner as the upper offset information copy flag sao_merge_up_flag. With this, it is possible to reduce the number of contexts and the memory size.

FIG. 31B is a table which shows an objective performance of the image coding apparatus and the image decoding apparatus according to this embodiment. FIG. 31B is an index based on NPL 2 and shows that there is little deterioration in the objective performance. The details of the objective performance will be described later.

In this embodiment, operations performed by the offset information coding unit 305 and the offset information decoding unit 402 are different compared with the image coding apparatus and the image decoding apparatus described in Embodiment 2. Other operations are the same as those in Embodiment 2. The following describes the differences.

Figure 32:
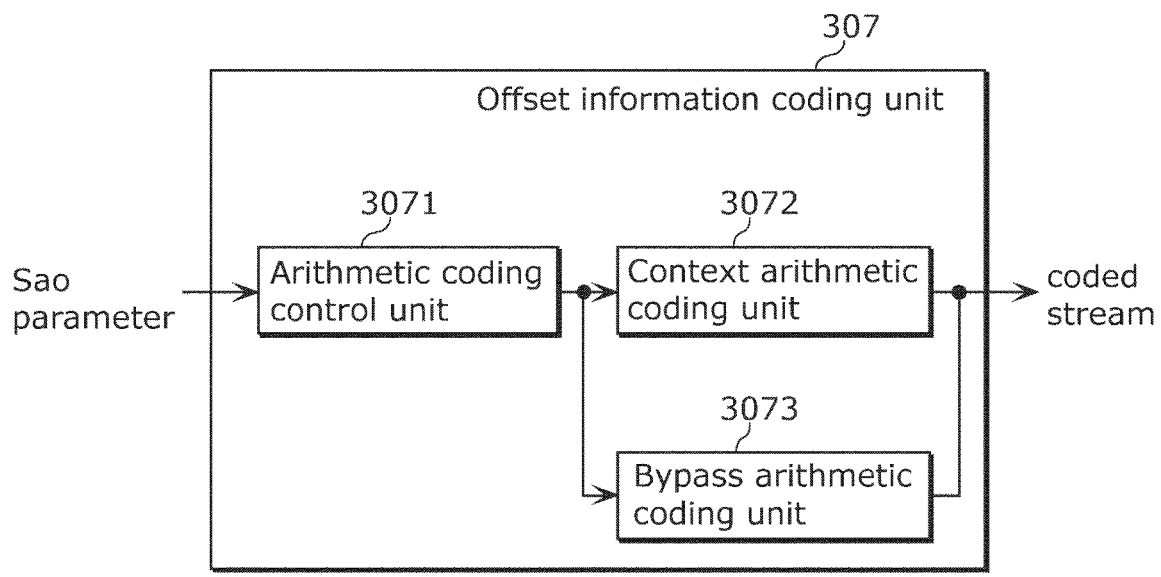
FIG. 32 is a block diagram which illustrates an example of a configuration of an offset information coding unit according to Embodiment 3.

FIG. 32 illustrates a configuration of an offset information coding unit 307 which codes offset information in the image coding apparatus according to this embodiment. The offset information coding unit 307 includes: an arithmetic coding control unit 3071; a context arithmetic coding unit 3072; and a bypass arithmetic coding unit 3073.

The arithmetic coding control unit 3071 switches between the context arithmetic coding and the bypass arithmetic coding to be used according to offset information. It is to be noted that the arithmetic coding control unit 3071 may be included in the control unit 110 of the image coding apparatus 100 illustrated in FIG. 1. The context arithmetic coding unit 3072 loads a context according to the offset information to perform coding. The bypass arithmetic coding unit 3073 performs coding using the symbol occurrence probability which is 50%.

Figure 33:
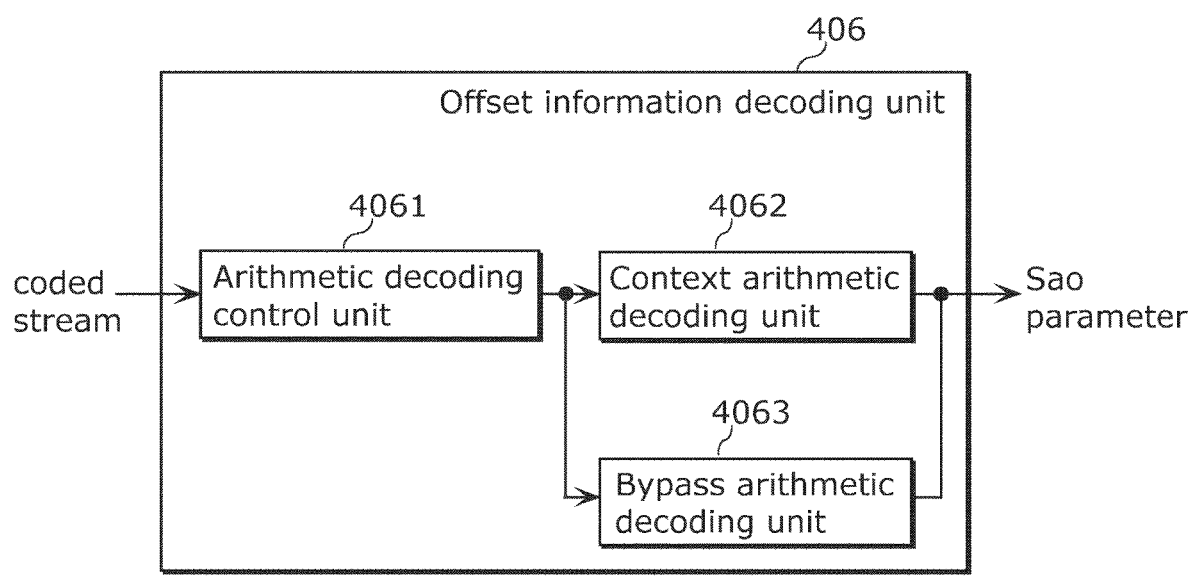
FIG. 33 is a block diagram which illustrates an example of a configuration of an offset information decoding unit according to Embodiment 3.

FIG. 33 illustrates a configuration of an offset information decoding unit 406 which decodes offset information in the image decoding apparatus according to this embodiment. The offset information decoding unit 406 includes: an arithmetic decoding control unit 4061; a context arithmetic decoding unit 4062; and a bypass arithmetic decoding unit 4063.

The arithmetic decoding control unit 4061 switches between the context arithmetic decoding (context adaptive arithmetic decoding) and the bypass arithmetic decoding to be used according to offset information. It is to be noted that the arithmetic decoding control unit 4061 may be included in the control unit 210 of the image decoding apparatus 200 illustrated in FIG. 2. The context arithmetic decoding unit 4062 loads a context according to the offset information to perform decoding. The bypass arithmetic decoding unit 4063 performs decoding using the symbol occurrence probability which is 50%.

Figure 34:
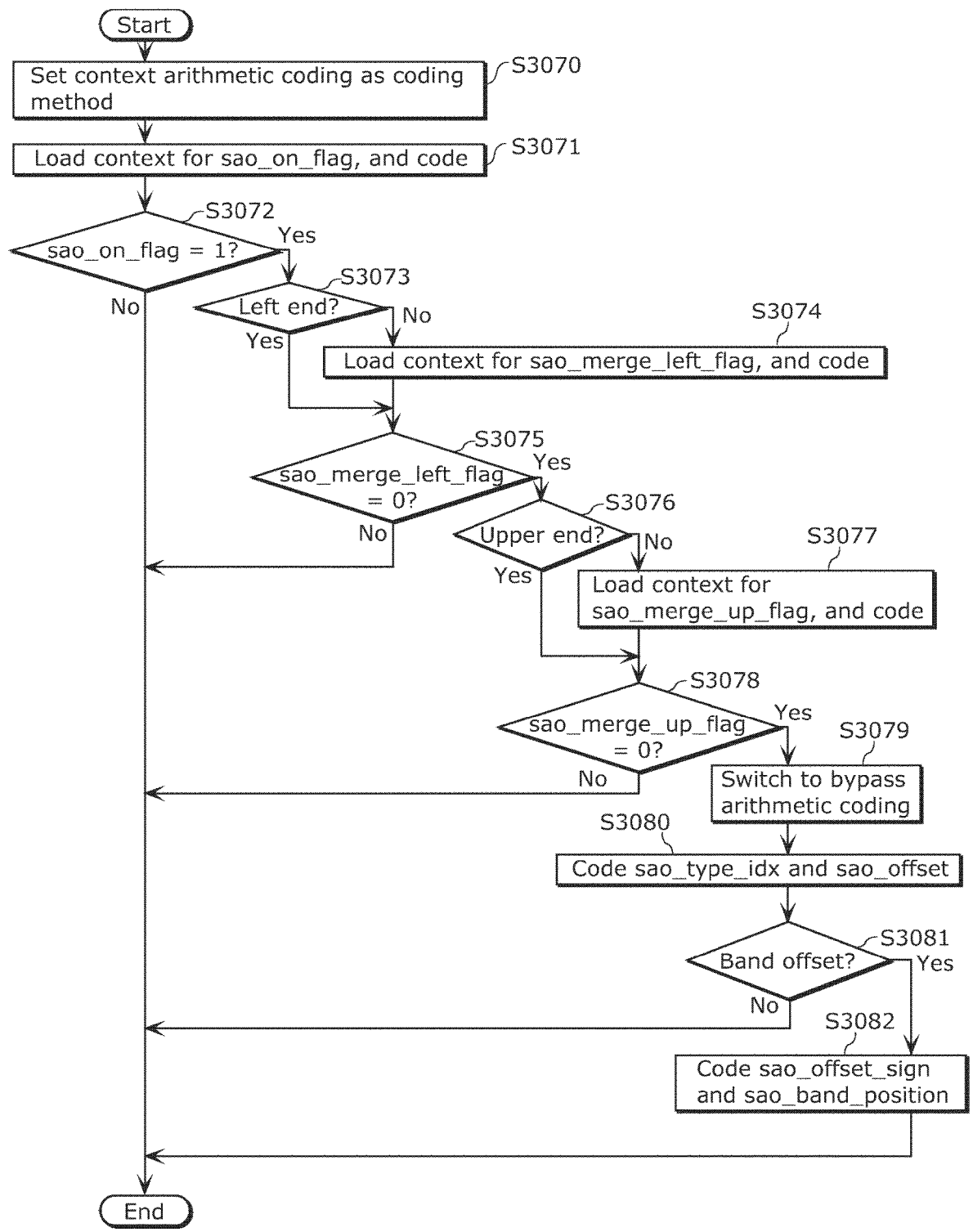
FIG. 34 is a flowchart which illustrates an example of operations of the offset information coding unit according to Embodiment 3.

FIG. 34 is a flowchart illustrating an example of coding offset information using arithmetic coding, performed by the offset information coding unit 307.

First, upon starting of processing by the offset information coding unit 307, the arithmetic coding control unit 3071 sets the context arithmetic coding as the coding method (S3070).

Then, the context arithmetic coding unit 3072 loads a context for the offset processing ON/OFF flag sao_on_flag, and codes the offset processing ON/OFF flag sao_on_flag using the context (S3071).

Next, the arithmetic coding control unit 3071 determines whether or not the offset processing ON/OFF flag sao_on_flag indicates 1 (S3072). Here, it indicates that the offset processing is not to be performed on the target region to be processed when the sao_on_flag indicates 0, and it indicates that the offset processing is to be performed on the target region when the sao_on_flag indicates 1.

When the offset processing ON/OFF flag sao_on_flag indicates 1 (Yes is S3072), the arithmetic coding control unit 3071 determines whether or not the target region is positioned at the left end of a slice or a tile (S3073). The offset information is copied only from a region in the same slice and the same tile. For that reason, the above-described determination is performed prior to coding of the left offset information copy flag sao_merge_left_flag.

When the target region is not positioned at the left end (No in S3073), the context arithmetic coding unit 3072 loads a context for the left offset information copy flag sao_merge_left_flag. Then, the context arithmetic coding unit 3072 codes the left offset information copy flag sao_merge_left_flag (S3074).

When the target region is positioned at the left end (Yes in S3073) or subsequently to coding of the sao_merge_left_flag (S3074), the arithmetic coding control unit 3071 determines whether or not the sao_merge_left_flag is 0 (S3075). Here, the sao_merge_left_flag being 0 indicates that the offset information is not copied from the left region, and the sao_merge_left_flag being 1 indicates that the offset information is copied from the left region.

It is to be noted that, when coding of the sao_merge_left_flag (S3074) is not performed, a value of the sao_merge_left_flag does not exist. In this case, the values of the sao_merge_left_flag is processed as 0. In addition, the offset information coding unit 307 may secure a memory for the sao_merge_left_flag at the time of starting a process, and set an initial value 0.

Next, when the sao_merge_left_flag indicates 0 (Yes is S3075), the arithmetic coding control unit 3071 determines whether or not the target region is positioned at the upper end of a slice or a tile (S3076). Since the offset information is copied only from a region in the same slice and in the same tile as with the determination of the left end (S3073), the above-described determination is performed prior to coding of the upper offset information copy flag sao_merge_up_flag.

When the target region is not positioned at the upper end (No in S3076), the context arithmetic coding unit 3072 loads a context for the upper offset information copy flag sao_merge_up_flag. Then, the context arithmetic coding unit 3072 codes the upper offset information copy flag sao_merge_up_flag (S3077).

When the target region is positioned at the upper end (Yes in S3076) or subsequently to coding of the sao_merge_up_flag (S3077), the arithmetic coding control unit 3071 determines whether or not the sao_merge_up_flag is 0 (S3078). Here, the sao_merge_up_flag being 0 indicates that the offset information is not copied from the upper region, and the sao_merge_up_flag being 1 indicates that the offset information is copied from the upper region.

It is to be noted that, when coding of the sao_merge_up_flag (S3077) is not performed, a value of the sao_merge_up_flag does not exist. In this case, the value of the sao_merge_up_flag is processed as 0. In addition, the offset information coding unit 307 may secure a memory for the sao_merge_up_flag at the time of starting a process, and set an initial value 0.

Next, when the sao_merge_up_flag indicates 0 (Yes is S3078), the arithmetic coding control unit 3071 switches the coding method to the bypass arithmetic coding (S3079). With this, the bypass arithmetic coding is used throughout the subsequent coding steps.

Next, the bypass arithmetic coding unit 3073 codes the pixel classifying method sao_type_idx and the offset absolute value sao_offset (S3080). Here, in this embodiment, the number of offset absolute values sao_offset is four in any of the pixel classifying methods. However, the bypass arithmetic coding unit 3073 may code offset absolute values which are different in number for each of the pixel classifying methods.

Then, the arithmetic coding control unit 3071 determines whether or not the pixel classifying method is the band offset (S3081). Here, the arithmetic coding control unit 3071 uses the pixel classifying method sao_type_idx for determination.

According to this embodiment, the band offset is allocated with 0 as a value of sao_type_idx. For that reason, the arithmetic coding control unit 3071 determines that the pixel classifying method is the band offset when sao_type_idx is 0, and that the pixel classifying method is not the band offset when sao_type_idx is other than 0.

When the pixel classifying method is the band offset (Yes in S30841), the bypass arithmetic coding unit 3073 codes the offset value±sign sao_offset_sign and the band offset coding start category sao_band_position (S3082).

It is to be noted that, in this embodiment, the bypass arithmetic coding unit 3073 codes the offset value±sign sao_offset_sign only in the case of the band offset. However, the bypass arithmetic coding unit 3073 may code the offset value±sign sao_offset_sign in the case of the edge offset as well. In this case, the offset value±sign sao_offset_sign is coded in Step S3080.

Further in this case, in Step S3080, the offset absolute value sao_offset and the offset value±sign sao_offset_sign may be integrated and coded as an offset value.

Figure 35:
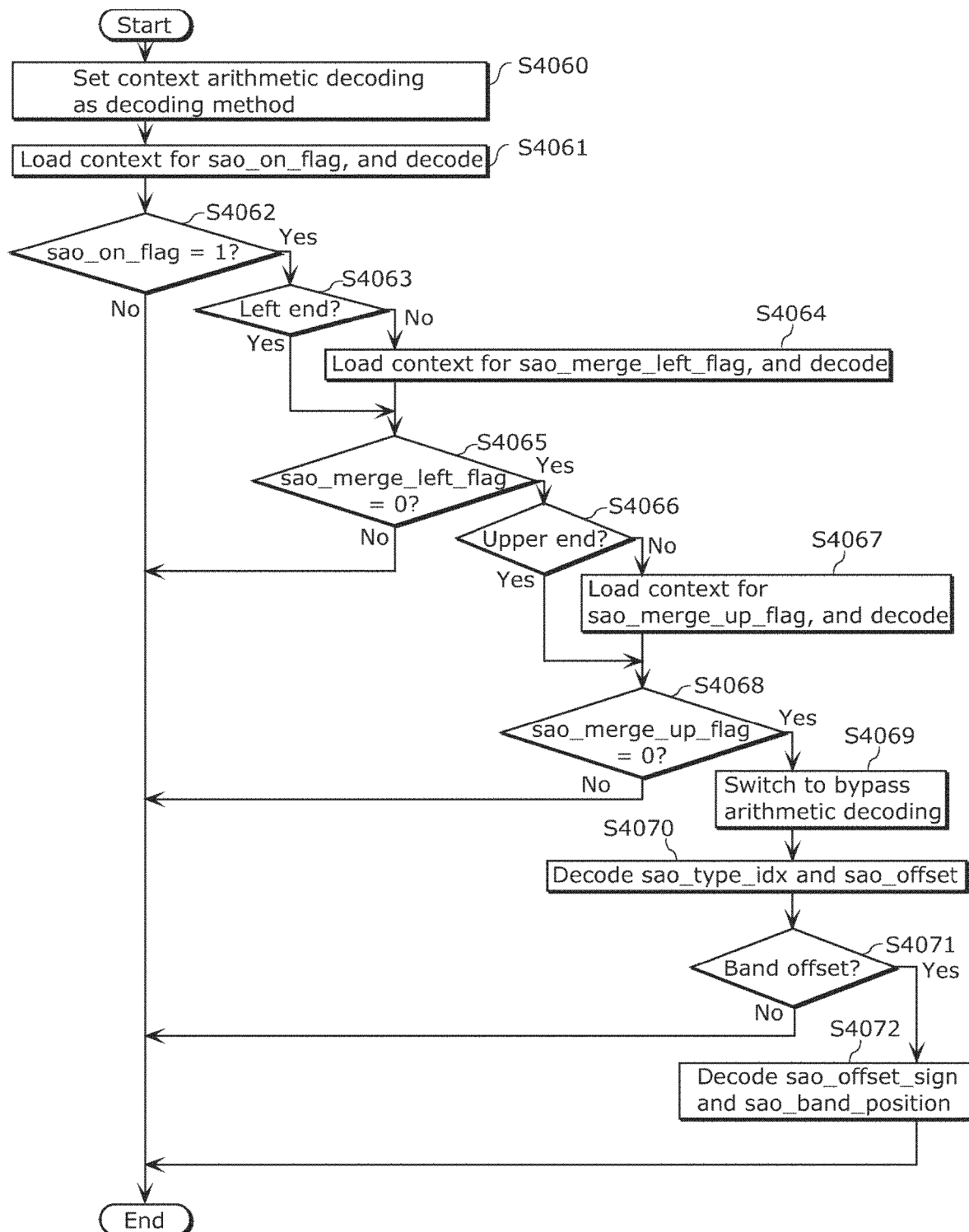
FIG. 35 is a flowchart which illustrates an example of operations of the offset information decoding unit according to Embodiment 3.

FIG. 35 is a flowchart which shows an example of decoding the offset information using the arithmetic decoding performed by the offset information decoding unit 406.

First, upon starting of processing by the offset information decoding unit 406, the arithmetic decoding control unit 4061 sets the context arithmetic decoding as a decoding method (S4060).

Then, the context arithmetic decoding unit 4062 loads a context for the offset processing ON/OFF flag sao_on_flag, and decodes the offset processing ON/OFF flag sao_on_flag using the context (S4061).

Next, the arithmetic decoding control unit 4061 determines whether or not the offset processing ON/OFF flag sao_on_flag indicates 1 (S4062). Here, it indicates that the offset processing is not to be performed on the target region to be processed when the sao_on_flag indicates 0, and it indicates that the offset processing is to be performed on the target region when the sao_on_flag indicates 1.

Next, when sao_on_flag indicates 1 (Yes is S4062), the arithmetic decoding control unit 4061 determines whether or not the target region is positioned at the left end of a slice or a tile (S4063). The offset information is copied only from a region in the same slice and the same tile. For that reason, the above-described determination is performed prior to decoding of the left offset information copy flag sao_merge_left_flag.

When the target region is not positioned at the left end (No in S4063), the context arithmetic decoding unit 4062 loads a context for the left offset information copy flag sao_merge_left_flag. Then, the context arithmetic decoding unit 4062 decodes the left offset information copy flag sao_merge_left_flag (S4064).

When the target region is positioned at the left end (Yes in S4063) or subsequently to decoding of the sao_merge_left_flag (S4064), the arithmetic decoding control unit 4061 determines whether or not the sao_merge_left_flag is 0 (S4065). Here, the sao_merge_left_flag being 0 indicates that the offset information is not copied from the left region, and the sao_merge_left_flag being 1 indicates that the offset information is copied from the left region.

It is to be noted that, when decoding of the sao_merge_left_flag (S4064) is not performed, a value of the sao_merge_left_flag does not exist. In this case, the values of the sao_merge_left_flag is processed as 0. In addition, the offset information decoding unit 406 may secure a memory for sao_merge_left_flag at the time of starting a process, and set an initial value 0.

Next, when sao_merge_left_flag indicates 0 (Yes is S4065), the arithmetic decoding control unit 4061 determines whether or not the target region is positioned at the upper end of a slice or a tile (S4066). Since the offset information is copied only from a region in the same slice and in the same tile as with the determination of the left end (S4063), the above-described determination is performed prior to decoding of the upper offset information copy flag sao_merge_up_flag.

When the target region is not positioned at the upper end (No in S4066), the context arithmetic decoding unit 4062 loads a context for the upper offset information copy flag sao_merge_up_flag. Then, the context arithmetic decoding unit 4062 decodes the upper offset information copy flag sao_merge_up_flag (S4067).

When the target region is positioned at the upper end (Yes in S4066) or subsequently to decoding of the sao_merge_up_flag (S4067), the arithmetic decoding control unit 4061 determines whether or not the sao_merge_up_flag is 0 (S4068). Here, the sao_merge_up_flag being 0 indicates that the offset information is not copied from the upper region, and the sao_merge_up_flag being 1 indicates that the offset information is copied from the upper region.

It is to be noted that, when decoding of the sao_merge_up_flag (S4067) is not performed, a value of the sao_merge_up_flag does not exist. In this case, the value of the sao_merge_up_flag is processed as 0. In addition, the offset information decoding unit 406 may secure a memory for sao_merge_up_flag at the time of starting a process, and set an initial value 0.

Next, when sao_merge_up_flag indicates 0 (Yes is S4068), the arithmetic decoding control unit 4061 switches the decoding method to the bypass arithmetic decoding (S4069). With this, the bypass arithmetic decoding is used throughout the subsequent decoding steps.

Next, the bypass arithmetic decoding unit 4063 decodes the pixel classifying method sao_type_idx and the offset absolute value sao_offset (S4070). Here, in this embodiment, the number of offset absolute values sao_offset is four in any of the pixel classifying methods. However, the bypass arithmetic decoding unit 4063 may decode offset absolute values which are different in number for each of the pixel classifying methods.

Then, the arithmetic decoding control unit 4061 determines whether or not the pixel classifying method is the band offset (S4071). Here, the arithmetic decoding control unit 4061 uses the pixel classifying method sao_type_idx for determination.

According to this embodiment, the band offset is allocated with 0 as a value of sao_type_idx. For that reason, the arithmetic decoding control unit 4061 determines that the pixel classifying method is the band offset when sao_type_idx is 0, and that the pixel classifying method is not the band offset when sao_type_idx is other than 0.

When the pixel classifying method is the band offset (Yes in S4071), the bypass arithmetic decoding unit 4063 decodes the offset value±sign sao_offset_sign and the band offset coding start category sao_band_position (S4072).

It is to be noted that, in this embodiment, the bypass arithmetic decoding unit 4063 decodes the offset value±sign sao_offset_sign only in the case the band offset. However, the bypass arithmetic decoding unit 4063 may decode the offset value±sign sao_offset_sign in the case of the edge offset as well. In this case, the offset value±sign sao_offset_sign is decoded in Step S4070.

Further in this case, in Step S4070, the offset absolute value sao_offset and the offset value±sign sao_offset_sign may be integrated and decoded as an offset value.

As described above, the bypass arithmetic coding and the bypass arithmetic decoding are used for coding and decoding of all of the parameters following the top three parameters of the offset processing ON/OFF flag sao_on_flag, the left offset information copy flag sao_merge_left_flag, and the upper offset information copy flag sao_merge_up_flag. This eliminates the need for the image coding apparatus and the image decoding apparatus to load and update contexts everywhere. Therefore, the throughput is improved.

Figure 36:
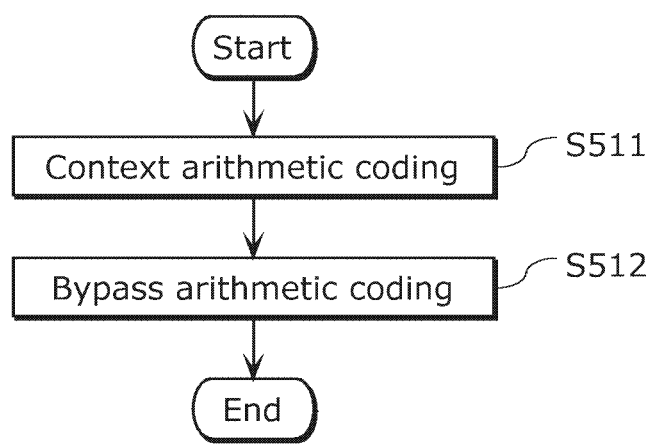
FIG. 36 is a flowchart which illustrates an example of a feature of coding according to Embodiment 3.

FIG. 36 is a flowchart which shows an example of the feature of the above-described coding. First, the context arithmetic coding unit 3072 consecutively codes the first information and the second information by the context arithmetic coding (S511). The context arithmetic coding is arithmetic coding which uses a variable probability. The first information indicates whether or not to perform, for the first region of an image, a sample adaptive offset (SAO) processing that is offset processing on a pixel value. The second information indicates whether or not to use, in the SAO processing for the first region, information of the SAO processing for a region other than the first region.

Next, the bypass arithmetic coding unit 3073, after the first information and the second information are coded, codes other information by the bypass arithmetic coding (S512). The bypass arithmetic coding is arithmetic coding which uses a fixed probability. Other information is information on the SAO processing for the first region and different from the first information or the second information.

Figure 37:
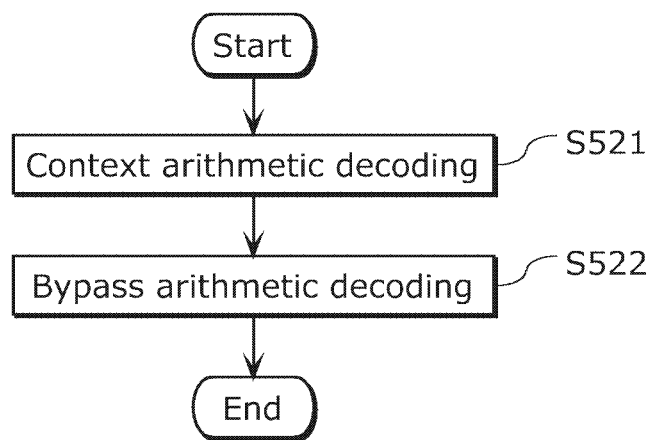
FIG. 37 is a flowchart which illustrates an example of a feature of decoding according to Embodiment 3.

FIG. 37 is a flowchart which shows an example of the feature of the above-described decoding. First, the context arithmetic decoding unit 4062 consecutively decodes the first information and the second information by the context arithmetic decoding (S521). The context arithmetic decoding is arithmetic decoding which uses a variable probability. The first information indicates whether or not to perform, for the first region of an image, the sample adaptive offset (SAO) processing that is an offset processing on a pixel value. The second information indicates whether or not to use, in the SAO processing for the first region, information of the SAO processing for a region other than the first region.

Next, the bypass arithmetic decoding unit 4063, after the first information and the second information are decoded, decodes other information by the bypass arithmetic decoding (S522). The bypass arithmetic decoding is arithmetic decoding which uses a fixed probability. Other information is information on the SAO processing for the first region and different from the first information or the second information.

It is to be noted that either the first information or the second information may be coded first. Likewise, either the first information or the second information may be decoded first.

In addition, the order of coding is an order in which information is written into a coded stream as a sign (code), and the order of decoding is an order in which a sign (code) is read from a coded stream as information. Thus, the order of coding and decoding exemplified above with reference to several diagrams corresponds to the order of information in a coded stream. In addition, the order of syntax elements exemplified above with reference to several diagrams corresponds to the order of information in a coded stream and to the order of coding and decoding.

In addition, the image coding apparatus may be an apparatus which performs only the processes illustrated in FIG. 36. Likewise, the image decoding apparatus may be an apparatus which performs only the processes illustrated in FIG. 37. Other processes may be performed by other apparatuses.

FIG. 31B illustrates a result based on test conditions specified in the HEVC standard (see NPL 2) as an objective performance.

In FIG. 31B, Configuration indicates coding parameter setting conditions. BD-rate indicates an objective index calculated from a peak signal-to-noise ratio (PSNR) of a reconstructed image and a code amount of a coded stream. A negative BD-rate indicates improvement in the objective performance, and a positive BD-rate indicates deterioration in the objective performance. It is to be noted that the BD-rate in FIG. 31B indicates improvement or deterioration in the objective performance of this embodiment based on comparison with Embodiment 1.

As illustrated in FIG. 31B, the BD-rate falls within a range of ±0.1. This indicates that the objective performance of this embodiment is substantially equivalent to the objective performance of Embodiment 1. More specifically, in this embodiment, there is little deterioration in the objective performance and the throughput is improved.

As described above, the image coding apparatus according to this embodiment is capable of coding an image with high processing efficiency. In addition, the image decoding apparatus according to this embodiment is capable of decoding an image with high processing efficiency.

Each of the structural elements in each of the above-described embodiments may be configured in the form of an exclusive hardware product, or may be realized by executing a software program suitable for the structural element. Each of the structural elements may be realized by means of a program executing unit, such as a CPU and a processor, reading and executing the software program recorded on a recording medium such as a hard disk or a semiconductor memory.

In other words, the image coding apparatus and the image decoding apparatus include control circuitry and storage which is electrically connected to the control circuitry (which is accessible from the control circuitry). The control circuitry includes at least one of the exclusive hardware product and the program executing unit. In addition, when the control circuitry includes the program executing unit, the storage stores a software program that is executed by the program executing unit.

Here, software that accomplishes the image coding apparatus according to each of the above-described embodiments is a program as below.

More specifically, this program causes a computer to execute an image coding method which includes: performing context arithmetic coding to consecutively code (i) first information indicating whether or not to perform sample adaptive offset (SAO) processing for a first region of an image and (ii) second information indicating whether or not to use, in the SAO processing for the first region, information on SAO processing for a region other than the first region, the context arithmetic coding being arithmetic coding using a variable probability, the SAO processing being offset processing on a pixel value; and performing bypass arithmetic coding to code other information which is information on the SAO processing for the first region and different from the first information or the second information, after the first information and the second information are coded, the bypass arithmetic coding being arithmetic coding using a fixed probability.

In addition, this program may cause a computer to execute an image decoding method which includes: performing context arithmetic decoding to consecutively decode (i) first information indicating whether or not to perform sample adaptive offset (SAO) processing for a first region of an image and (ii) second information indicating whether or not to use, in the SAO processing for the first region, information on SAO processing for a region other than the first region, the context arithmetic decoding being arithmetic decoding using a variable probability, the SAO processing being offset processing on a pixel value; and performing bypass arithmetic decoding to decode other information which is information on the SAO processing for the first region and different from the first information or the second information, after the first information and the second information are decoded, the bypass arithmetic decoding being arithmetic decoding using a fixed probability.

In addition, each of the structural elements may be a circuit. The circuitries may be configured as a single circuit as a whole or may be mutually different circuits. In addition, each of the structural elements may be implemented as a general purpose processor or as a dedicated processor.

Although only some exemplary embodiments have been described above, the scope of the Claims of the present application is not limited to these embodiments. Those skilled in the art will readily appreciate that various modifications may be made in these exemplary embodiments and that other embodiments may be obtained by arbitrarily combining the structural elements of the embodiments without materially departing from the novel teachings and advantages of the subject matter recited in the appended Claims. Thus, such modifications and other embodiments are also included in the present disclosure.

For example, an image coding and decoding apparatus may include the image coding apparatus and the image decoding apparatus. In addition, processes executed by a specific processing unit may be performed a different processing unit. Furthermore, the order in which processes are performed may be changed, or a plurality of processes may be performed in parallel. Furthermore, a dedicated or a common storage unit for storing a variety of information items may be added to the configuration.

Embodiment 4

The processing described in each of embodiments can be simply implemented in an independent computer system, by recording, in a recording medium, a program for implementing the configurations of the moving picture coding method (image coding method) and the moving picture decoding method (image decoding method) described in each of embodiments. The recording media may be any recording media as long as the program can be recorded, such as a magnetic disk, an optical disk, a magnetic optical disk, an IC card, and a semiconductor memory.

Hereinafter, the applications to the moving picture coding method (image coding method) and the moving picture decoding method (image decoding method) described in each of embodiments and systems using thereof will be described. The system has a feature of having an image coding and decoding apparatus that includes an image coding apparatus using the image coding method and an image decoding apparatus using the image decoding method. Other configurations in the system can be changed as appropriate depending on the cases.

Figure 38:
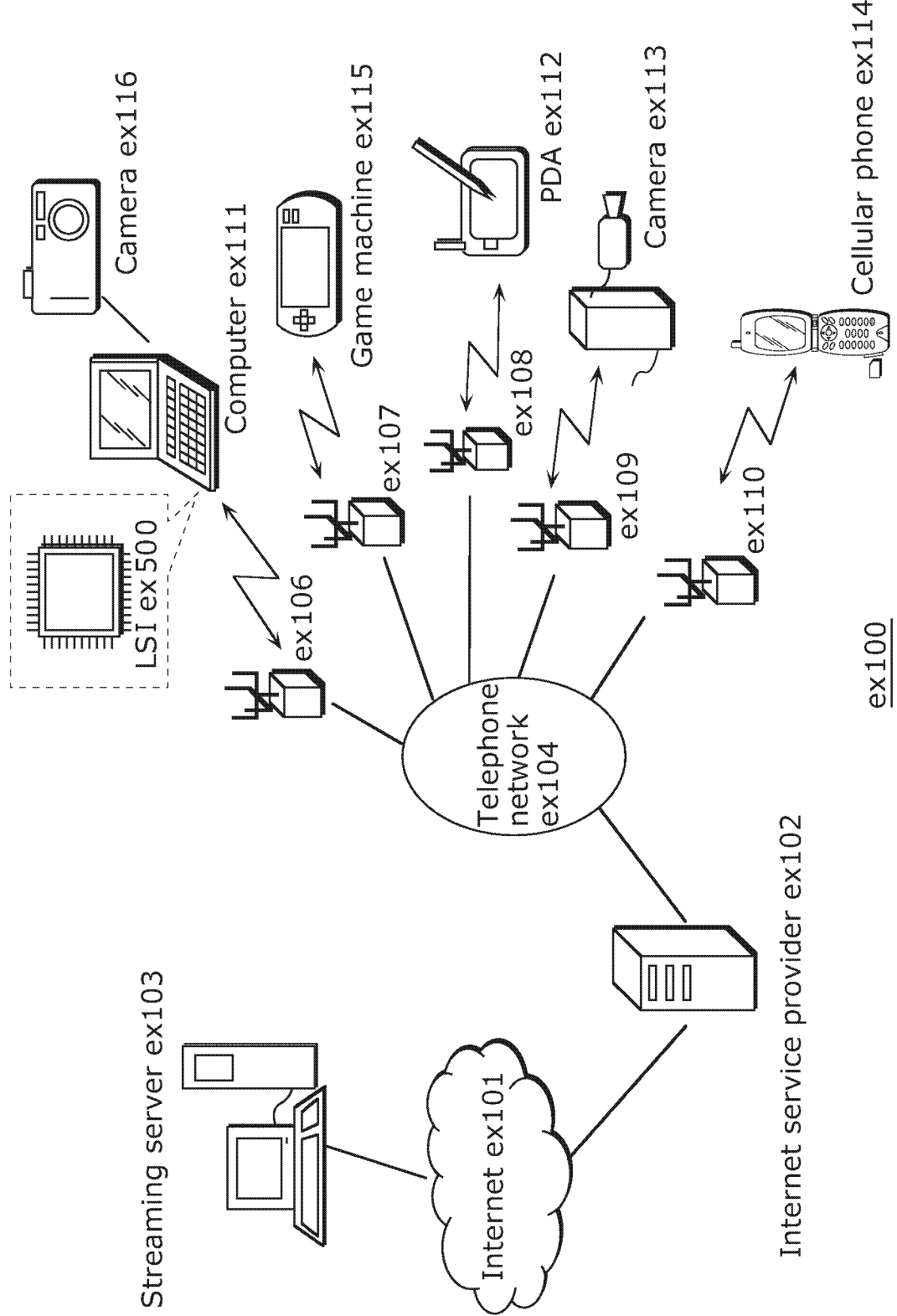
FIG. 38 shows an overall configuration of a content providing system for implementing content distribution services.

FIG. 38 illustrates an overall configuration of a content providing system ex100 for implementing content distribution services. The area for providing communication services is divided into cells of desired size, and base stations ex106, ex107, ex108, ex109, and ex110 which are fixed wireless stations are placed in each of the cells.

The content providing system ex100 is connected to devices, such as a computer ex111, a personal digital assistant (PDA) ex112, a camera ex113, a cellular phone ex114 and a game machine ex115, via the Internet ex101, an Internet service provider ex102, a telephone network ex104, as well as the base stations ex106 to ex110, respectively.

However, the configuration of the content providing system ex100 is not limited to the configuration shown in FIG. 38, and a combination in which any of the elements are connected is acceptable. In addition, each device may be directly connected to the telephone network ex104, rather than via the base stations ex106 to ex110 which are the fixed wireless stations. Furthermore, the devices may be interconnected to each other via a short distance wireless communication and others.

The camera ex113, such as a digital video camera, is capable of capturing video. A camera ex116, such as a digital camera, is capable of capturing both still images and video. Furthermore, the cellular phone ex114 may be the one that meets any of the standards such as Global System for Mobile Communications (GSM) (registered trademark), Code Division Multiple Access (CDMA), Wideband-Code Division Multiple Access (W-CDMA), Long Term Evolution (LTE), and High Speed Packet Access (HSPA). Alternatively, the cellular phone ex114 may be a Personal Handyphone System (PHS).

In the content providing system ex100, a streaming server ex103 is connected to the camera ex113 and others via the telephone network ex104 and the base station ex109, which enables distribution of images of a live show and others. In such a distribution, a content (for example, video of a music live show) captured by the user using the camera ex113 is coded as described above in each of embodiments (i.e., the camera functions as the image coding apparatus according to an aspect of the present disclosure), and the coded content is transmitted to the streaming server ex103. On the other hand, the streaming server ex103 carries out stream distribution of the transmitted content data to the clients upon their requests. The clients include the computer ex111, the PDA ex112, the camera ex113, the cellular phone ex114, and the game machine ex115 that are capable of decoding the above-mentioned coded data. Each of the devices that have received the distributed data decodes and reproduces the coded data (i.e., functions as the image decoding apparatus according to an aspect of the present disclosure).

The captured data may be coded by the camera ex113 or the streaming server ex103 that transmits the data, or the coding processes may be shared between the camera ex113 and the streaming server ex103. Similarly, the distributed data may be decoded by the clients or the streaming server ex103, or the decoding processes may be shared between the clients and the streaming server ex103. Furthermore, the data of the still images and video captured by not only the camera ex113 but also the camera ex116 may be transmitted to the streaming server ex103 through the computer ex111. The coding processes may be performed by the camera ex116, the computer ex111, or the streaming server ex103, or shared among them.

Furthermore, the coding and decoding processes may be performed by an LSI ex500 generally included in each of the computer ex111 and the devices. The LSI ex500 may be configured of a single chip or a plurality of chips. Software for coding and decoding video may be integrated into some type of a recording medium (such as a CD-ROM, a flexible disk, and a hard disk) that is readable by the computer ex111 and others, and the coding and decoding processes may be performed using the software. Furthermore, when the cellular phone ex114 is equipped with a camera, the video data obtained by the camera may be transmitted. The video data is data coded by the LSI ex500 included in the cellular phone ex114.

Furthermore, the streaming server ex103 may be composed of servers and computers, and may decentralize data and process the decentralized data, record, or distribute data.

As described above, the clients may receive and reproduce the coded data in the content providing system ex100. In other words, the clients can receive and decode information transmitted by the user, and reproduce the decoded data in real time in the content providing system ex100, so that the user who does not have any particular right and equipment can implement personal broadcasting.

Figure 39:
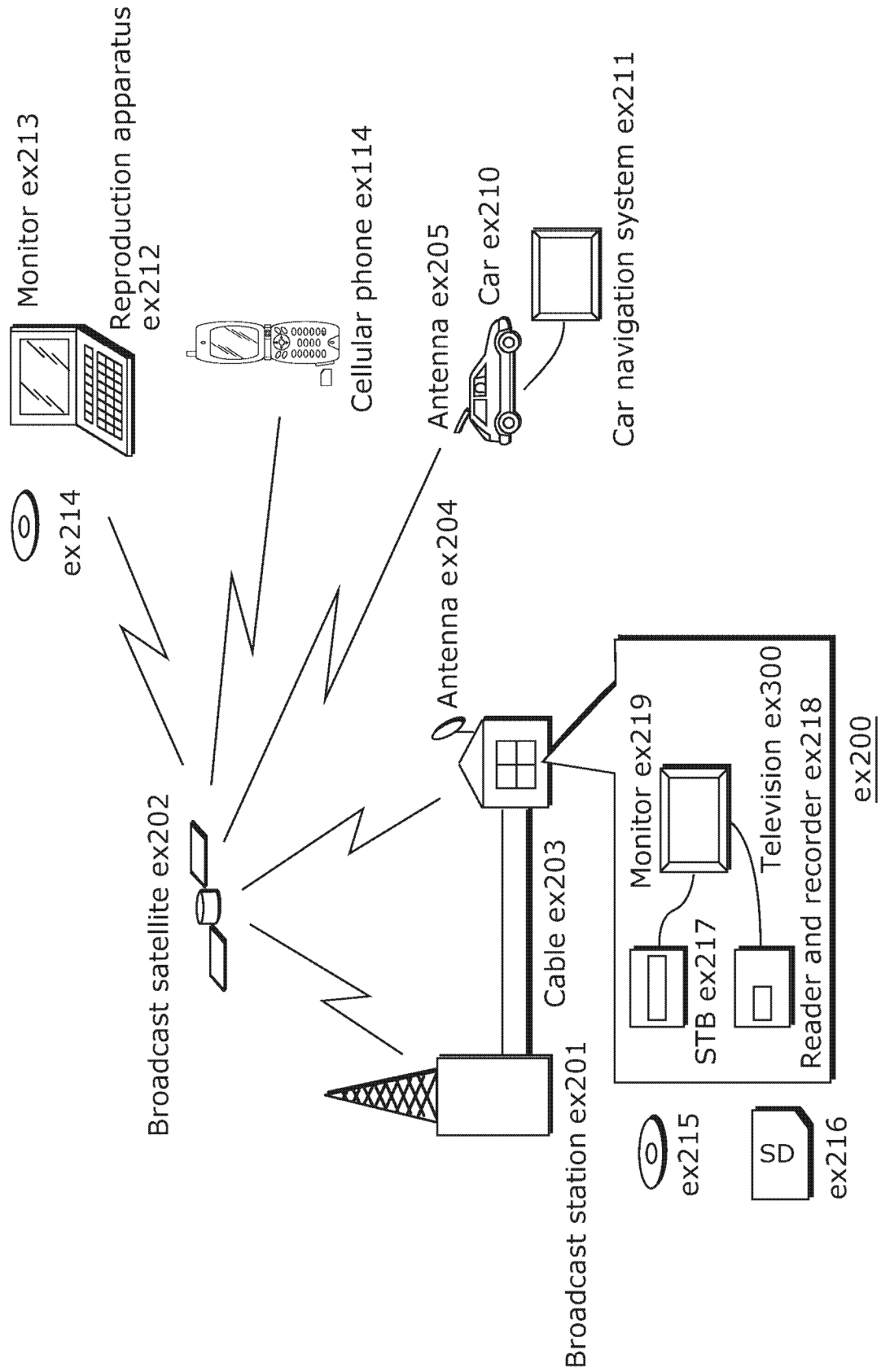
FIG. 39 shows an overall configuration of a digital broadcasting system.

Aside from the example of the content providing system ex100, at least one of the moving picture coding apparatus (image coding apparatus) and the moving picture decoding apparatus (image decoding apparatus) described in each of embodiments may be implemented in a digital broadcasting system ex200 illustrated in FIG. 39. More specifically, a broadcast station ex201 communicates or transmits, via radio waves to a broadcast satellite ex202, multiplexed data obtained by multiplexing audio data and others onto video data. The video data is data coded by the moving picture coding method described in each of embodiments (i.e., data coded by the image coding apparatus according to an aspect of the present disclosure). Upon receipt of the multiplexed data, the broadcast satellite ex202 transmits radio waves for broadcasting. Then, a home-use antenna ex204 with a satellite broadcast reception function receives the radio waves. Next, a device such as a television (receiver) ex300 and a set top box (STB) ex217 decodes the received multiplexed data, and reproduces the decoded data (i.e., functions as the image decoding apparatus according to an aspect of the present disclosure).

Furthermore, a reader/recorder ex218 (i) reads and decodes the multiplexed data recorded on a recording medium ex215, such as a DVD and a BD, or (i) codes video signals in the recording medium ex215, and in some cases, writes data obtained by multiplexing an audio signal on the coded data. The reader/recorder ex218 can include the moving picture decoding apparatus or the moving picture coding apparatus as shown in each of embodiments. In this case, the reproduced video signals are displayed on the monitor ex219, and can be reproduced by another device or system using the recording medium ex215 on which the multiplexed data is recorded. It is also possible to implement the moving picture decoding apparatus in the set top box ex217 connected to the cable ex203 for a cable television or to the antenna ex204 for satellite and/or terrestrial broadcasting, so as to display the video signals on the monitor ex219 of the television ex300. The moving picture decoding apparatus may be implemented not in the set top box but in the television ex300.

Figure 40:
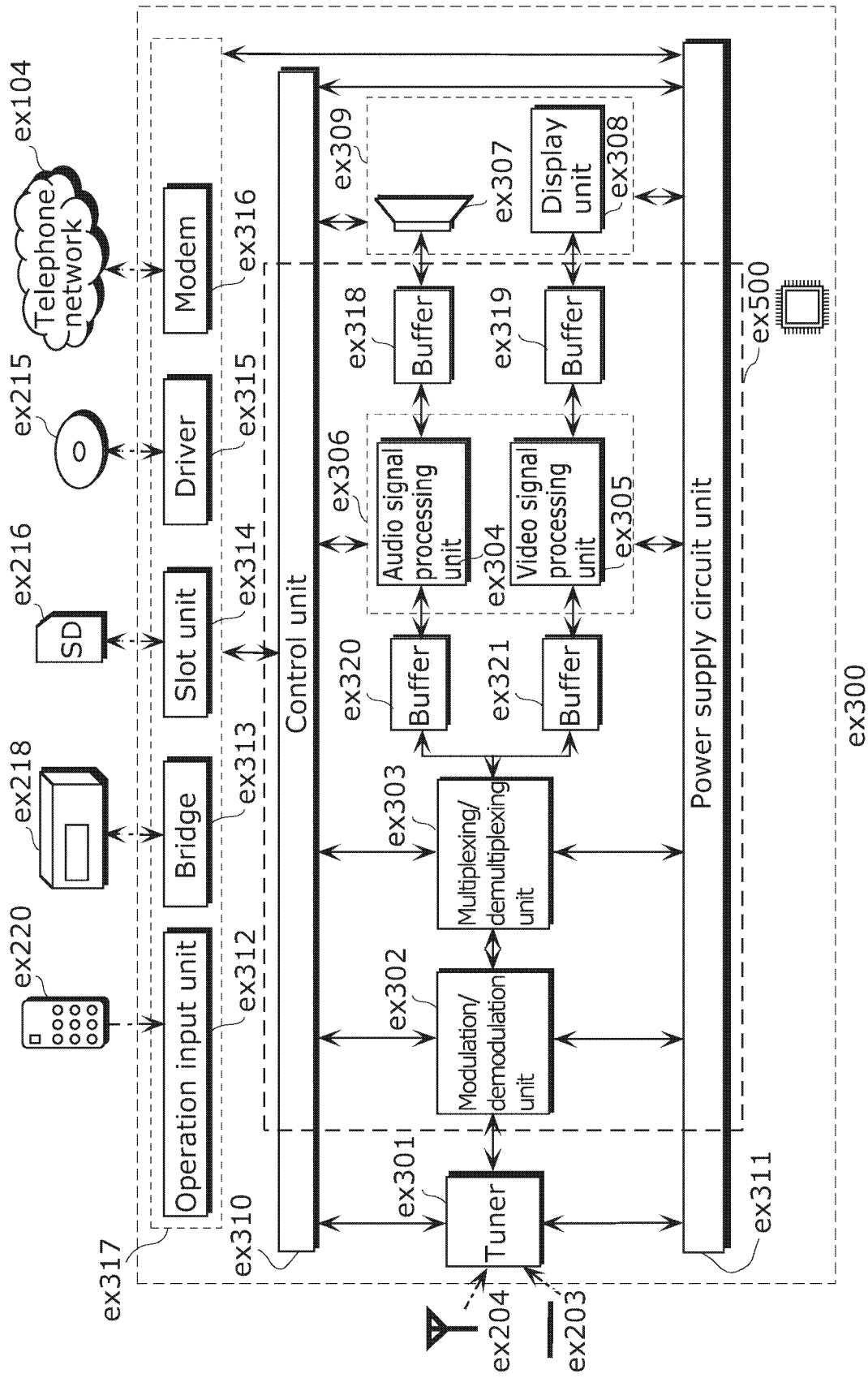
FIG. 40 shows a block diagram illustrating an example of a configuration of a television.

FIG. 40 illustrates the television (receiver) ex300 that uses the moving picture coding method and the moving picture decoding method described in each of embodiments. The television ex300 includes: a tuner ex301 that obtains or provides multiplexed data obtained by multiplexing audio data onto video data, through the antenna ex204 or the cable ex203, etc. that receives a broadcast; a modulation/demodulation unit ex302 that demodulates the received multiplexed data or modulates data into multiplexed data to be supplied outside; and a multiplexing/demultiplexing unit ex303 that demultiplexes the modulated multiplexed data into video data and audio data, or multiplexes video data and audio data coded by a signal processing unit ex306 into data.

The television ex300 further includes: a signal processing unit ex306 including an audio signal processing unit ex304 and a video signal processing unit ex305 that decode audio data and video data and code audio data and video data, respectively (which function as the image coding apparatus and the image decoding apparatus according to the aspects of the present disclosure); and an output unit ex309 including a speaker ex307 that provides the decoded audio signal, and a display unit ex308 that displays the decoded video signal, such as a display. Furthermore, the television ex300 includes an interface unit ex317 including an operation input unit ex312 that receives an input of a user operation. Furthermore, the television ex300 includes a control unit ex310 that controls overall each constituent element of the television ex300, and a power supply circuit unit ex311 that supplies power to each of the elements. Other than the operation input unit ex312, the interface unit ex317 may include: a bridge ex313 that is connected to an external device, such as the reader/recorder ex218; a slot unit ex314 for enabling attachment of the recording medium ex216, such as an SD card; a driver ex315 to be connected to an external recording medium, such as a hard disk; and a modem ex316 to be connected to a telephone network. Here, the recording medium ex216 can electrically record information using a non-volatile/volatile semiconductor memory element for storage. The constituent elements of the television ex300 are connected to each other through a synchronous bus.

First, the configuration in which the television ex300 decodes multiplexed data obtained from outside through the antenna ex204 and others and reproduces the decoded data will be described. In the television ex300, upon a user operation through a remote controller ex220 and others, the multiplexing/demultiplexing unit ex303 demultiplexes the multiplexed data demodulated by the modulation/demodulation unit ex302, under control of the control unit ex310 including a CPU. Furthermore, the audio signal processing unit ex304 decodes the demultiplexed audio data, and the video signal processing unit ex305 decodes the demultiplexed video data, using the decoding method described in each of embodiments, in the television ex300. The output unit ex309 provides the decoded video signal and audio signal outside, respectively. When the output unit ex309 provides the video signal and the audio signal, the signals may be temporarily stored in buffers ex318 and ex319, and others so that the signals are reproduced in synchronization with each other. Furthermore, the television ex300 may read multiplexed data not through a broadcast and others but from the recording media ex215 and ex216, such as a magnetic disk, an optical disk, and a SD card. Next, a configuration in which the television ex300 codes an audio signal and a video signal, and transmits the data outside or writes the data on a recording medium will be described. In the television ex300, upon a user operation through the remote controller ex220 and others, the audio signal processing unit ex304 codes an audio signal, and the video signal processing unit ex305 codes a video signal, under control of the control unit ex310 using the coding method described in each of embodiments. The multiplexing/demultiplexing unit ex303 multiplexes the coded video signal and audio signal, and provides the resulting signal outside. When the multiplexing/demultiplexing unit ex303 multiplexes the video signal and the audio signal, the signals may be temporarily stored in the buffers ex320 and ex321, and others so that the signals are reproduced in synchronization with each other. Here, the buffers ex318, ex319, ex320, and ex321 may be plural as illustrated, or at least one buffer may be shared in the television ex300. Furthermore, data may be stored in a buffer so that the system overflow and underflow may be avoided between the modulation/demodulation unit ex302 and the multiplexing/demultiplexing unit ex303, for example.

Furthermore, the television ex300 may include a configuration for receiving an AV input from a microphone or a camera other than the configuration for obtaining audio and video data from a broadcast or a recording medium, and may code the obtained data. Although the television ex300 can code, multiplex, and provide outside data in the description, it may be capable of only receiving, decoding, and providing outside data but not the coding, multiplexing, and providing outside data.

Furthermore, when the reader/recorder ex218 reads or writes multiplexed data from or on a recording medium, one of the television ex300 and the reader/recorder ex218 may decode or code the multiplexed data, and the television ex300 and the reader/recorder ex218 may share the decoding or coding.

Figure 41:
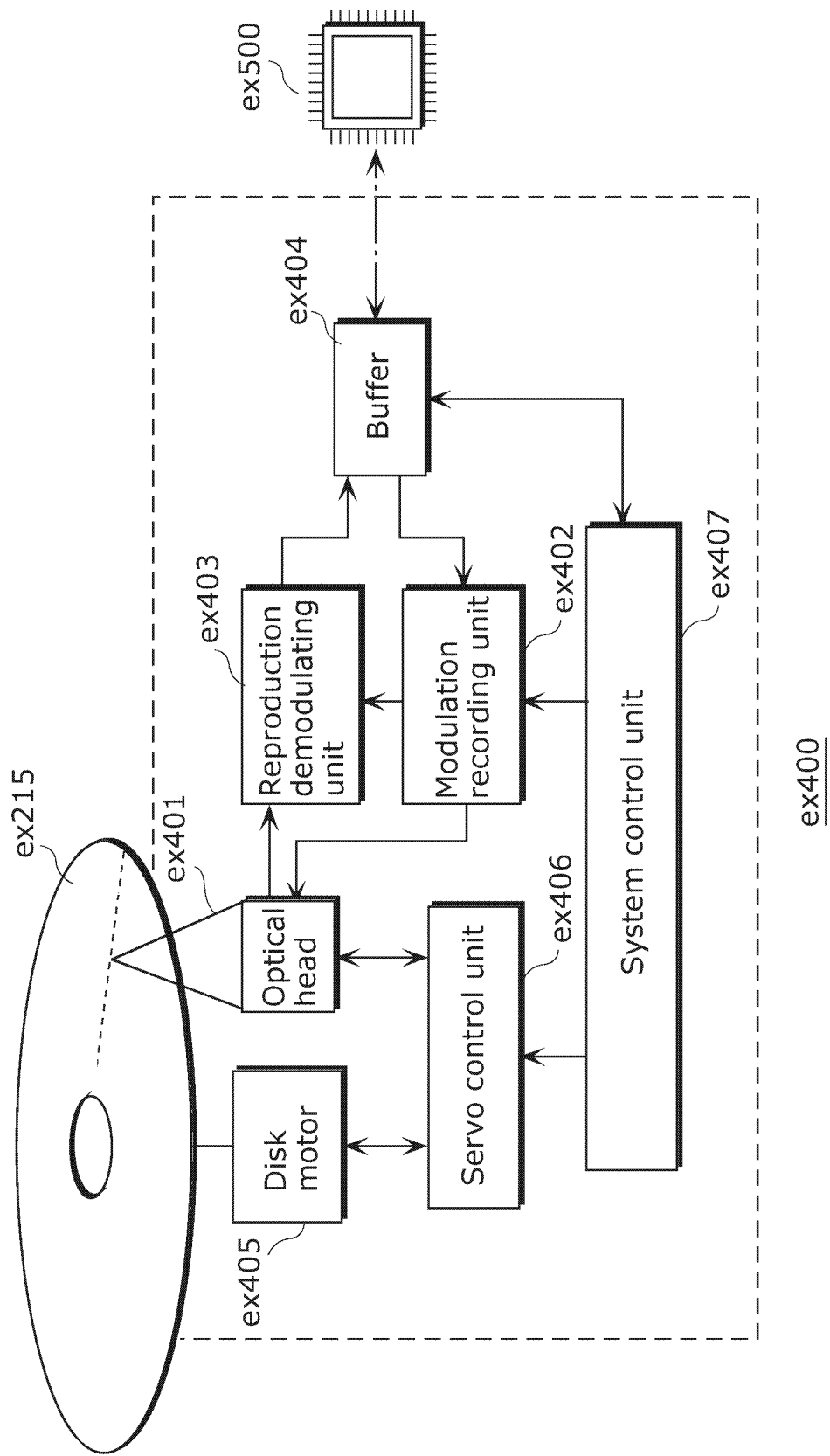
FIG. 41 shows a block diagram illustrating an example of a configuration of an information reproducing/recording unit that reads and writes information from and on a recording medium that is an optical disk.

As an example, FIG. 41 illustrates a configuration of an information reproducing/recording unit ex400 when data is read or written from or on an optical disk. The information reproducing/recording unit ex400 includes constituent elements ex401, ex402, ex403, ex404, ex405, ex406, and ex407 to be described hereinafter. The optical head ex401 irradiates a laser spot in a recording surface of the recording medium ex215 that is an optical disk to write information, and detects reflected light from the recording surface of the recording medium ex215 to read the information. The modulation recording unit ex402 electrically drives a semiconductor laser included in the optical head ex401, and modulates the laser light according to recorded data. The reproduction demodulating unit ex403 amplifies a reproduction signal obtained by electrically detecting the reflected light from the recording surface using a photo detector included in the optical head ex401, and demodulates the reproduction signal by separating a signal component recorded on the recording medium ex215 to reproduce the necessary information. The buffer ex404 temporarily holds the information to be recorded on the recording medium ex215 and the information reproduced from the recording medium ex215. The disk motor ex405 rotates the recording medium ex215. The servo control unit ex406 moves the optical head ex401 to a predetermined information track while controlling the rotation drive of the disk motor ex405 so as to follow the laser spot. The system control unit ex407 controls overall the information reproducing/recording unit ex400. The reading and writing processes can be implemented by the system control unit ex407 using various information stored in the buffer ex404 and generating and adding new information as necessary, and by the modulation recording unit ex402, the reproduction demodulating unit ex403, and the servo control unit ex406 that record and reproduce information through the optical head ex401 while being operated in a coordinated manner. The system control unit ex407 includes, for example, a microprocessor, and executes processing by causing a computer to execute a program for read and write.

Although the optical head ex401 irradiates a laser spot in the description, it may perform high-density recording using near field light.

Figure 42:
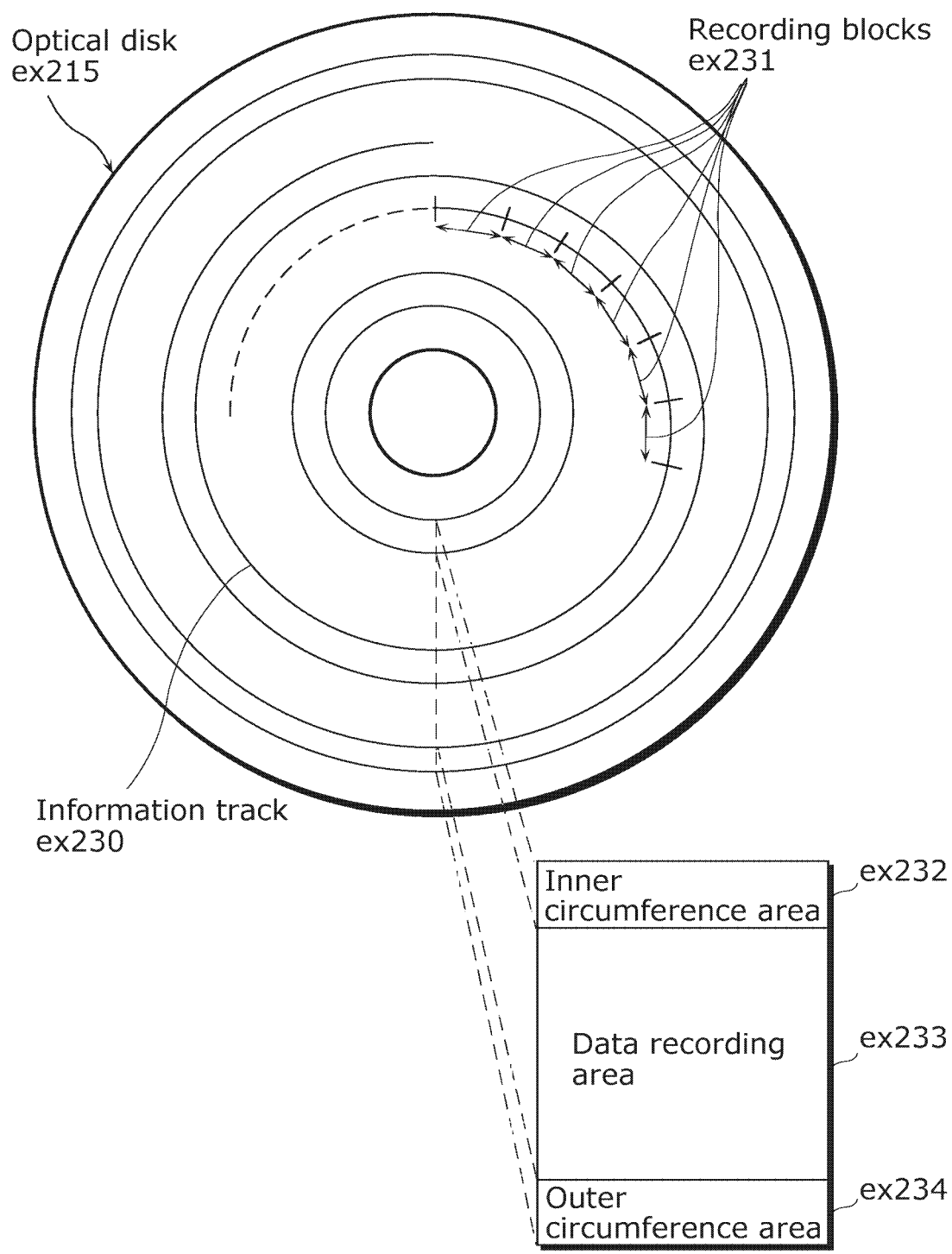
FIG. 42 shows an example of a configuration of a recording medium that is an optical disk.

FIG. 42 illustrates the recording medium ex215 that is the optical disk. On the recording surface of the recording medium ex215, guide grooves are spirally formed, and an information track ex230 records, in advance, address information indicating an absolute position on the disk according to change in a shape of the guide grooves. The address information includes information for determining positions of recording blocks ex231 that are a unit for recording data. Reproducing the information track ex230 and reading the address information in an apparatus that records and reproduces data can lead to determination of the positions of the recording blocks. Furthermore, the recording medium ex215 includes a data recording area ex233, an inner circumference area ex232, and an outer circumference area ex234. The data recording area ex233 is an area for use in recording the user data. The inner circumference area ex232 and the outer circumference area ex234 that are inside and outside of the data recording area ex233, respectively are for specific use except for recording the user data. The information reproducing/recording unit 400 reads and writes coded audio, coded video data, or multiplexed data obtained by multiplexing the coded audio and video data, from and on the data recording area ex233 of the recording medium ex215.

Although an optical disk having a layer, such as a DVD and a BD is described as an example in the description, the optical disk is not limited to such, and may be an optical disk having a multilayer structure and capable of being recorded on a part other than the surface. Furthermore, the optical disk may have a structure for multidimensional recording/reproduction, such as recording of information using light of colors with different wavelengths in the same portion of the optical disk and for recording information having different layers from various angles.

Furthermore, a car ex210 having an antenna ex205 can receive data from the satellite ex202 and others, and reproduce video on a display device such as a car navigation system ex211 set in the car ex210, in the digital broadcasting system ex200. Here, a configuration of the car navigation system ex211 will be a configuration, for example, including a GPS receiving unit from the configuration illustrated in FIG. 40. The same will be true for the configuration of the computer ex111, the cellular phone ex114, and others.

Figure 43A:
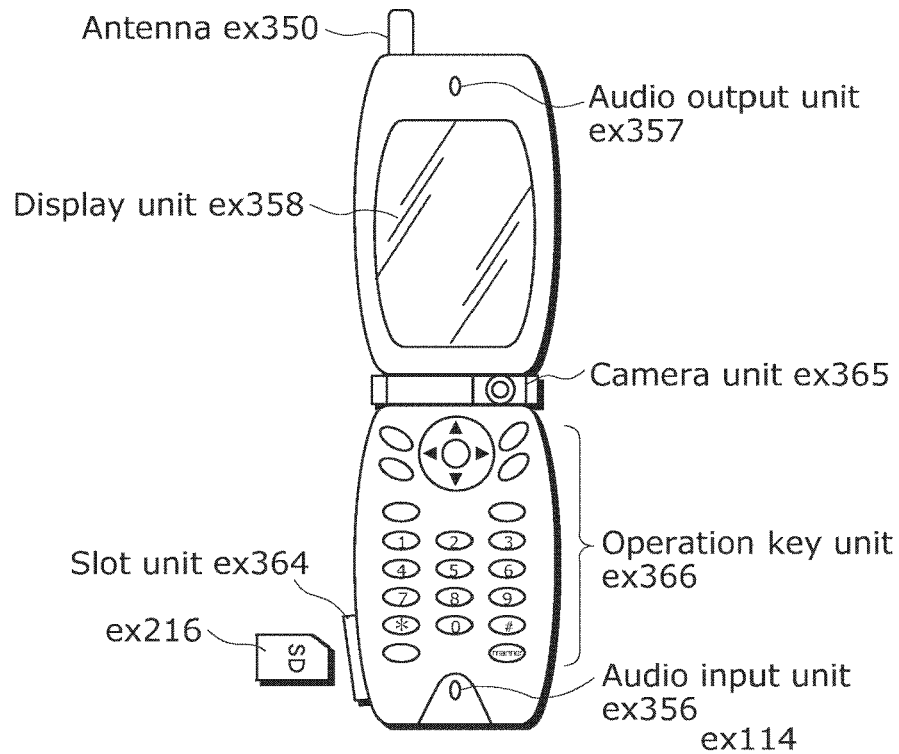
FIG. 43A shows an example of a cellular phone.

FIG. 43A illustrates the cellular phone ex114 that uses the moving picture coding method and the moving picture decoding method described in embodiments. The cellular phone ex114 includes: an antenna ex350 for transmitting and receiving radio waves through the base station ex110; a camera unit ex365 capable of capturing moving and still images; and a display unit ex358 such as a liquid crystal display for displaying the data such as decoded video captured by the camera unit ex365 or received by the antenna ex350. The cellular phone ex114 further includes: a main body unit including an operation key unit ex366; an audio output unit ex357 such as a speaker for output of audio; an audio input unit ex356 such as a microphone for input of audio; a memory unit ex367 for storing captured video or still pictures, recorded audio, coded or decoded data of the received video, the still pictures, e-mails, or others; and a slot unit ex364 that is an interface unit for a recording medium that stores data in the same manner as the memory unit ex367.

Figure 43B:
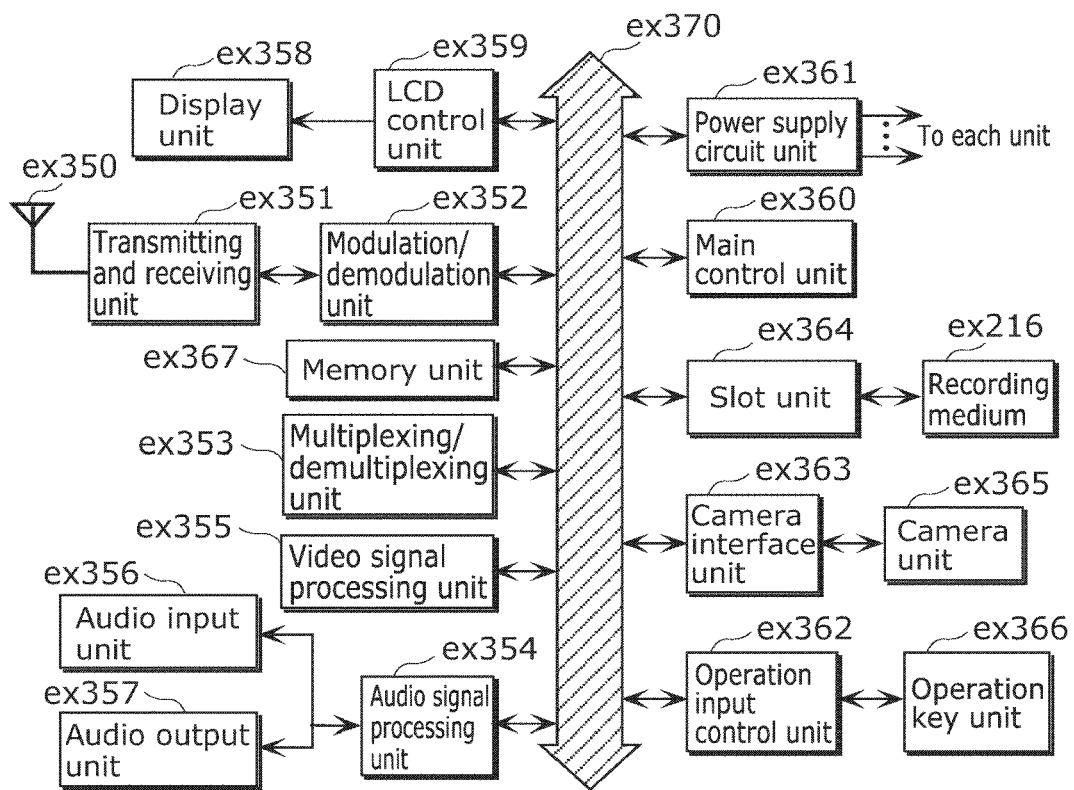
FIG. 43B is a block diagram showing an example of a configuration of a cellular phone.

Next, an example of a configuration of the cellular phone ex114 will be described with reference to FIG. 43B. In the cellular phone ex114, a main control unit ex360 designed to control overall each unit of the main body including the display unit ex358 as well as the operation key unit ex366 is connected mutually, via a synchronous bus ex370, to a power supply circuit unit ex361, an operation input control unit ex362, a video signal processing unit ex355, a camera interface unit ex363, a liquid crystal display (LCD) control unit ex359, a modulation/demodulation unit ex352, a multiplexing/demultiplexing unit ex353, an audio signal processing unit ex354, the slot unit ex364, and the memory unit ex367.

When a call-end key or a power key is turned ON by a user's operation, the power supply circuit unit ex361 supplies the respective units with power from a battery pack so as to activate the cell phone ex114.

In the cellular phone ex114, the audio signal processing unit ex354 converts the audio signals collected by the audio input unit ex356 in voice conversation mode into digital audio signals under the control of the main control unit ex360 including a CPU, ROM, and RAM. Then, the modulation/demodulation unit ex352 performs spread spectrum processing on the digital audio signals, and the transmitting and receiving unit ex351 performs digital-to-analog conversion and frequency conversion on the data, so as to transmit the resulting data via the antenna ex350. Also, in the cellular phone ex114, the transmitting and receiving unit ex351 amplifies the data received by the antenna ex350 in voice conversation mode and performs frequency conversion and the analog-to-digital conversion on the data. Then, the modulation/demodulation unit ex352 performs inverse spread spectrum processing on the data, and the audio signal processing unit ex354 converts it into analog audio signals, so as to output them via the audio output unit ex357.

Furthermore, when an e-mail in data communication mode is transmitted, text data of the e-mail inputted by operating the operation key unit ex366 and others of the main body is sent out to the main control unit ex360 via the operation input control unit ex362. The main control unit ex360 causes the modulation/demodulation unit ex352 to perform spread spectrum processing on the text data, and the transmitting and receiving unit ex351 performs the digital-to-analog conversion and the frequency conversion on the resulting data to transmit the data to the base station ex110 via the antenna ex350. When an e-mail is received, processing that is approximately inverse to the processing for transmitting an e-mail is performed on the received data, and the resulting data is provided to the display unit ex358.

When video, still images, or video and audio in data communication mode is or are transmitted, the video signal processing unit ex355 compresses and codes video signals supplied from the camera unit ex365 using the moving picture coding method shown in each of embodiments (i.e., functions as the image coding apparatus according to the aspect of the present disclosure), and transmits the coded video data to the multiplexing/demultiplexing unit ex353. In contrast, during when the camera unit ex365 captures video, still images, and others, the audio signal processing unit ex354 codes audio signals collected by the audio input unit ex356, and transmits the coded audio data to the multiplexing/demultiplexing unit ex353.

The multiplexing/demultiplexing unit ex353 multiplexes the coded video data supplied from the video signal processing unit ex355 and the coded audio data supplied from the audio signal processing unit ex354, using a predetermined method. Then, the modulation/demodulation unit (modulation/demodulation circuit unit) ex352 performs spread spectrum processing on the multiplexed data, and the transmitting and receiving unit ex351 performs digital-to-analog conversion and frequency conversion on the data so as to transmit the resulting data via the antenna ex350.

When receiving data of a video file which is linked to a Web page and others in data communication mode or when receiving an e-mail with video and/or audio attached, in order to decode the multiplexed data received via the antenna ex350, the multiplexing/demultiplexing unit ex353 demultiplexes the multiplexed data into a video data bit stream and an audio data bit stream, and supplies the video signal processing unit ex355 with the coded video data and the audio signal processing unit ex354 with the coded audio data, through the synchronous bus ex370. The video signal processing unit ex355 decodes the video signal using a moving picture decoding method corresponding to the moving picture coding method shown in each of embodiments (i.e., functions as the image decoding apparatus according to the aspect of the present disclosure), and then the display unit ex358 displays, for instance, the video and still images included in the video file linked to the Web page via the LCD control unit ex359. Furthermore, the audio signal processing unit ex354 decodes the audio signal, and the audio output unit ex357 provides the audio.

Furthermore, similarly to the television ex300, a terminal such as the cellular phone ex114 probably have 3 types of implementation configurations including not only (i) a transmitting and receiving terminal including both a coding apparatus and a decoding apparatus, but also (ii) a transmitting terminal including only a coding apparatus and (iii) a receiving terminal including only a decoding apparatus. Although the digital broadcasting system ex200 receives and transmits the multiplexed data obtained by multiplexing audio data onto video data in the description, the multiplexed data may be data obtained by multiplexing not audio data but character data related to video onto video data, and may be not multiplexed data but video data itself.

As such, the moving picture coding method and the moving picture decoding method in each of embodiments can be used in any of the devices and systems described. Thus, the advantages described in each of embodiments can be obtained.

Furthermore, various modifications and revisions can be made in any of the embodiments in the present disclosure.

Embodiment 5

Video data can be generated by switching, as necessary, between (i) the moving picture coding method or the moving picture coding apparatus shown in each of embodiments and (ii) a moving picture coding method or a moving picture coding apparatus in conformity with a different standard, such as MPEG-2, MPEG-4 AVC, and VC-1.

Here, when a plurality of video data that conforms to the different standards is generated and is then decoded, the decoding methods need to be selected to conform to the different standards. However, since to which standard each of the plurality of the video data to be decoded conform cannot be detected, an appropriate decoding method cannot be selected.

In view of this, multiplexed data obtained by multiplexing audio data and others onto video data has a structure including identification information indicating to which standard the video data conforms. The specific structure of the multiplexed data including the video data generated in the moving picture coding method and by the moving picture coding apparatus shown in each of embodiments will be hereinafter described. The multiplexed data is a digital stream in the MPEG-2 Transport Stream format.

FIG. 44 illustrates a structure of the multiplexed data. As illustrated in FIG. 44, the multiplexed data can be obtained by multiplexing at least one of a video stream, an audio stream, a presentation graphics stream (PG), and an interactive graphics stream. The video stream represents primary video and secondary video of a movie, the audio stream (IG) represents a primary audio part and a secondary audio part to be mixed with the primary audio part, and the presentation graphics stream represents subtitles of the movie. Here, the primary video is normal video to be displayed on a screen, and the secondary video is video to be displayed on a smaller window in the primary video. Furthermore, the interactive graphics stream represents an interactive screen to be generated by arranging the GUI components on a screen. The video stream is coded in the moving picture coding method or by the moving picture coding apparatus shown in each of embodiments, or in a moving picture coding method or by a moving picture coding apparatus in conformity with a conventional standard, such as MPEG-2, MPEG-4 AVC, and VC-1. The audio stream is coded in accordance with a standard, such as Dolby-AC-3, Dolby Digital Plus, MLP, DTS, DTS-HD, and linear PCM.

Each stream included in the multiplexed data is identified by PID. For example, 0x1011 is allocated to the video stream to be used for video of a movie, 0x1100 to 0x111F are allocated to the audio streams, 0x1200 to 0x121F are allocated to the presentation graphics streams, 0x1400 to 0x141F are allocated to the interactive graphics streams, 0x1B00 to 0x1B1F are allocated to the video streams to be used for secondary video of the movie, and 0x1A00 to 0x1A1F are allocated to the audio streams to be used for the secondary audio to be mixed with the primary audio.

Figure 45:
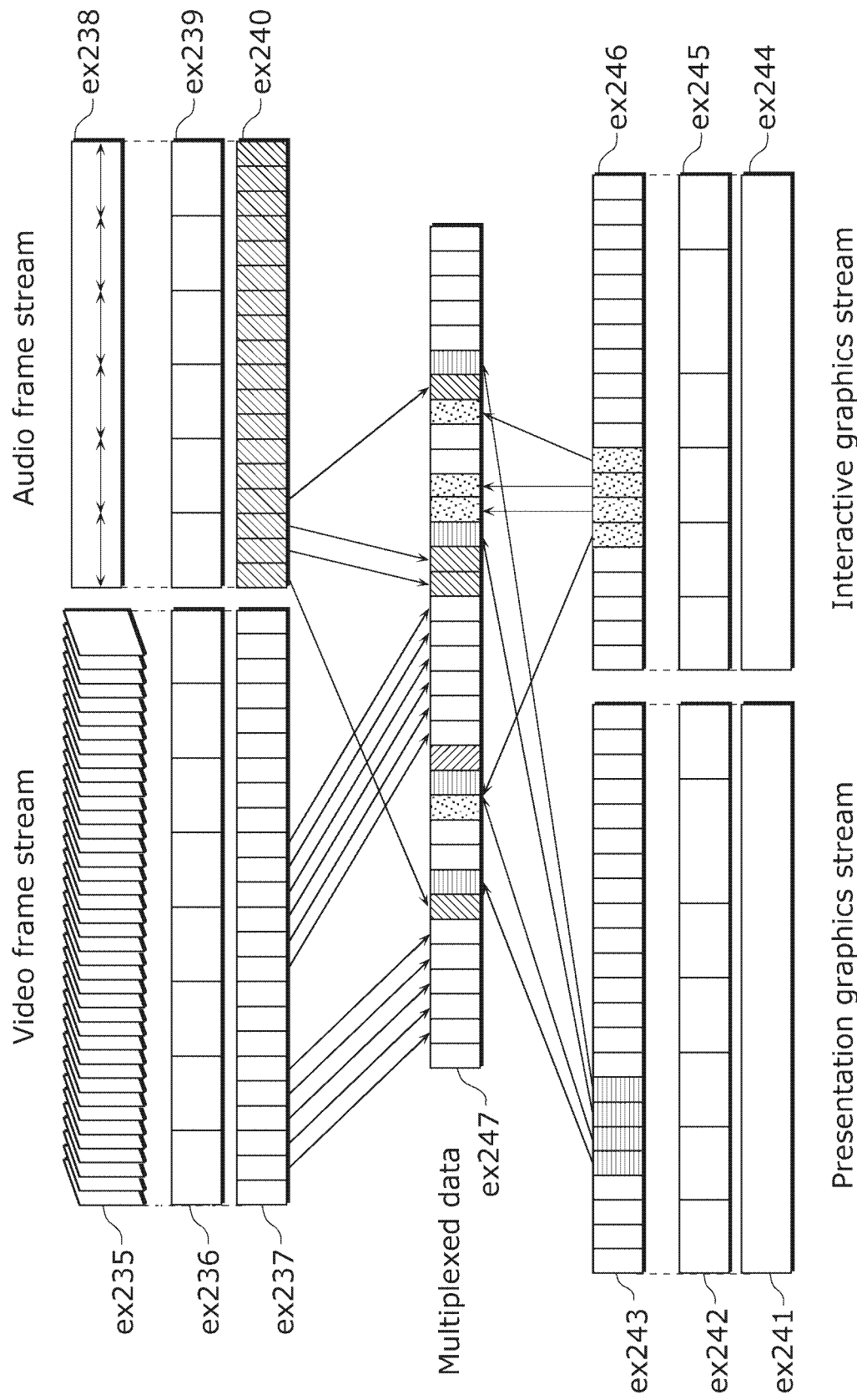
FIG. 45 schematically shows how each stream is multiplexed in multiplexed data.

FIG. 45 schematically illustrates how data is multiplexed. First, a video stream ex235 composed of video frames and an audio stream ex238 composed of audio frames are transformed into a stream of PES packets ex236 and a stream of PES packets ex239, and further into TS packets ex237 and TS packets ex240, respectively. Similarly, data of a presentation graphics stream ex241 and data of an interactive graphics stream ex244 are transformed into a stream of PES packets ex242 and a stream of PES packets ex245, and further into TS packets ex243 and TS packets ex246, respectively. These TS packets are multiplexed into a stream to obtain multiplexed data ex247.

Figure 46:
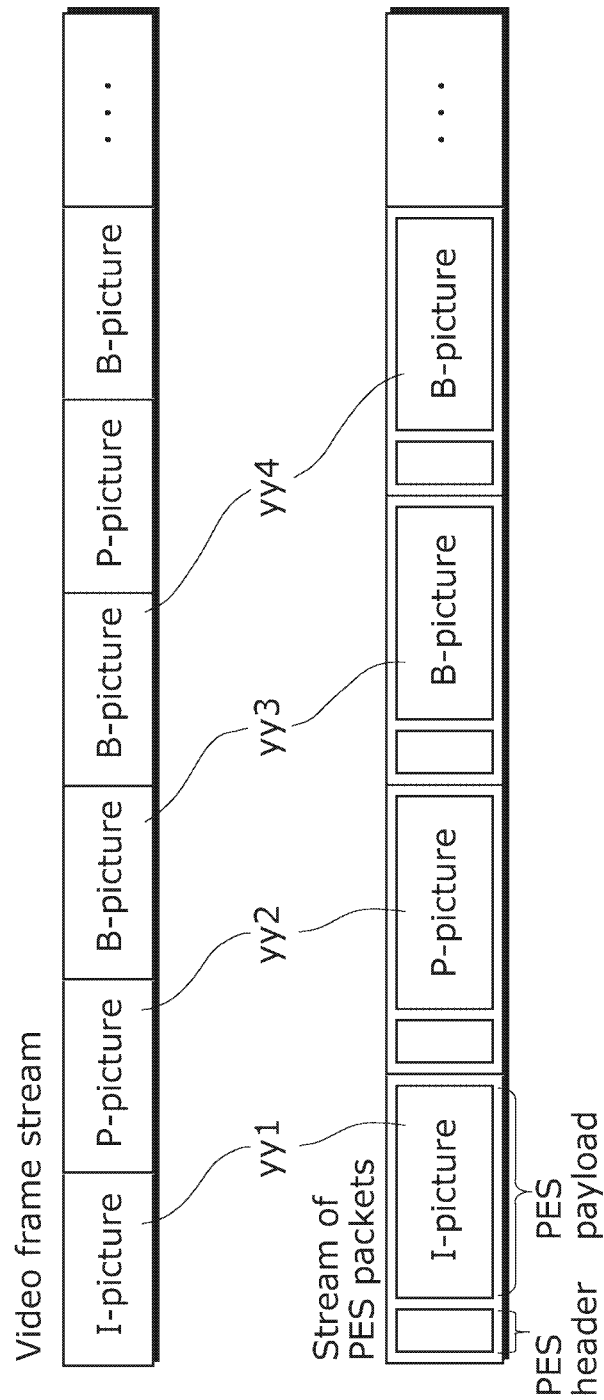
FIG. 46 shows how a video stream is stored in a stream of PES packets in more detail.

FIG. 46 illustrates how a video stream is stored in a stream of PES packets in more detail. The first bar in FIG. 46 shows a video frame stream in a video stream. The second bar shows the stream of PES packets. As indicated by arrows denoted as yy1, yy2, yy3, and yy4 in FIG. 46, the video stream is divided into pictures as I pictures, B pictures, and P pictures each of which is a video presentation unit, and the pictures are stored in a payload of each of the PES packets. Each of the PES packets has a PES header, and the PES header stores a Presentation Time-Stamp (PTS) indicating a display time of the picture, and a Decoding Time-Stamp (DTS) indicating a decoding time of the picture.

Figure 47:
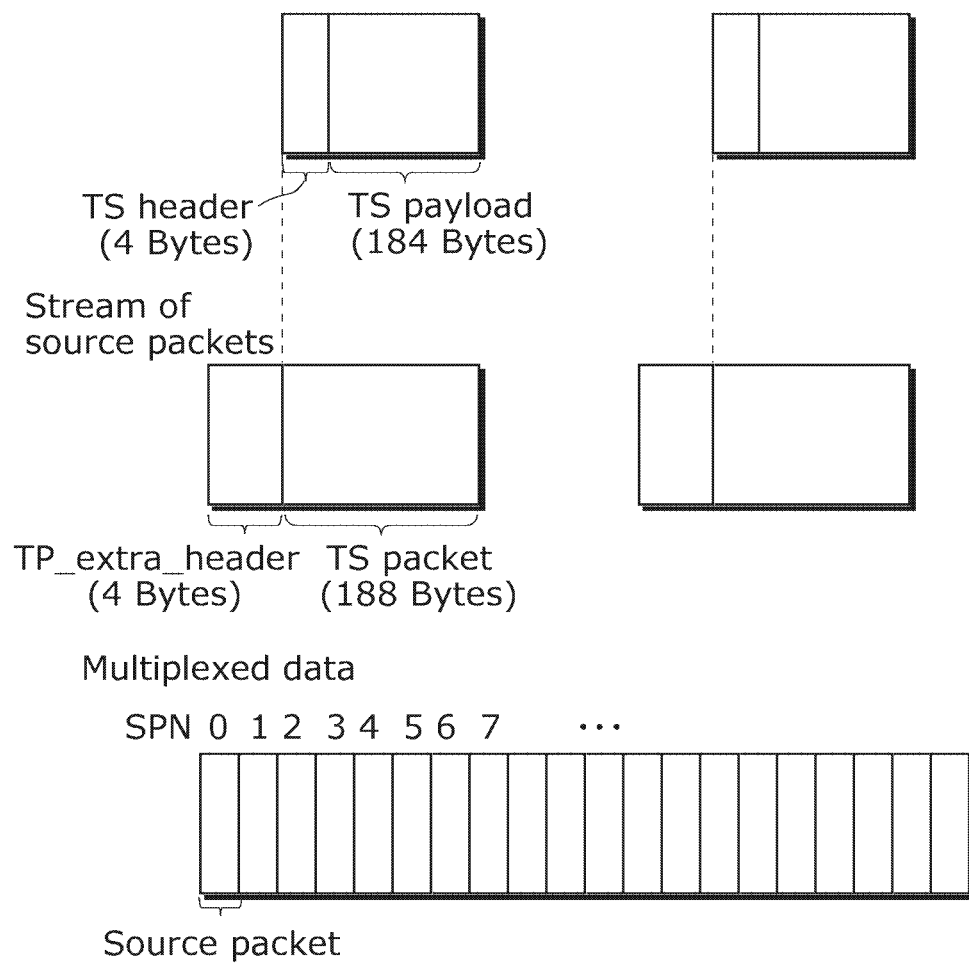
FIG. 47 shows a structure of TS packets and source packets in the multiplexed data.

FIG. 47 illustrates a format of TS packets to be finally written on the multiplexed data. Each of the TS packets is a 188-byte fixed length packet including a 4-byte TS header having information, such as a PID for identifying a stream and a 184-byte TS payload for storing data. The PES packets are divided, and stored in the TS payloads, respectively. When a BD ROM is used, each of the TS packets is given a 4-byte TP_Extra_Header, thus resulting in 192-byte source packets. The source packets are written on the multiplexed data. The TP_Extra_Header stores information such as an Arrival_Time_Stamp (ATS). The ATS shows a transfer start time at which each of the TS packets is to be transferred to a PID filter. The source packets are arranged in the multiplexed data as shown at the bottom of FIG. 47. The numbers incrementing from the head of the multiplexed data are called source packet numbers (SPNs).

Each of the TS packets included in the multiplexed data includes not only streams of audio, video, subtitles and others, but also a Program Association Table (PAT), a Program Map Table (PMT), and a Program Clock Reference (PCR). The PAT shows what a PID in a PMT used in the multiplexed data indicates, and a PID of the PAT itself is registered as zero. The PMT stores PIDs of the streams of video, audio, subtitles and others included in the multiplexed data, and attribute information of the streams corresponding to the PIDs. The PMT also has various descriptors relating to the multiplexed data. The descriptors have information such as copy control information showing whether copying of the multiplexed data is permitted or not. The PCR stores STC time information corresponding to an ATS showing when the PCR packet is transferred to a decoder, in order to achieve synchronization between an Arrival Time Clock (ATC) that is a time axis of ATSs, and an System Time Clock (STC) that is a time axis of PTSs and DTSs.

Figure 48:
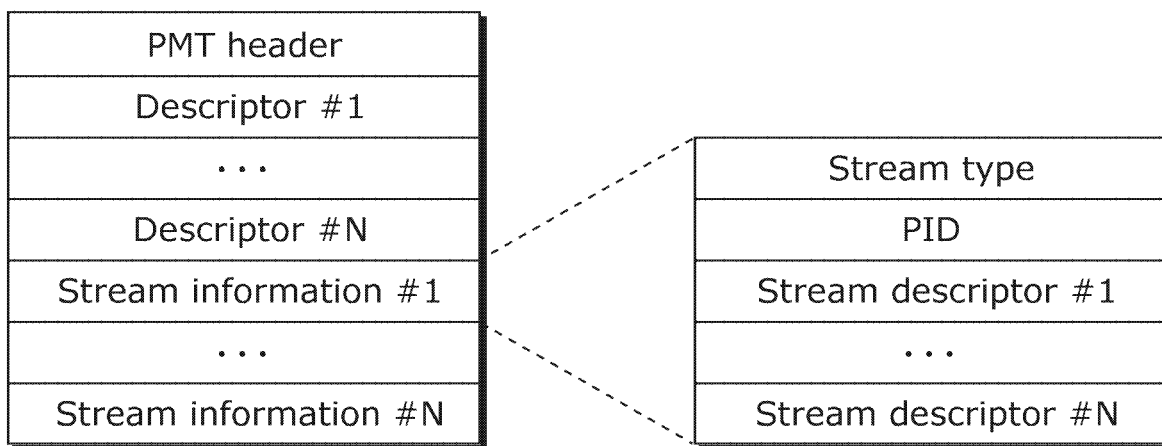
FIG. 48 shows a data structure of a PMT.

FIG. 48 illustrates the data structure of the PMT in detail. A PMT header is disposed at the top of the PMT. The PMT header describes the length of data included in the PMT and others. A plurality of descriptors relating to the multiplexed data is disposed after the PMT header. Information such as the copy control information is described in the descriptors. After the descriptors, a plurality of pieces of stream information relating to the streams included in the multiplexed data is disposed. Each piece of stream information includes stream descriptors each describing information, such as a stream type for identifying a compression codec of a stream, a stream PID, and stream attribute information (such as a frame rate or an aspect ratio). The stream descriptors are equal in number to the number of streams in the multiplexed data.

When the multiplexed data is recorded on a recording medium and others, it is recorded together with multiplexed data information files.

Figure 49:
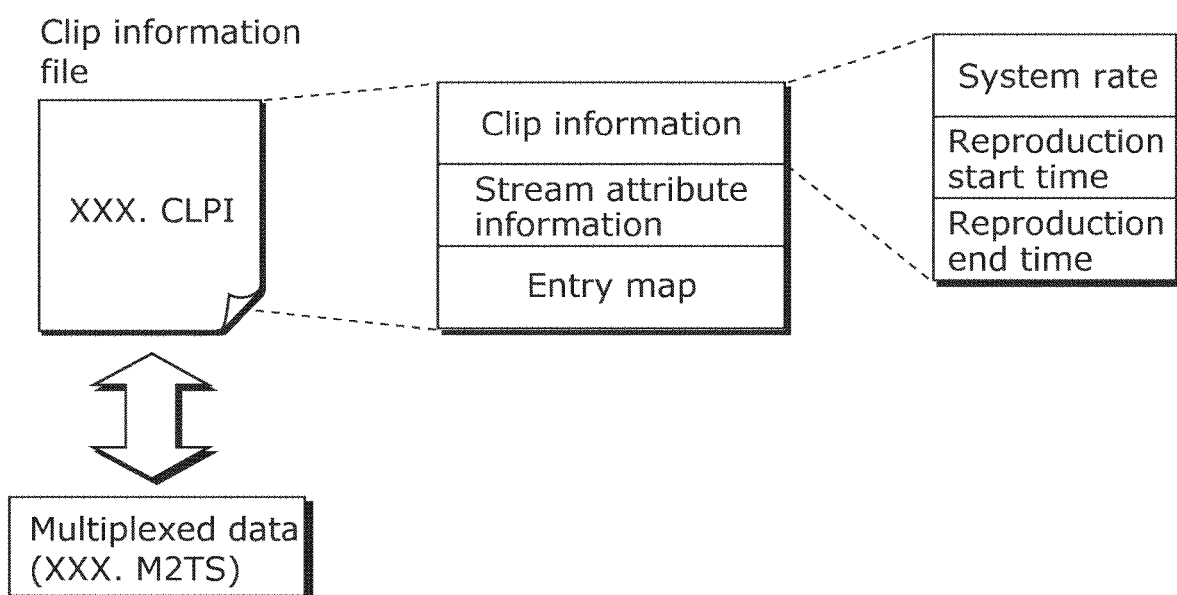
FIG. 49 shows an internal structure of multiplexed data information.

Each of the multiplexed data information files is management information of the multiplexed data as shown in FIG. 49. The multiplexed data information files are in one to one correspondence with the multiplexed data, and each of the files includes multiplexed data information, stream attribute information, and an entry map.

As illustrated in FIG. 49, the multiplexed data information includes a system rate, a reproduction start time, and a reproduction end time. The system rate indicates the maximum transfer rate at which a system target decoder to be described later transfers the multiplexed data to a PID filter. The intervals of the ATSs included in the multiplexed data are set to not higher than a system rate. The reproduction start time indicates a PTS in a video frame at the head of the multiplexed data. An interval of one frame is added to a PTS in a video frame at the end of the multiplexed data, and the PTS is set to the reproduction end time.

Figure 50:
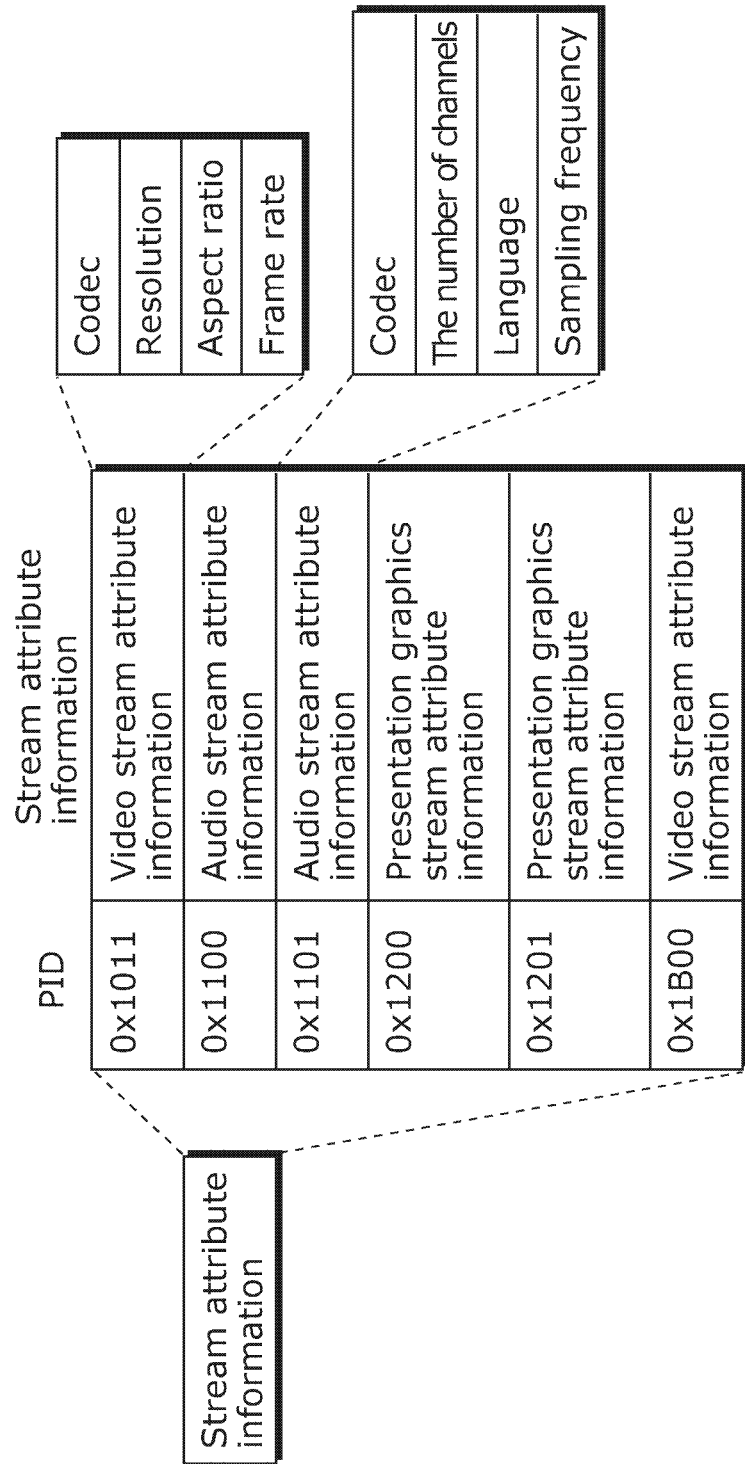
FIG. 50 shows an internal structure of stream attribute information.

As shown in FIG. 50, a piece of attribute information is registered in the stream attribute information, for each PID of each stream included in the multiplexed data. Each piece of attribute information has different information depending on whether the corresponding stream is a video stream, an audio stream, a presentation graphics stream, or an interactive graphics stream. Each piece of video stream attribute information carries information including what kind of compression codec is used for compressing the video stream, and the resolution, aspect ratio and frame rate of the pieces of picture data that is included in the video stream. Each piece of audio stream attribute information carries information including what kind of compression codec is used for compressing the audio stream, how many channels are included in the audio stream, which language the audio stream supports, and how high the sampling frequency is. The video stream attribute information and the audio stream attribute information are used for initialization of a decoder before the player plays back the information.

In the present embodiment, the multiplexed data to be used is of a stream type included in the PMT. Furthermore, when the multiplexed data is recorded on a recording medium, the video stream attribute information included in the multiplexed data information is used. More specifically, the moving picture coding method or the moving picture coding apparatus described in each of embodiments includes a step or a unit for allocating unique information indicating video data generated by the moving picture coding method or the moving picture coding apparatus in each of embodiments, to the stream type included in the PMT or the video stream attribute information. With the configuration, the video data generated by the moving picture coding method or the moving picture coding apparatus described in each of embodiments can be distinguished from video data that conforms to another standard.

Figure 51:
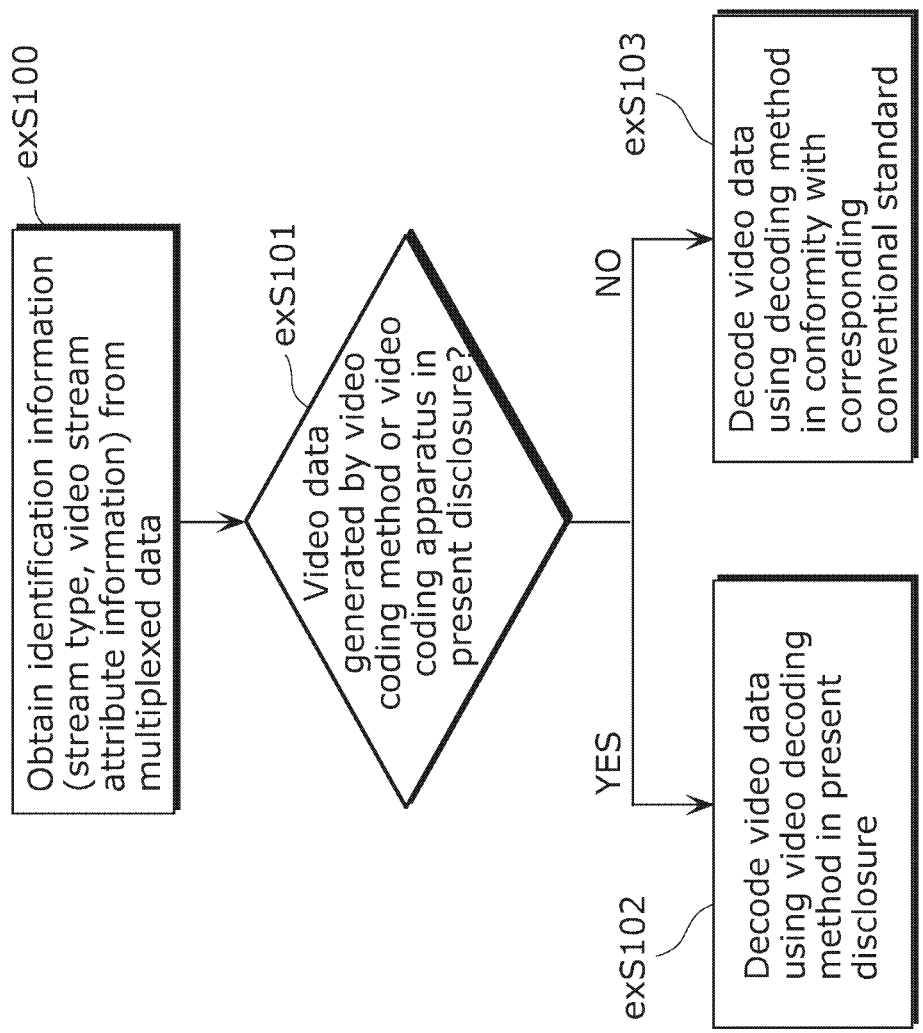
FIG. 51 shows steps for identifying video data.

Furthermore, FIG. 51 illustrates steps of the moving picture decoding method according to the present embodiment. In Step exS100, the stream type included in the PMT or the video stream attribute information included in the multiplexed data information is obtained from the multiplexed data. Next, in Step exS101, it is determined whether or not the stream type or the video stream attribute information indicates that the multiplexed data is generated by the moving picture coding method or the moving picture coding apparatus in each of embodiments. When it is determined that the stream type or the video stream attribute information indicates that the multiplexed data is generated by the moving picture coding method or the moving picture coding apparatus in each of embodiments, in Step exS102, decoding is performed by the moving picture decoding method in each of embodiments. Furthermore, when the stream type or the video stream attribute information indicates conformance to the conventional standards, such as MPEG-2, MPEG-4 AVC, and VC-1, in Step exS103, decoding is performed by a moving picture decoding method in conformity with the conventional standards.

As such, allocating a new unique value to the stream type or the video stream attribute information enables determination whether or not the moving picture decoding method or the moving picture decoding apparatus that is described in each of embodiments can perform decoding. Even when multiplexed data that conforms to a different standard is input, an appropriate decoding method or apparatus can be selected. Thus, it becomes possible to decode information without any error. Furthermore, the moving picture coding method or apparatus, or the moving picture decoding method or apparatus in the present embodiment can be used in the devices and systems described above.

Embodiment 6

Figure 52:
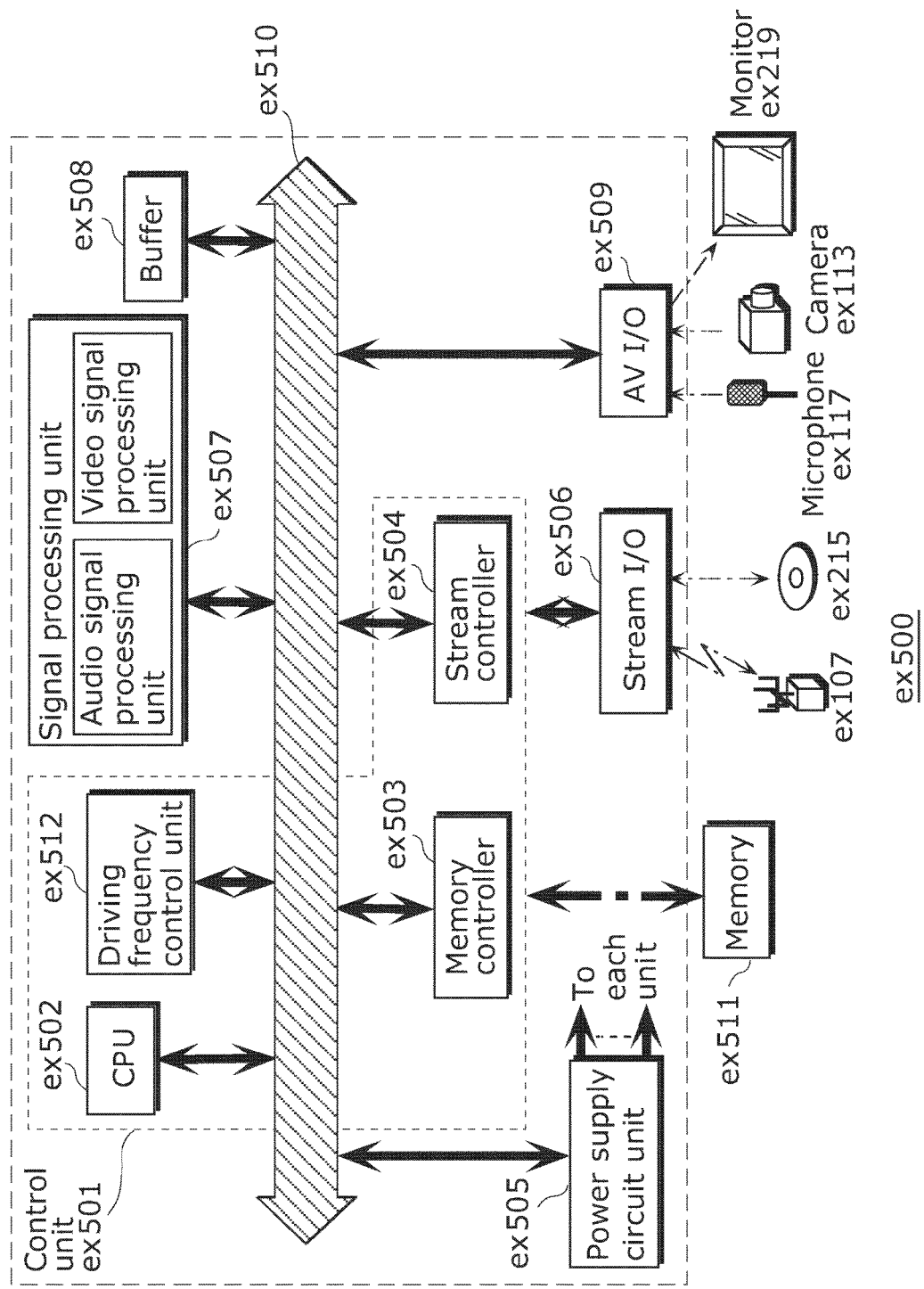
FIG. 52 shows an example of a configuration of an integrated circuit for implementing the moving picture coding method and the moving picture decoding method according to each of embodiments.

Each of the moving picture coding method, the moving picture coding apparatus, the moving picture decoding method, and the moving picture decoding apparatus in each of embodiments is typically achieved in the form of an integrated circuit or a Large Scale Integrated (LSI) circuit. As an example of the LSI, FIG. 52 illustrates a configuration of the LSI ex500 that is made into one chip. The LSI ex500 includes elements ex501, ex502, ex503, ex504, ex505, ex506, ex507, ex508, and ex509 to be described below, and the elements are connected to each other through a bus ex510. The power supply circuit unit ex505 is activated by supplying each of the elements with power when the power supply circuit unit ex505 is turned on.

For example, when coding is performed, the LSI ex500 receives an AV signal from a microphone ex117, a camera ex113, and others through an AV IO ex509 under control of a control unit ex501 including a CPU ex502, a memory controller ex503, a stream controller ex504, and a driving frequency control unit ex512. The received AV signal is temporarily stored in an external memory ex511, such as an SDRAM. Under control of the control unit ex501, the stored data is segmented into data portions according to the processing amount and speed to be transmitted to a signal processing unit ex507. Then, the signal processing unit ex507 codes an audio signal and/or a video signal. Here, the coding of the video signal is the coding described in each of embodiments. Furthermore, the signal processing unit ex507 sometimes multiplexes the coded audio data and the coded video data, and a stream IO ex506 provides the multiplexed data outside. The provided multiplexed data is transmitted to the base station ex107, or written on the recording medium ex215. When data sets are multiplexed, the data should be temporarily stored in the buffer ex508 so that the data sets are synchronized with each other.

Although the memory ex511 is an element outside the LSI ex500, it may be included in the LSI ex500. The buffer ex508 is not limited to one buffer, but may be composed of buffers. Furthermore, the LSI ex500 may be made into one chip or a plurality of chips.

Furthermore, although the control unit ex501 includes the CPU ex502, the memory controller ex503, the stream controller ex504, the driving frequency control unit ex512, the configuration of the control unit ex501 is not limited to such. For example, the signal processing unit ex507 may further include a CPU. Inclusion of another CPU in the signal processing unit ex507 can improve the processing speed. Furthermore, as another example, the CPU ex502 may serve as or be a part of the signal processing unit ex507, and, for example, may include an audio signal processing unit. In such a case, the control unit ex501 includes the signal processing unit ex507 or the CPU ex502 including a part of the signal processing unit ex507.

The name used here is LSI, but it may also be called IC, system LSI, super LSI, or ultra LSI depending on the degree of integration.

Moreover, ways to achieve integration are not limited to the LSI, and a special circuit or a general purpose processor and so forth can also achieve the integration. Field Programmable Gate Array (FPGA) that can be programmed after manufacturing LSIs or a reconfigurable processor that allows re-configuration of the connection or configuration of an LSI can be used for the same purpose. Such a programmable logic device can typically execute the moving picture coding method and/or the moving picture decoding method according to any of the above embodiments, by loading or reading from a memory or the like one or more programs that are included in software or firmware.

In the future, with advancement in semiconductor technology, a brand-new technology may replace LSI. The functional blocks can be integrated using such a technology. The possibility is that the present disclosure is applied to biotechnology.

Embodiment 7

When video data generated in the moving picture coding method or by the moving picture coding apparatus described in each of embodiments is decoded, compared to when video data that conforms to a conventional standard, such as MPEG-2, MPEG-4 AVC, and VC-1 is decoded, the processing amount probably increases. Thus, the LSI ex500 needs to be set to a driving frequency higher than that of the CPU ex502 to be used when video data in conformity with the conventional standard is decoded. However, when the driving frequency is set higher, the power consumption increases.

Figure 53:
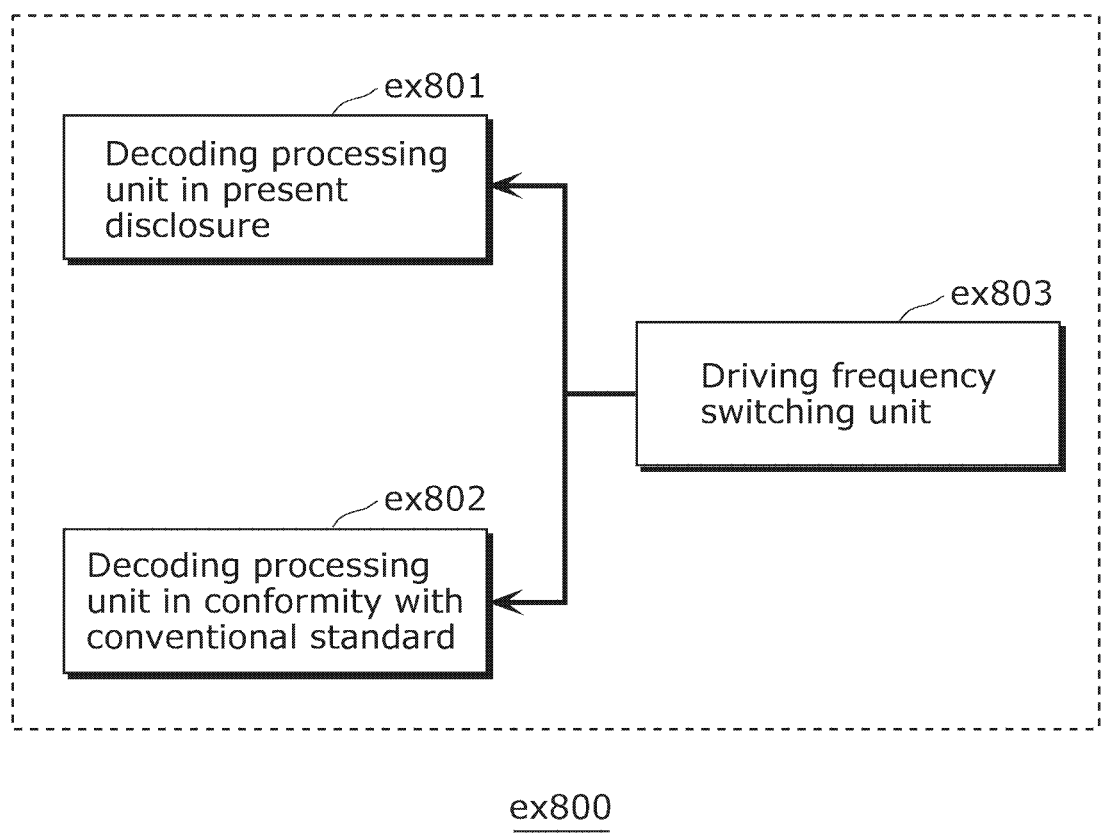
FIG. 53 shows a configuration for switching between driving frequencies.

In view of this, the moving picture decoding apparatus, such as the television ex300 and the LSI ex500 is configured to determine to which standard the video data conforms, and switch between the driving frequencies according to the determined standard. FIG. 53 illustrates a configuration ex800 in the present embodiment. A driving frequency switching unit ex803 sets a driving frequency to a higher driving frequency when video data is generated by the moving picture coding method or the moving picture coding apparatus described in each of embodiments. Then, the driving frequency switching unit ex803 instructs a decoding processing unit ex801 that executes the moving picture decoding method described in each of embodiments to decode the video data. When the video data conforms to the conventional standard, the driving frequency switching unit ex803 sets a driving frequency to a lower driving frequency than that of the video data generated by the moving picture coding method or the moving picture coding apparatus described in each of embodiments. Then, the driving frequency switching unit ex803 instructs the decoding processing unit ex802 that conforms to the conventional standard to decode the video data.

More specifically, the driving frequency switching unit ex803 includes the CPU ex502 and the driving frequency control unit ex512 in FIG. 52. Here, each of the decoding processing unit ex801 that executes the moving picture decoding method described in each of embodiments and the decoding processing unit ex802 that conforms to the conventional standard corresponds to the signal processing unit ex507 in FIG. 52. The CPU ex502 determines to which standard the video data conforms. Then, the driving frequency control unit ex512 determines a driving frequency based on a signal from the CPU ex502. Furthermore, the signal processing unit ex507 decodes the video data based on the signal from the CPU ex502. For example, the identification information described in Embodiment 5 is probably used for identifying the video data. The identification information is not limited to the one described in Embodiment 5 but may be any information as long as the information indicates to which standard the video data conforms. For example, when which standard video data conforms to can be determined based on an external signal for determining that the video data is used for a television or a disk, etc., the determination may be made based on such an external signal. Furthermore, the CPU ex502 selects a driving frequency based on, for example, a look-up table in which the standards of the video data are associated with the driving frequencies as shown in FIG. 55. The driving frequency can be selected by storing the look-up table in the buffer ex508 and in an internal memory of an LSI, and with reference to the look-up table by the CPU ex502.

Figure 54:
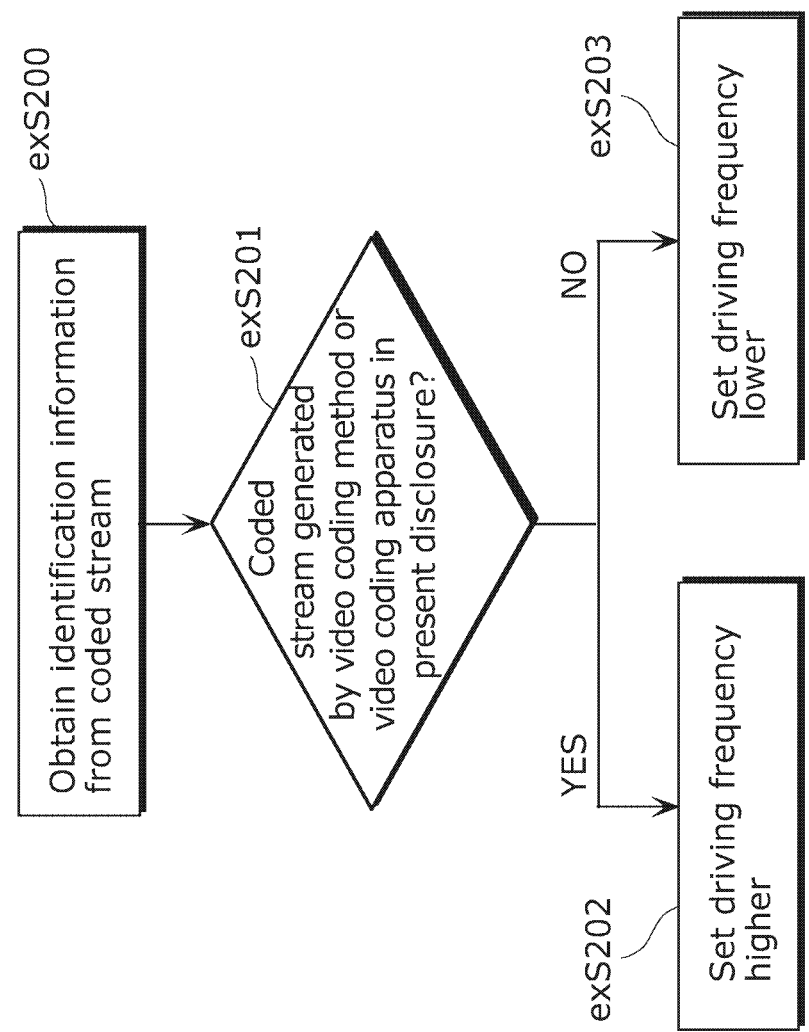
FIG. 54 shows steps for identifying video data and switching between driving frequencies.

FIG. 54 illustrates steps for executing a method in the present embodiment. First, in Step exS200, the signal processing unit ex507 obtains identification information from the multiplexed data. Next, in Step exS201, the CPU ex502 determines whether or not the video data is generated by the coding method and the coding apparatus described in each of embodiments, based on the identification information. When the video data is generated by the moving picture coding method and the moving picture coding apparatus described in each of embodiments, in Step exS202, the CPU ex502 transmits a signal for setting the driving frequency to a higher driving frequency to the driving frequency control unit ex512. Then, the driving frequency control unit ex512 sets the driving frequency to the higher driving frequency. On the other hand, when the identification information indicates that the video data conforms to the conventional standard, such as MPEG-2, MPEG-4 AVC, and VC-1, in Step exS203, the CPU ex502 transmits a signal for setting the driving frequency to a lower driving frequency to the driving frequency control unit ex512. Then, the driving frequency control unit ex512 sets the driving frequency to the lower driving frequency than that in the case where the video data is generated by the moving picture coding method and the moving picture coding apparatus described in each of embodiment.

Furthermore, along with the switching of the driving frequencies, the power conservation effect can be improved by changing the voltage to be applied to the LSI ex500 or an apparatus including the LSI ex500. For example, when the driving frequency is set lower, the voltage to be applied to the LSI ex500 or the apparatus including the LSI ex500 is probably set to a voltage lower than that in the case where the driving frequency is set higher.

Furthermore, when the processing amount for decoding is larger, the driving frequency may be set higher, and when the processing amount for decoding is smaller, the driving frequency may be set lower as the method for setting the driving frequency. Thus, the setting method is not limited to the ones described above. For example, when the processing amount for decoding video data in conformity with MPEG-4 AVC is larger than the processing amount for decoding video data generated by the moving picture coding method and the moving picture coding apparatus described in each of embodiments, the driving frequency is probably set in reverse order to the setting described above.

Furthermore, the method for setting the driving frequency is not limited to the method for setting the driving frequency lower. For example, when the identification information indicates that the video data is generated by the moving picture coding method and the moving picture coding apparatus described in each of embodiments, the voltage to be applied to the LSI ex500 or the apparatus including the LSI ex500 is probably set higher. When the identification information indicates that the video data conforms to the conventional standard, such as MPEG-2, MPEG-4 AVC, and VC-1, the voltage to be applied to the LSI ex500 or the apparatus including the LSI ex500 is probably set lower. As another example, when the identification information indicates that the video data is generated by the moving picture coding method and the moving picture coding apparatus described in each of embodiments, the driving of the CPU ex502 does not probably have to be suspended. When the identification information indicates that the video data conforms to the conventional standard, such as MPEG-2, MPEG-4 AVC, and VC-1, the driving of the CPU ex502 is probably suspended at a given time because the CPU ex502 has extra processing capacity. Even when the identification information indicates that the video data is generated by the moving picture coding method and the moving picture coding apparatus described in each of embodiments, in the case where the CPU ex502 has extra processing capacity, the driving of the CPU ex502 is probably suspended at a given time. In such a case, the suspending time is probably set shorter than that in the case where when the identification information indicates that the video data conforms to the conventional standard, such as MPEG-2, MPEG-4 AVC, and VC-1.

Accordingly, the power conservation effect can be improved by switching between the driving frequencies in accordance with the standard to which the video data conforms. Furthermore, when the LSI ex500 or the apparatus including the LSI ex500 is driven using a battery, the battery life can be extended with the power conservation effect.

Embodiment 8

There are cases where a plurality of video data that conforms to different standards, is provided to the devices and systems, such as a television and a cellular phone. In order to enable decoding the plurality of video data that conforms to the different standards, the signal processing unit ex507 of the LSI ex500 needs to conform to the different standards. However, increase in the scale of the circuit of the LSI ex500 and increase in the cost arise with the individual use of the signal processing units ex507 that conform to the respective standards.

Figure 56A:
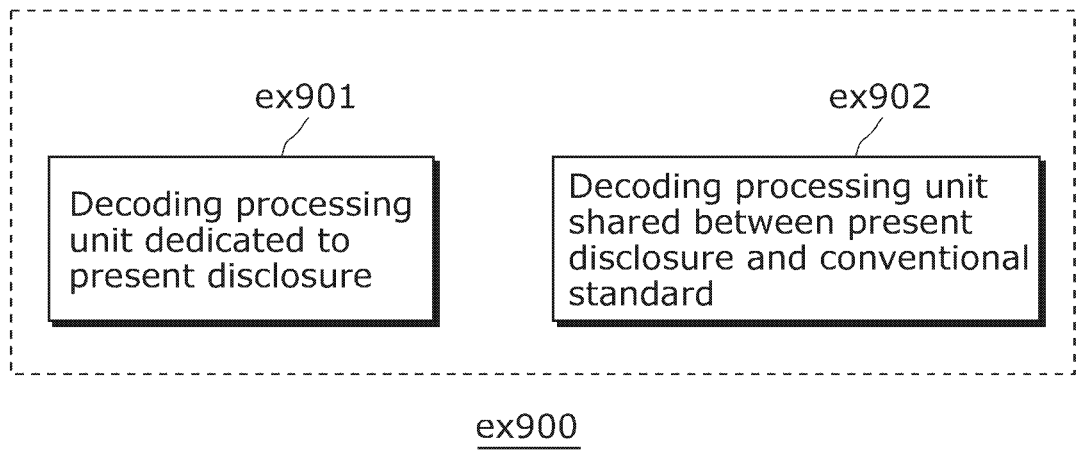
FIG. 56A is a diagram showing an example of a configuration for sharing a module of a signal processing unit.

In view of this, what is conceived is a configuration in which the decoding processing unit for implementing the moving picture decoding method described in each of embodiments and the decoding processing unit that conforms to the conventional standard, such as MPEG-2, MPEG-4 AVC, and VC-1 are partly shared. Ex900 in FIG. 56A shows an example of the configuration. For example, the moving picture decoding method described in each of embodiments and the moving picture decoding method that conforms to MPEG-4 AVC have, partly in common, the details of processing, such as entropy coding, inverse quantization, deblocking filtering, and motion compensated prediction. The details of processing to be shared probably include use of a decoding processing unit ex902 that conforms to MPEG-4 AVC. In contrast, a dedicated decoding processing unit ex901 is probably used for other processing which is unique to an aspect of the present disclosure and does not conform to MPEG-4 AVC. Since the aspect of the present disclosure is characterized by entropy decoding in particular, for example, the dedicated decoding processing unit ex901 is used for entropy decoding. Otherwise, the decoding processing unit is probably shared for one of the inverse quantization, deblocking filtering, and motion compensation, or all of the processing. The decoding processing unit for implementing the moving picture decoding method described in each of embodiments may be shared for the processing to be shared, and a dedicated decoding processing unit may be used for processing unique to that of MPEG-4 AVC.

Figure 56B:
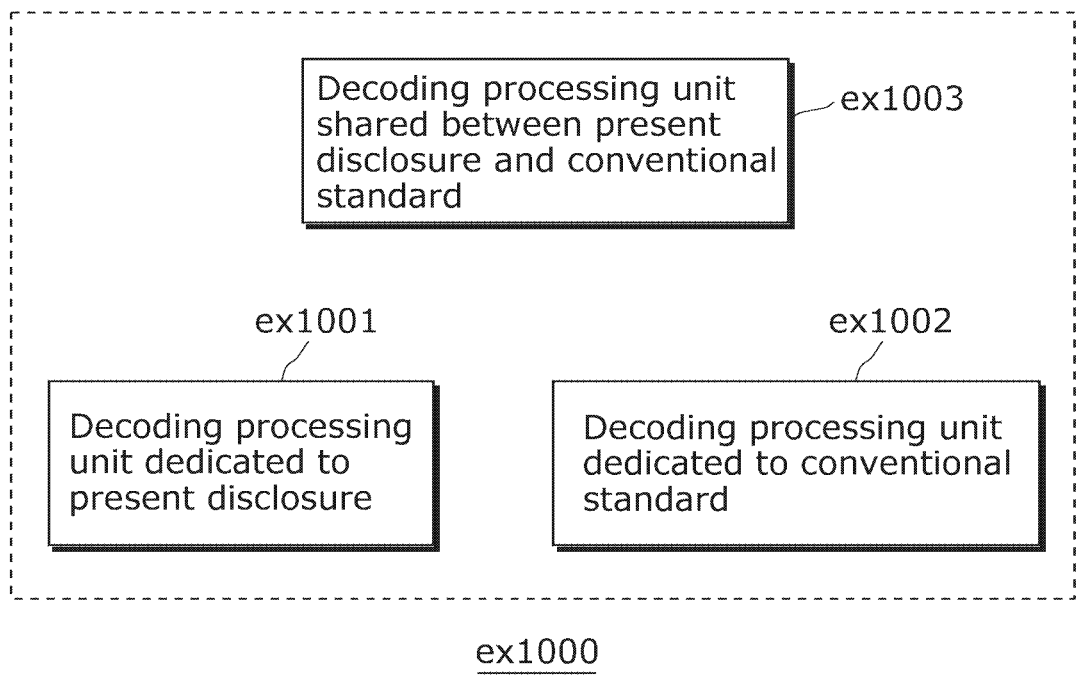
FIG. 56B is a diagram showing another example of a configuration for sharing a module of the signal processing unit.

Furthermore, ex1000 in FIG. 56B shows another example in that processing is partly shared. This example uses a configuration including a dedicated decoding processing unit ex1001 that supports the processing unique to an aspect of the present disclosure, a dedicated decoding processing unit ex1002 that supports the processing unique to another conventional standard, and a decoding processing unit ex1003 that supports processing to be shared between the moving picture decoding method according to the aspect of the present disclosure and the conventional moving picture decoding method. Here, the dedicated decoding processing units ex1001 and ex1002 are not necessarily specialized for the processing according to the aspect of the present disclosure and the processing of the conventional standard, respectively, and may be the ones capable of implementing general processing. Furthermore, the configuration of the present embodiment can be implemented by the LSI ex500.

As such, reducing the scale of the circuit of an LSI and reducing the cost are possible by sharing the decoding processing unit for the processing to be shared between the moving picture decoding method according to the aspect of the present disclosure and the moving picture decoding method in conformity with the conventional standard

INDUSTRIAL APPLICABILITY

The image coding method and the image decoding method according to the present disclosure produce advantageous effects of preventing deterioration in an image quality and improving processing efficiency, and are applicable to a variety of purposes such as accumulation, transmission, and communication of an image. The image coding method and the image decoding method according to the present disclosure can be used for, for example, a high-resolution information display device or capturing device, such as a television, a digital video recorder, a car navigation, a cellular phone, a digital camera, a digital video camera, and so on, and are useful.

The invention claimed is:

1. A non-transitory computer-readable recording medium for use in a computer, the recording medium having a computer program recorded thereon for causing the computer to execute operations comprising:
 performing context arithmetic coding to code (i) first information indicating whether or not to perform sample adaptive offset (SAO) processing for a first region of an image and (ii) second information indicating whether or not to use, in the SAO processing for the first region, information on SAO processing for a region other than the first region, the context arithmetic coding being arithmetic coding using a variable probability, the SAO processing being offset processing on a pixel value; and
 performing bypass arithmetic coding to code other information, the other information being information on the SAO processing for the first region and different from the first information and the second information, the other information being coded after the first information and the second information are coded, the bypass arithmetic coding being arithmetic coding using a fixed probability,
 wherein the other information includes (i) third information indicating whether the SAO processing for the first region is edge offset processing or band offset processing and (ii) fourth information indicating an absolute value of an offset value, the edge offset processing being performed according to an edge, the band offset processing being performed according to a pixel value, and
 wherein when the SAO processing for the first region is the band offset processing, the other information includes (i) fifth information indicating whether the offset value is positive or negative and (ii) sixth information indicating a scope of application of the offset value.

2. The non-transitory computer-readable recording medium according to claim 1,
 wherein the second information includes at least one of (i) information indicating whether or not information on SAO processing for a left region is used in the SAO processing for the first region and (ii) information indicating whether or not information on SAO processing for an upper region is used in the SAO processing for the first region, the left region being adjacent to the first region and being to the left of the first region, the upper region being adjacent to the first region and being on top of the first region.

3. An image coding apparatus comprising:
 control circuitry; and
 the non-transitory computer-readable recording medium according to claim 1 which is accessible from the control circuitry.

* * * * *